United States Patent
Morita et al.

(10) Patent No.: US 11,692,015 B2
(45) Date of Patent: Jul. 4, 2023

(54) MODIFIED FIBROIN

(71) Applicants: Spiber Inc., Yamagata (JP); Riken, Saitama (JP)

(72) Inventors: Keisuke Morita, Tsuruoka (JP); Yunosuke Abe, Tsuruoka (JP); Takehisa Maekawa, Tsuruoka (JP); Koichi Kotaka, Tsuruoka (JP); Junichi Sugahara, Tsuruoka (JP); Keiji Numata, Wako (JP)

(73) Assignees: Spiber Inc., Yamagata (JP); Riken, Saitama (JP)

( * ) Notice: Subject to any disclaimer, the term of this patent is extended or adjusted under 35 U.S.C. 154(b) by 327 days.

(21) Appl. No.: 16/633,589

(22) PCT Filed: Jul. 25, 2018

(86) PCT No.: PCT/JP2018/027974
§ 371 (c)(1),
(2) Date: Jan. 24, 2020

(87) PCT Pub. No.: WO2019/022163
PCT Pub. Date: Jan. 31, 2019

(65) Prior Publication Data
US 2020/0207817 A1    Jul. 2, 2020

(30) Foreign Application Priority Data
Jul. 26, 2017    (JP) .................. 2017-144586

(51) Int. Cl.
C07K 14/435    (2006.01)
C12N 15/63    (2006.01)
D01F 4/02    (2006.01)

(52) U.S. Cl.
CPC ........ C07K 14/43518 (2013.01); C12N 15/63 (2013.01); D01F 4/02 (2013.01)

(58) Field of Classification Search
None
See application file for complete search history.

(56) References Cited

U.S. PATENT DOCUMENTS

| | | | |
|---|---|---|---|
| 2019/0135881 A1 * | 5/2019 | Morita | ............. C07K 14/43518 |
| 2020/0207817 A1 | 7/2020 | Morita et al. | |

FOREIGN PATENT DOCUMENTS

| | | |
|---|---|---|
| EP | 3476859 A1 | 5/2019 |
| JP | H02-006869 B2 | 2/1990 |
| JP | H06-294068 A | 10/1994 |
| JP | 2005-502347 A | 1/2005 |
| JP | 2009-505668 A | 2/2009 |
| JP | 2012-055269 A | 3/2012 |
| JP | 2013-506058 A | 2/2013 |
| JP | 2014-502140 A | 1/2014 |
| JP | 6807089 B2 | 1/2021 |
| WO | 03/020916 A2 | 3/2003 |
| WO | 2007/025719 A1 | 3/2007 |
| WO | 2011/038401 A2 | 3/2011 |
| WO | 2011/113592 A1 | 9/2011 |
| WO | 2012/050919 A2 | 4/2012 |
| WO | 2015/042164 A2 | 3/2015 |
| WO | 2017/222034 A1 | 12/2017 |

OTHER PUBLICATIONS

Extended European Search Report issued in counterpart European Patent Application No. 18838960.5 dated Apr. 7, 2021.
Scheibel, "Spider silks: recombinant synthesis, assembly, spinning, and engineering of synthetic proteins," Microbial Cell Factories, 3 (1): 14 (2004).
Lefevre et al., "Protein Secondary Structure and Orientation in Silk as Revealed by Raman Spectromicroscopy," Biophysical Journal, 92 (8): 2885-2895 (2007).
International Search Report issued in corresponding International Patent Application No. PCT/JP2018/027974 dated Sep. 18, 2018.
International Preliminary Report on Patentability and Written Opinion issued in corresponding International Patent Application No. PCT/JP2018/027974 dated Feb. 6, 2020.
Asakura et al., "Encyclopedia of Agricultural Science: Silk Production and Processing," Academic Press, 4: 1-11 (1994).
Scheibel, "Spider silks: recombinant synthesis, assembly, spinning, and engineering of synthetic proteins," Microbial Cell Factories, 3:14 1-10 (2004).
Lazaris et al., "Spider Silk Fibers Spun from Soluble Recombinant Silk Produced in Mammalian Cells," Science, 295: 472-476 (2002).

(Continued)

*Primary Examiner* — Anand U Desai
(74) *Attorney, Agent, or Firm* — Morgan, Lewis & Bockius LLP

(57) ABSTRACT

The present invention relates to a modified fibroin including a domain sequence represented by Formula 1: $[(A)_n\text{motif-REP}]_m$ or Formula 2: $[(A)_n\text{motif-REP}]_m-(A)_n$ motif, in which the domain sequence has an amino acid sequence with a reduced content of a glutamine residue equivalent to an amino acid in which one or a plurality of glutamine residues in REP are deleted or substituted with other amino acid residues, as compared with a naturally occurring fibroin.

23 Claims, 3 Drawing Sheets
Specification includes a Sequence Listing.

(56) References Cited

OTHER PUBLICATIONS

Zhang et al., "Microbial production of amino acid-modified spider dragline silk protein with intensively improved mechanical properties," Preparative Biochemistry and Biotechnology, 46: 552-558 (2016).

Teule et al., "Modificatios of spider silk sequences in an attempt to control the mechanical properties of the synt," Journal of Materials Science, 42: 8974-8985 (2007).

Blackledge et al., "How super is supercontraction? Persistent versus cyclic responses to humidity in spider dragline silk," Journal of Experimental Biology, 212: 1981-1989 (2009).

* cited by examiner

MODIFIED FIBROIN

Sequence Listing Submission Via EFS-Web

A computer readable text file, entitled "SequenceListing.txt," created on or about Jan. 23, 2020 with a file size of about 249 kb contains the sequence listing for this application and is hereby incorporated by reference in its entirety.

TECHNICAL FIELD

The present invention relates to a modified fibroin. More particularly, the present invention relates to a modified fibroin with a reduced content of glutamine residue. The present invention also relates to a nucleic acid encoding a modified fibroin, an expression vector including the nucleic acid sequence, a host transformed with the expression vector, and a product made from a modified fibroin.

BACKGROUND ART

Fibroin is a type of fibrous protein and contains up to 90% of glycine, alanine and serine residues leading to the formation of a β-pleated sheet (Non-Patent Literature 1). Proteins (silk proteins, hornet silk proteins, and spider silk proteins) and the like constituting the yarn produced by insects and spiders are known as fibroin.

Silk proteins have excellent mechanical properties, hygroscopic properties and deodorizing properties and are widely used as raw materials for garments. In addition, the silk yarn is an immuno-tolerant natural fiber and has high biocompatibility and is therefore also used for surgical sutures.

Up to seven types of silk glands exist in spider, each of which produces fibroin (spider silk protein) with different properties. According to the organ of the source, spider silk proteins are designated as a major ampullate spider protein (MaSp) with high toughness, a minor ampullate spider protein (MiSp) with high elongatability, and flagelliform (Flag), tubuliform, aggregate, aciniform, and pyriform spider silk proteins. In particular, structural studies have been intensively conducted in the major ampullate spider protein exhibiting high toughness due to the fact that the protein has excellent strength and elongatability (Patent Literature 1 and Patent Literature 2).

As a structure specific to fibroin, a structure in which amino acid motifs classified as GPGXX, an elongation region rich in alanine residues (($A)_n$ or $(GA)_n$), GGX, and a spacer are repeated is known (Non-Patent Literature 2). In addition, it has been reported that substitution of the $(GA)_n$ motif with the $(A)_n$ motif leads to reduced elongatability but increased tensile strength, an increase in the number of GPGXX motifs leads to increased elongatability, and substitution of several GPGXX motifs with the $(A)_n$ motifs leads to increased tensile strength (Patent Literature 2). In addition, the GGX and GPGXX motifs are thought to have a flexible helical structure that imparts elasticity to yarn (Patent Literature 3)

Recombinant spider silk proteins and recombinant silk proteins are produced in several heterologous protein production systems. For example, many cases of production of recombinant fibroin by organisms such as goat, silkworm, plant, mammalian cell, yeast, mold, gram-negative bacterium, and gram-positive bacterium as a host have been reported, and certain outcomes have been obtained. (Non-patent Literature 3, Patent Literatures 4 and 5).

A fibroin fiber obtained by spinning fibroin has the property of shrinking when immersed in water or hot water, exposed to a high humidity environment, or the like. This property causes various problems in the manufacturing process and productization, and also affects the product made of the fiber.

As an anti-shrinking method for preventing shrinkage of the product, for example, a method for preventing shrinkage of a silk fabric, in which the silk fabric using a strong twisted yarn that has been scoured is immersed in water, other solvent, or a mixed system thereof in a tension state and heated for a predetermined time (Patent Literature 6), a method for fixing a shape of an animal fiber product, in which the animal fiber product shaped in a required form is subjected to a treatment of being brought into contact with a high-pressured saturated stream at 120° C. to 200° C. to fix the shape at the time of the stream treatment (Patent Literature 7), and the like are disclosed.

CITATION LIST

Patent Literature

[Patent Literature 1] Japanese Unexamined Patent Publication No. 2012-55269
[Patent Literature 2] Japanese Unexamined Patent Publication No. 2005-502347
[Patent Literature 3] Japanese Unexamined Patent Publication No. 2009-505668
[Patent Literature 4] Japanese Unexamined Patent Publication No. 2014-502140
[Patent Literature 5] International Patent Publication No. WO2015/042164
[Patent Literature 6] Japanese Examined Patent Publication No. H2-6869
[Patent Literature 7] Japanese Unexamined Patent Publication No. H6-294068

Non Patent Literature

[Non-Patent Literature 1] Asakura et al., Encyclopedia of Agricultural Science, Academic Press: New York, N.Y., 1994, Vol. 4, pp. 1-11
[Non-Patent Literature 2] Microbial Cell Factories, 2004, 3:14
[Non-Patent Literature 3] Science, 2002, Vol. 295, pp. 472-476

SUMMARY OF INVENTION

Problems to be Solved by the Invention

The anti-shrinking methods as disclosed in Patent Literatures 6 and 7 are industrially disadvantageous because the operation is complicated and the number of steps is increased. On the other hand, it is industrially useful if the shrinkage of the fibroin fiber itself can be suppressed or reduced. However, to date, no fibroin fiber having a suppressed or reduced shrinkage, or a modified fibroin constituting the fibroin fiber is known.

An object of the present invention is to provide a modified fibroin capable of spinning a fibroin fiber with reduced shrinkage.

Means for Solving the Problems

The present inventors have found that a fibroin fiber with reduced shrinkage can be obtained by reducing the content of glutamine residue present in fibroin. Furthermore, the present inventors have found that the film obtained by shaping the fibroin has waterproofness. The present invention has been completed based on such novel findings.

That is, the present invention relates to, for example, each of the following inventions.

[1] A modified fibroin including a domain sequence represented by Formula 1: [(A)$_n$ motif-REP]$_m$ or Formula 2: [(A)$_n$ motif-REP]$_m$–(A)$_n$ motif, in which the domain sequence has an amino acid sequence with a reduced content of a glutamine residue equivalent to an amino acid in which one or a plurality of glutamine residues in REP are deleted or substituted with other amino acid residues, as compared with a naturally occurring fibroin.

[In Formula 1 and Formula 2, (A)$_n$ motif represents an amino acid sequence consisting of 4 to 27 amino acid residues and the number of alanine residues with respect to the total number of amino acid residues in the (A)$_n$ motif is 80% or more. REP represents an amino acid sequence consisting of 10 to 200 amino acid residues. m represents an integer of 10 to 300. A plurality of (A)$_n$ motifs may be the same amino acid sequence or different amino acid sequences. A plurality of REPs may be the same amino acid sequence or different amino acid sequences.]

[2] The modified fibroin according to aspect [1], in which the REP contains a GPGXX (where X represents an amino acid residue other than a glycine residue) motif and has a GPGXX motif content of 10% or more.

[3] The modified fibroin according to aspect [1] or [2], in which a glutamine residue content rate is 9% or less.

[4] The modified fibroin according to any one of aspects [1] to [3], in which the other amino acid residues are amino acid residues selected from the group consisting of isoleucine (I), valine (V), leucine (L), phenylalanine (F), cysteine (C), methionine (M), alanine (A), glycine (G), threonine (T), serine (S), tryptophan (W), tyrosine (Y), proline (P) and histidine (H).

[5] The modified fibroin according to any one of aspects [1] to [4], in which a hydrophobicity of the REP is −0.8 or more.

[6] The modified fibroin according to any one of aspects [1] to [5], further including an amino acid sequence equivalent to an amino acid sequence in which one or a plurality of amino acid residues are substituted, deleted, inserted and/or added, as compared with the naturally occurring fibroin.

[7] The modified fibroin according to aspect [6], in which the naturally occurring fibroin is a fibroin derived from insects or spiders. [8] The modified fibroin according to aspect [7], in which the naturally occurring fibroin is a major ampullate spider protein (MaSp) or minor ampullate spider protein (MiSp) of spiders.

[9] A modified fibroin including: an amino acid sequence set forth in SEQ ID NO: 2, SEQ ID NO: 3, SEQ ID NO: 4, SEQ ID NO: 5, SEQ ID NO: 6, SEQ ID NO: 16, or SEQ ID NO: 17; or an amino acid sequence having 90% or more sequence identity with the amino acid sequence set forth in SEQ ID NO: 2, SEQ ID NO: 3, SEQ ID NO: 4, SEQ ID NO: 5, SEQ ID NO: 6, SEQ ID NO: 16, or SEQ ID NO: 17.

[10] The modified fibroin according to any one of aspects [1] to [9], further including a tag sequence at either or both of a N-terminal and a C-terminal.

[11] The modified fibroin according to aspect [10], in which the tag sequence includes an amino acid sequence set forth in SEQ ID NO: 7.

[12] A modified fibroin including: an amino acid sequence set forth in SEQ ID NO: 9, SEQ ID NO: 10, SEQ ID NO: 11, SEQ ID NO: 12, SEQ ID NO: 13, SEQ ID NO: 19, or SEQ ID NO: 20; or an amino acid sequence having 90% or more sequence identity with the amino acid sequence set forth in SEQ ID NO: 9, SEQ ID NO: 10, SEQ ID NO: 11, SEQ ID NO: 12, SEQ ID NO: 13, SEQ ID NO: 19, or SEQ ID NO: 20.

[13] A nucleic acid that encodes the modified fibroin according to aspects [1] to [12].

[14] A nucleic acid hybridizing with a complementary strand of the nucleic acid according to aspect [13] under stringent conditions and encoding a modified fibroin including a domain sequence represented by Formula 1: [(A)$_n$ motif-REP]$_m$ or Formula 2: [(A)$_n$ motif-REP]$_m$–(A)$_n$ motif.

[In Formula 1 and Formula 2, (A)$_n$ motif represents an amino acid sequence consisting of 4 to 27 amino acid residues and the number of alanine residues with respect to the total number of amino acid residues in the (A)$_n$ motif is 80% or more, REP represents an amino acid sequence consisting of 10 to 200 amino acid residues, m represents an integer of 10 to 300, a plurality of (A)$_n$ motifs may be the same amino acid sequence or different amino acid sequences, and a plurality of REPs may be the same amino acid sequence or different amino acid sequences.]

[15] A nucleic acid having 90% or more sequence identity with the nucleic acid according to aspect [13] and encoding a modified fibroin including a domain sequence represented by Formula 1: [(A)$_n$ motif-REP]$_m$ or Formula 2: [(A)$_n$ motif-REP]$_m$–(A)$_n$ motif.

[In Formula 1 and Formula 2, (A)$_n$ motif represents an amino acid sequence consisting of 4 to 27 amino acid residues and the number of alanine residues with respect to the total number of amino acid residues in the (A)$_n$ motif is 80% or more. REP represents an amino acid sequence consisting of 10 to 200 amino acid residues. m represents an integer of 10 to 300. A plurality of (A)$_n$ motifs may be the same amino acid sequence or different amino acid sequences. A plurality of REPs may be the same amino acid sequence or different amino acid sequences.]

[16] An expression vector including: the nucleic acid sequence according to any one of aspects [13] to [15]; and one or a plurality of regulatory sequences operably linked to the nucleic acid sequence according to any one of aspects [13] to [15].

[17] The expression vector according to aspect [16], which is a plasmid vector or a viral vector.

[18] A host transformed with the expression vector according to aspect [16] or [17].

[19] The host according to aspect [18], which is a prokaryote.

[20] The host according to aspect [19], in which the prokaryote is a microorganism belonging to a genus selected from the group consisting of *Escherichia, Brevibacillus, Serratia, Bacillus, Microbacterium, Brevibacterium, Corynebacterium* and *Pseudomonas*.

[21] The host according to aspect [18], which is a eukaryote.

[22] The host according to aspect [21], in which the eukaryote is a yeast, a filamentous fungus, or an insect cell.

[23] The host according to aspect [22], in which the yeast is a yeast belonging to a genus selected from the group consisting of *Saccharomyces, Schizosaccharomyces, Kluyveromyces, Trichosporon, Schwanniomyces, Pichia, Candida, Yarrowia*, and *Hansenula*.

[24] The host according to aspect [23], in which the yeast belonging to a genus *Saccharomyces* is *Saccharomyces cerevisiae*, the yeast belonging to a genus *Schizosaccharomyces* is *Schizosaccharomyces pombe*, the yeast belonging to a genus *Kluyveromyces* is *Kluyveromyces lactis*, the yeast belonging to a genus *Trichosporon* is *Trichosporon pullulans*, the yeast belonging to a genus *Schwanniomyces* is

*Schwanniomyces alluvius*, the yeast belonging to a genus *Pichia* is *Pichia pastoris*, the yeast belonging to a genus *Candida* is *Candida albicans*, the yeast belonging to a genus *Yarrowia* is *Yarrowia lipolytica*, and the yeast belonging to a genus *Hansenula* is *Hansenula polymorpha*.

[25] The host according to aspect [22], in which the filamentous fungus is a filamentous fungus belonging to a genus selected from the group consisting of *Aspergillus, Penicillium*, and *Mucor*.

[26] The host according to aspect [25], in which the filamentous fungus belonging to a genus *Aspergillus* is *Aspergillus oryzae*, the filamentous fungus belonging to a genus *Penicillium* is *Penicillium chrysogenum*, and the filamentous fungus belonging to a genus *Mucor* is *Mucor fragilis*.

[27] The host according to aspect [22], in which the insect cell is a lepidopteran insect cell.

[28] The host according to aspect [27], in which the insect cell is an insect cell derived from *Spodoptera frugiperda* or an insect cell derived from *Trichoplusia ni*.

[29] A product including the modified fibroin according to any one of aspects [1] to [12], the product being selected from the group consisting of a fiber, a yarn, a film, a foam, a grain, a nanofibril, a gel, and a resin.

In addition, the present invention also relates to, for example, each of the following inventions.

[30] An artificially modified fibroin fiber including a modified fibroin, in which the artificially modified fibroin fiber elongates when wetted and shrinks when dried from the wetted state.

[31] The artificially modified fibroin fiber according to aspect [30], in which a restoration rate defined by Expression (1) is 95% or more.

$$\text{restoration rate} = (\text{length of artificially modified fibroin fiber when dried from wetted state}/\text{length of artificially modified fibroin fiber before being wetted}) \times 100(\%) \quad (1)$$

[32] The artificially modified fibroin fiber according to aspect [30] or [31], in which the artificially modified fibroin fiber is a fiber having a shrinkage history of irreversibly being shrunk by contact with water after spinning and a shrinkage rate A defined by Expression (2) of 2% or more.

$$\text{shrinkage rate } A = \{1 - (\text{length of fiber irreversibly shrunk by contact with water after spinning}/\text{length of fiber before contact with water and after spinning})\} \times 100(\%) \quad (2)$$

[33] The artificially modified fibroin fiber according to any one of aspects [30] to [32], in which the artificially modified fibroin fiber is a fiber having a shrinkage history of irreversibly being shrunk by contact with water after spinning and then further being shrunk by drying and a shrinkage rate B defined by Expression (3) of more than 7%.

$$\text{shrinkage rate } B = \{1 - (\text{length of fiber irreversibly shrunk by contact with water after spinning and then further shrunk by drying}/\text{length of fiber before contact with water and after spinning})\} \times 100(\%) \quad (3)$$

[34] The artificially modified fibroin fiber according to any one of aspects [30] to [33], in which the modified fibroin is the modified fibroin according to any one of aspects [1] to [12].

[35] The artificially modified fibroin fiber according to any one of aspects [30] to [34], in which an elongation rate defined by Expression (4) is 17% or less.

$$\text{elongation rate} = \{(\text{length of artificially modified fibroin fiber when wetted}/\text{length of artificially modified fibroin fiber before being wetted}) - 1\} \times 100(\%) \quad (4)$$

[36] The artificially modified fibroin fiber according to any one of aspects [30] to [35], in which a shrinkage rate C defined by Expression (5) is 15% or less.

$$\text{shrinkage rate } C = \{1 - (\text{length of artificially modified fibroin fiber when dried from wetted state}/\text{length of artificially modified fibroin fiber when wetted})\} \times 100(\%) \quad (5)$$

[37] A method for producing an artificially modified fibroin fiber, including a shrinking step of bring a raw fiber before contact with water and after spinning into contact with water to cause irreversible shrinkage, and then drying the raw fiber to cause further shrinkage, in which the raw fiber includes a modified fibroin.

[38] The production method according to aspect [37], in which a shrinkage rate A of the raw fiber defined by Expression (2) is 2% or more.

$$\text{shrinkage rate } A = \{1 - (\text{length of fiber irreversibly shrunk by contact with water after spinning}/\text{length of fiber before contact with water and after spinning})\} \times 100(\%) \quad (2)$$

[39] The production method according to aspect [37] or [38], in which a shrinkage rate B of the raw fiber defined by Expression (3) is more than 7%.

$$\text{shrinkage rate } B = \{1 - (\text{length of fiber irreversibly shrunk by contact with water after spinning and then further shrunk by drying}/\text{length of fiber before contact with water and after spinning})\} \times 100(\%) \quad (3)$$

[40] The production method according to aspects [37] to [39], in which the modified fibroin is the modified fibroin according to any one of aspects [1] to [12].

Effects of the Invention

According to the present invention, it is possible to provide a modified fibroin capable of spinning a fibroin fiber with reduced shrinkage. In addition, it is possible to provide a modified fibroin capable of producing a fibroin film having reduced water absorbency and waterproofness.

In addition, according to the present invention, it is possible to provide an artificially modified fibroin fiber in which the degree of elongation is approximately the same as the degree of shrinkage (restoration rate is close to 100%) and which has the characteristic of being able to restore the original length thereof, and a method for producing the same, in a case where the dimension thereof changes (elongation and shrinkage) due to contact with water and subsequent drying.

BRIEF DESCRIPTION OF DRAWINGS

FIG. 2 is a graph showing an example of a change in the length of a fibroin fiber due to contact with water or the like.

EMBODIMENTS FOR CARRYING OUT THE INVENTION

Figure 1:
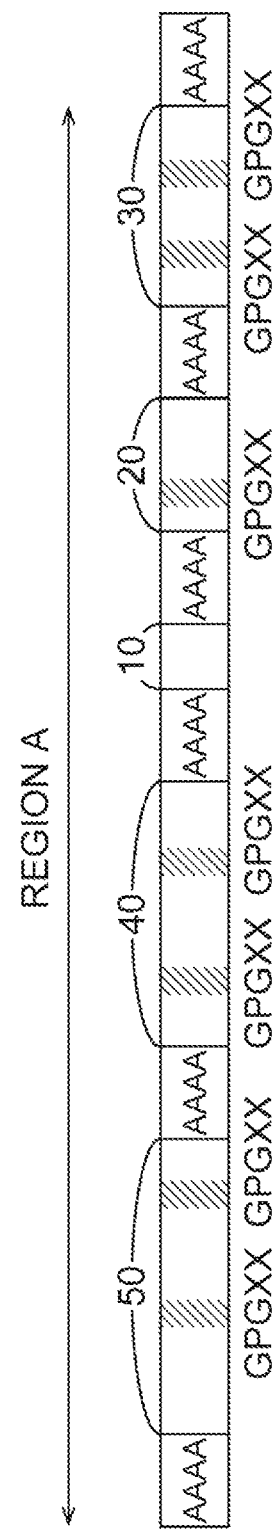
FIG. 1 is a schematic diagram showing a domain sequence of a modified fibroin.

Hereinafter, embodiments for carrying out the present invention will be described in detail. However, the present invention is not limited to the following embodiments.

[Modified Fibroin]

The modified fibroin according to the present invention is a protein including a domain sequence represented by Formula 1: $[(A)_n$ motif-REP$]_m$ or Formula 2: $[(A)_n$ motif-REP$]_m$ $-(A)_n$ motif. In the modified fibroin, an amino acid sequence (N-terminal sequence and C-terminal sequence) may be further added to either or both of the N-terminal side and the C-terminal side of the domain sequence. The N-terminal sequence and the C-terminal sequence, although not limited thereto, are typically regions that do not have repetitions of amino acid motifs characteristic of fibroin and consist of amino acids of about 100 residues.

The term "modified fibroin" as used herein means a fibroin whose domain sequence is different from the amino acid sequence of naturally occurring fibroin. The "naturally occurring fibroin" referred to in the present invention is also a protein including a domain sequence represented by Formula 1: $[(A)_n$ motif-REP$]_m$ or Formula 2: $[(A)_n$ motif-REP$]_m$ $-(A)_n$ motif.

The "modified fibroin" may be a fibroin whose amino acid sequence has been modified based on naturally occurring fibroin (for example, a fibroin whose amino acid sequence has been modified by altering a cloned gene sequence of naturally occurring fibroin) or a fibroin artificially designed and synthesized independently of naturally occurring fibroin (for example, a fibroin having a desired amino acid sequence by chemically synthesizing a nucleic acid encoding the designed amino acid sequence), as long as it has the amino acid sequence specified in the present invention.

The term "domain sequence" as used herein refers to an amino acid sequence which produces a crystalline region (typically, equivalent to $(A)_n$ motif of an amino acid sequence) and an amorphous region (typically, equivalent to REP of an amino acid sequence) peculiar to fibroin and means an amino acid sequence represented by Formula 1: $[(A)_n$ motif-REP$]_m$ or Formula 2: $[(A)_n$ motif-REP$]_m$-$(A)_n$ motif. Here, the $(A)_n$ motif represents an amino acid sequence consisting of 4 to 27 amino acid residues, and the number of alanine residues with respect to the total number of amino acid residues in the $(A)_n$ motif is 80% or more. REP represents an amino acid sequence consisting of 10 to 200 amino acid residues. m represents an integer of 10 to 300. A plurality of $(A)_n$ motifs may be the same amino acid sequence or different amino acid sequences. A plurality of REPs may be the same amino acid sequence or different amino acid sequences.

The $(A)_n$ motif may be such that the number of alanine residues is 80% or more with respect to the total number of amino acid residues in the $(A)_n$ motif, but it is preferably 85% or more, more preferably 90% or more, still more preferably 95% or more, and even still more preferably 100% (which means that the $(A)_n$ motif consists of only alanine residues). It is preferable that at least seven of a plurality of $(A)_n$ motifs in the domain sequence consist of only alanine residues. The phrase "consist of only alanine residues" means that the $(A)_n$ motif has an amino acid sequence represented by $(A)_n$ (where A represents an alanine residue and n represents an integer of 4 to 27, preferably an integer of 4 to 20, and more preferably an integer of 4 to 16).

The modified fibroin according to the present embodiment may have an amino acid sequence with a reduced content of glutamine residue, as compared with naturally occurring fibroin. Since the modified fibroin according to the present embodiment has a reduced glutamine residue content, the fibroin fiber obtained by spinning the modified fibroin has reduced shrinkage. Moreover, the film obtained by shaping the fibroin has waterproofness.

It is preferable that the modified fibroin according to the present embodiment includes at least one motif selected from GGX motif or GPGXX motif (where G represents a glycine residue, P represents a proline residue, and X represents an amino acid residue other than a glycine residue) in the amino acid sequence of REP. Since these motifs are included in REP, the elongatability of the modified fibroin can be improved.

In a case where the modified fibroin according to the present embodiment includes a GPGXX motif in REP, a GPGXX motif content rate is usually 1% or more, may be 5% or more, and is preferably 10% or more. With this configuration, the elongatability of the modified fibroin can be further improved. The upper limit of the GPGXX motif content rate is not particularly limited, may be 50% or less and may be 30% or less.

In the present specification, the "GPGXX motif content rate" is a value calculated by the following method.

In a fibroin including a domain sequence represented by Formula 1: $[(A)_n$ motif-REP$]_m$ or Formula 2: $[(A)_n$ motif-REP$]_m$-$(A)_n$ motif, in a case where the number obtained by tripling the total number of the GPGXX motifs in all REPs included in a sequence excluding the sequence from the $(A)_n$ motif located at the most C-terminal side to the C-terminal of the domain sequence from the domain sequence (that is, equivalent to the total number of G and P in the GPGXX motifs) is set as x, and the total number of amino acid residues in all REPs excluding the sequence from the $(A)_n$ motif located at the most the C-terminal side to the C-terminal of the domain sequence from the domain sequence and further excluding $(A)_n$ motifs is set as y, the GPGXX motif content rate is calculated as x/y.

For the calculation of the GPGXX motif content rate, the "sequence excluding a sequence from the $(A)_n$ motif located at the most C-terminal side to the C-terminal of the domain sequence from the domain sequence" is used to exclude the effect occurring due to the fact that the "sequence from the $(A)_n$ motif located at the most C-terminal side to the C-terminal of the domain sequence" (sequence equivalent to REP) may include a sequence that is not correlated with the sequence characteristic of fibroin, which influences the calculation result of the GPGXX motif content rate in a case where m is small (that is, in a case where the domain sequence is short). In a case where a "GPGXX motif" is located at the C-terminal of REP, it is treated as the "GPGXX motif" even if "XX" is, for example, "AA".

FIG. 1 is a schematic diagram showing a domain sequence of a modified fibroin. The calculation method of the GPGXX motif content rate will be specifically described with reference to FIG. 1. First, in a domain sequence of a modified fibroin shown in FIG. 1 ($[(A)_n$ motif-REP$]_m$-$(A)_n$ motif] type), since all REPs are included in the "sequence excluding a sequence from the $(A)_n$ motif located at the most C-terminal side to the C-terminal of the domain sequence from the domain sequence" (shown as "region A" in FIG. 1), the number of GPGXX motifs for calculating x is 7, and x is 7×3=21. Similarly, since all REPs are included in the "sequence excluding a sequence from the $(A)_n$ motif located at the most C-terminal side to the C-terminal of the domain sequence from the domain sequence" (shown as "region A" in FIG. 1), y which is the total number of amino acid residues in all REPs excluding the sequence from the $(A)_n$ motif located at the most the C-terminal side to the C-terminal of the domain sequence from the domain sequence and further excluding $(A)_n$ motifs, is 50+40+10+20+30=150. Next, x/y (%) can be calculated by dividing x by y and is 21/150=14.0% in a case of the modified fibroin of FIG. 1.

In the modified fibroin according to the present embodiment, a glutamine residue content rate is preferably 9% or less, more preferably 7% or less, still more preferably 4% or less, and particularly preferably 0%. With this configuration, the effect of the present invention is further remarkably exhibited.

In the present specification, the "glutamine residue content rate" is a value calculated by the following method.

In a fibroin including a domain sequence represented by Formula 1: $[(A)_n$ motif-REP$]_m$ or Formula 2: $[(A)_n$ motif-REP$]_m$–$(A)_n$ motif, in a case where the total number of glutamine residues in all REPs included in a sequence (sequence equivalent to "region A" in FIG. 1) excluding the sequence from the $(A)_n$ motif located at the most C-terminal side to the C-terminal of the domain sequence from the domain sequence is set as w, and the total number of amino acid residues in all REPs excluding the sequence from the $(A)_n$ motif located at the most the C-terminal side to the C-terminal of the domain sequence from the domain sequence and further excluding $(A)_n$ motifs is set as y, the glutamine residue content rate is calculated as w/y. For the calculation of the glutamine residue content rate, the "sequence excluding a sequence from the $(A)_n$ motif located at the most C-terminal side to the C-terminal of the domain sequence from the domain sequence" is used for the same reason described above.

The domain sequence of the modified fibroin according to the present embodiment may include an amino acid sequence equivalent to an amino acid sequence in which one or a plurality of glutamine residues in REP are deleted or substituted with other amino acid residues, as compared with naturally occurring fibroin.

The "other amino acid residue" may be an amino acid residue other than a glutamine residue, but is preferably an amino acid residue having a higher hydropathy index than that of a glutamine residue. Regarding the hydropathy index of amino acid residues, known indices (Hydropathy index: Kyte J, & Doolittle R (1982) from "A simple method for displaying the hydropathic character of a protein", J. Mol. Biol., 157, pp. 105-132) may be used as a reference. Specifically, the hydropathy index (hereinafter also referred to as "HI") of each amino acid is as shown in Table 1 below.

TABLE 1

| Amino acid | HI | Amino acid | HI |
| --- | --- | --- | --- |
| Isoleucine (I) | 4.5 | Tryptophan (W) | −0.9 |
| Valine (V) | 4.2 | Tyrosine (Y) | −1.3 |
| Leucine (L) | 3.8 | Proline (P) | −1.6 |
| Phenylalanine (F) | 2.8 | Histidine (H) | −3.2 |
| Cysteine (C) | 2.5 | Asparagine (N) | −3.5 |
| Methionine (M) | 1.9 | Aspartic acid (D) | −3.5 |
| Alanine (A) | 1.8 | Glutamine (Q) | −3.5 |
| Glycine (G) | −0.4 | Glutamic acid (E) | −3.5 |
| Threonine (T) | −0.7 | Lysine (K) | −3.9 |
| Serine (S) | −0.8 | Arginine (R) | −4.5 |

As shown in Table 1, amino acid residues having a higher hydropathy index than that of a glutamine residue include an amino acid residue selected from isoleucine (I), valine (V), leucine (L), phenylalanine (F), cysteine (C), methionine (M), alanine (A), glycine (G), threonine (T), serine (S), tryptophan (W), tyrosine (Y), proline (P) and histidine (H). Among these, an amino acid residue selected from isoleucine (I), valine (V), leucine (L), phenylalanine (F), cysteine (C), methionine (M) and alanine (A) is more preferable, and an amino acid residue selected from isoleucine (I), valine (V), leucine (L) and phenylalanine (F) is still more preferable.

In the modified fibroin according to the present embodiment, the hydrophobicity of REP is preferably −0.8 or more, more preferably −0.7 or more, still more preferably 0 or more, even still more preferably 0.3 or more, and particularly preferably 0.4 or more. The upper limit of the hydrophobicity of REP is not particularly limited, may be 1.0 or less, and may be 0.7 or less.

In the present specification, the "hydrophobicity of REP" is a value calculated by the following method.

In a fibroin including a domain sequence represented by Formula 1: $[(A)_n$ motif-REP$]_m$ or Formula 2: $[(A)_n$ motif-REP$]_m$–$(A)_n$ motif, in a case where the sum of the hydropathy indices of each amino acid residue in all REPs included in a sequence (sequence equivalent to "region A" in FIG. 1) excluding the sequence from the $(A)_n$ motif located at the most C-terminal side to the C-terminal of the domain sequence from the domain sequence is set as z, and the total number of amino acid residues in all REPs excluding the sequence from the $(A)_n$ motif located at the most the C-terminal side to the C-terminal of the domain sequence from the domain sequence and further excluding $(A)_n$ motifs is set as y, the hydrophobicity of REP is calculated as z/y. For the calculation of the hydrophobicity of REP, the "sequence excluding a sequence from the $(A)_n$ motif located at the most C-terminal side to the C-terminal of the domain sequence from the domain sequence" is used for the same reason described above.

Naturally occurring fibroin is a protein including a domain sequence represented by Formula 1: $[(A)_n$ motif-REP$]_m$ or Formula 2: $[(A)_n$ motif-REP$]_m$–$(A)_n$ motif, specifically, for example, a fibroin produced by insects or spiders.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Sarnia cynthia, Caligura japonica, Antheraea mylitta,* and *Antheraea assama*; and hornet silk proteins discharged by larvae of *Vespa simillima xanthoptera.*

A more specific example of the fibroin produced by insects includes a silkworm fibroin L chain (GenBank Accession No. M76430 (base sequence), AAA27840.1 (amino acid sequence)).

Examples of the fibroin produced by spiders include spider silk proteins produced by spiders belonging to the genus *Araneus* such as *Araneus ventricosus, Araneus diadematus, Araneus pinguis, Araneus pentagrammicus* and *Araneus nojimai,* spiders belonging to the genus *Neoscona* such as *Neoscona scylla, Neoscona nautica, Neoscona adianta* and *Neoscona scylloides,* spiders belonging to the genus Pronus such as Pronous minutes, spiders belonging to the genus *Cyrtarachne* such as *Cyrtarachne bufo* and *Cyrtarachne inaequalis,* spiders belonging to the genus *Gasteracantha* such as *Gasteracantha kuhli* and *Gasteracantha mammosa,* spiders belonging to the genus *Ordgarius* such as *Ordgarius hobsoni* and *Ordgarius sexspinosus,* spiders belonging to the genus *Argiope* such as *Argiope amoena, Argiope minuta* and *Argiope bruennich,* spiders belonging to the genus *Arachnura* such as *Arachnura logio,* spiders belonging to the genus *Acusilas* such as *Acusilas coccineus,* spiders belonging to the genus *Cytophora* such as *Cyrtophora moluccensis, Cyrtophora exanthematica* and *Cyrtophora unicolor,* spiders belonging to the genus *Poltys* such as *Poltys illepidus,* spiders belonging to the genus *Cyclosa* such as *Cyclosa octotuberculata, Cyclosa sedeculata, Cyclosa vallata* and *Cyclosa atrata,* and spiders belonging to the genus *Chorizopes* such as *Chorizopes nipponicus*; and spider silk proteins produced by spiders belonging to the genus *Tetragnatha* such as *Tetragnatha praedonia, Tetragnatha maxillosa, Tetragnatha extensa* and *Tetragnatha squamata*, spiders belonging to the genus *Leucauge* such as *Leucauge magnifica, Leucauge blanda* and *Leucauge subblanda*, spiders belonging to the genus *Nephila* such as *Nephila clavata* and *Nephila pilipes*, spiders belonging to the genus *Menosira* such as *Menosira omata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus* and *Latrodectus tredecimguttatus*, and spiders belonging to the family Tetragnathidae such as spiders belonging to the genus *Euprosthenops*. Examples of spider silk proteins include traction yarn proteins such as MaSp (MaSp1 and MaSp2) and ADF (ADF3 and ADF4), and MiSp (MiSp1 and MiSp2).

More specific examples of the fibroin produced by spiders include fibroin-3 (adf-3) [derived from *Araneus diadematus*] (GenBank Accession Number AAC47010 (amino acid sequence), U47855 (base sequence)), fibroin-4 (adf-4) [derived from *Araneus diadematus*] (GenBank Accession Number AAC47011 (amino acid sequence), U47856 (base sequence)), dragline silk protein spidroin 1 [derived from *Nephila clavipes*] (GenBank Accession Number AAC04504 (amino acid sequence), U37520 (base sequence)), major angullate spidroin 1 [derived from *Latrodectus hesperus*] (GenBank Accession Number ABR68856 (amino acid sequence), EF595246 (base sequence)), dragline silk protein spidroin 2 [derived from *Nephila clavata*] (GenBank Accession Number AAL32472 (amino acid sequence), AF441245 (base sequence)), major anpullate spidroin 1 [derived from *Euprosthenops australis*] (GenBank Accession Number CAJ00428 (amino acid sequence), AJ973155 (base sequence)) and major ampullate spidroin 2 [*Euprosthenops australis*] (GenBank Accession Number CA1\432249.1 (amino acid sequence), AN1490169 (base sequence)), minor ampullate silk protein 1 [*Nephila clavipes*] (GenBank Accession Number AAC14589.1 (amino acid sequence), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence)).

As a further specified example of naturally occurring fibroin, fibroin whose sequence information is registered in NCBI GenBank may be mentioned. For example, sequences thereof may be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

663 types of fibroins (among them, 415 types of fibroins derived from spiders) were extracted by confirming fibroins with amino acid sequence information registered in NCBI GenBank by the method exemplified. Among all the fibroins extracted, there were 129 types of naturally occurring fibroin including a domain sequence represented by Formula 1: [(A)$_n$ motif-REP]$_m$ or Formula 2: [(A)$_n$ motif-REP]$_m$-(A)$_n$ motif. Among these, there were six types of naturally occurring fibroin whose GPGXX motif content rate calculated by the above-described method is 10% or more, as shown in Table 2 below. The glutamine residue content rate of the six types of naturally occurring fibroin shown in Table 2 was 9.2% or more.

TABLE 2

| Accession Number | GPGXX motif content rate | Glutamine residue content rate | Hydrophobicity of REP |
|---|---|---|---|
| DQ059135 | 22.13% | 9.27% | −1.08 |
| AF350276 | 22.88% | 9.30% | −1.08 |
| AF350278 | 26.28% | 13.03% | −1.31 |
| NEPFIBPR | 22.24% | 12.83% | −0.29 |
| ADU47855 | 24.79% | 19.21% | −1.40 |
| AB829892 | 14.54% | 13.80% | −0.11 |

The domain sequence of the modified fibroin according to the present embodiment may further include an amino acid sequence equivalent to an amino acid sequence in which one or a plurality of amino acid residues are substituted, deleted, inserted and/or added, in addition to a modification corresponding to the modification in which one or a plurality of glutamine residues in REP are deleted and/or one or a plurality of glutamine residues in REP are substituted with other amino acid residues, as compared with naturally occurring fibroin. The substitution, deletion, insertion and/or addition of amino acid residues may be carried out by methods well known to those skilled in the art, such as site-directed mutagenesis. Specifically, the modifications may be carried out by a method described in literature such as Nucleic Acid Res. 10, 6487 (1982), and Methods in Enzymology, 100, 448 (1983).

The modified fibroin according to the present embodiment can be obtained by, for example, with respect to a cloned gene sequence of naturally occurring fibroin, deleting one or a plurality of glutamine residues in REP and/or by substituting one or a plurality of glutamine residues in REP with other amino acid residues. Further, for example, the modified fibroin according to the present embodiment may also be obtained by designing an amino acid sequence equivalent to an amino acid sequence in which with respect to the amino acid sequence of naturally occurring fibroin, one or a plurality of glutamine residues in REP are deleted and/or one or a plurality of glutamine residues in REP are substituted with other amino acid residues, and chemically synthesizing a nucleic acid encoding the designed amino acid sequence.

A more specific example of the modified fibroin according to the present invention may be a modified fibroin containing (i) an amino acid sequence set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 or SEQ ID NO: 22, or (ii) an amino acid sequence having 90% or more sequence identity with the amino acid sequence set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 or SEQ ID NO: 22.

The modified fibroin of (i) will be described.

The amino acid sequence set forth in SEQ ID NO: 1 (M_PRT410) is a modified amino acid sequence obtained by changing the number of consecutive alanine residues in (A)$_n$ motif to five, or the like, so as to improve productivity, based on the base sequence and amino acid sequence of *Nephila clavipes* (GenBank Accession Number: P46804.1, GI: 1174415) which is naturally occurring fibroin. However, since M_PRT410 has no modification of glutamine residue (Q), the glutamine residue content rate thereof is the same as the glutamine residue content of naturally occurring fibroin.

The amino acid sequence (M_PRT888) set forth in SEQ ID NO: 2 is obtained by substituting all QQs in M_PRT410 (SEQ ID NO: 1) with VL.

The amino acid sequence (M_PRT965) set forth in SEQ ID NO: 3 is obtained by substituting all QQs in M_PRT410 (SEQ ID NO: 1) with TS and substituting the remaining Q with A.

The amino acid sequence (M_PRT889) set forth in SEQ ID NO: 4 is obtained by substituting all QQs in M_PRT410 (SEQ ID NO: 1) with VL and substituting the remaining Q with I.

The amino acid sequence (M_PRT916) set forth in SEQ ID NO: 5 is obtained by substituting all QQs in M_PRT410 (SEQ ID NO: 1) with VI and substituting the remaining Q with L.

The amino acid sequence (M_PRT918) set forth in SEQ ID NO: 6 is obtained by substituting all QQs in M_PRT410 (SEQ ID NO: 1) with VF and substituting the remaining Q with I.

The amino acid sequence (M_PRT525) set forth in SEQ ID NO: 15 is obtained by, with respect to M_PRT410 (SEQ ID NO: 1), inserting two alanine residues in a region (A5) in which alanine residues are consecutive, and by deleting two domain sequences at the C-terminal side and substituting 13 glutamine (Q) residues with serine (S) residue or proline (P) residue such that the molecular weight thereof becomes approximately the same as that of M_PRT410.

The amino acid sequence (M_PRT699) set forth in SEQ ID NO: 16 is obtained by substituting all QQs in M_PRT525 (SEQ ID NO: 15) with VL.

The amino acid sequence (M_PRT698) set forth in SEQ ID NO: 17 is obtained by substituting all QQs in M_PRT525 (SEQ ID NO: 15) with VL and substituting the remaining Q with I.

The amino acid sequence (M_PRT917) set forth in SEQ ID NO: 21 is obtained by substituting all QQs in M_PRT410 (SEQ ID NO: 1) with LI and substituting the remaining Q with V.

The amino acid sequence (M_PRT1028) set forth in SEQ ID NO: 22 is obtained by substituting all QQs in M_PRT410 (SEQ ID NO: 1) with IF and substituting the remaining Q with T.

The glutamine residue content rate of any of the amino acid sequences set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 and SEQ ID NO: 22 is 9% or less (Table 3).

TABLE 3

| Modified fibroin | Glutamine residue content rate | GPGXX motif content rate | Hydrophobicity of REP |
| --- | --- | --- | --- |
| M_PRT410 (SEQ ID NO: 1) | 17.7% | 27.9% | −1.52 |
| M_PRT888 (SEQ ID NO: 2) | 6.3% | 27.9% | −0.07 |
| M_PRT965 (SEQ ID NO: 3) | 0.0% | 27.9% | −0.65 |
| M_PRT889 (SEQ ID NO: 4) | 0.0% | 27.9% | 0.35 |
| M_PRT916 (SEQ ID NO: 5) | 0.0% | 27.9% | 0.47 |
| M_PRT918 (SEQ ID NO: 6) | 0.0% | 27.9% | 0.45 |
| M_PRT525 (SEQ ID NO: 15) | 13.7% | 26.4% | −1.24 |
| M_PRT699 (SEQ ID NO: 16) | 3.6% | 26.4% | −0.78 |
| M_PRT598 (SEQ ID NO: 17) | 0.0% | 26.4% | −0.03 |
| M_PRT917 (SEQ ID NO: 21) | 0.0% | 27.9% | 0.46 |
| M_PRT1028 (SEQ ID NO: 22) | 0.0% | 28.1% | 0.05 |

The modified fibroin of (i) may consist of the amino acid sequence set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 or SEQ ID NO: 22.

The modified fibroin of (ii) includes an amino acid sequence having 90% or more sequence identity with the acid sequence set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 or SEQ ID NO: 22. The modified fibroin of (ii) is also a protein including a domain sequence represented by Formula 1: $[(A)_n \text{ motif-REP}]_m$ or Formula 2: $[(A)_n \text{ motif-REP}]_m–(A)_n$ motif. The sequence identity is preferably 95% or more.

The modified fibroin of (ii) preferably has the glutamine residue content rate of 9% or less. In addition, the modified fibroin of (ii) preferably has the GPGXX motif content rate of 10% or more.

The above-described modified fibroin may include a tag sequence at either or both of the N-terminal and C-terminal. This makes it possible to isolate, immobilize, detect and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may be an amino acid sequence set forth in SEQ ID NO: 7 (amino acid sequence including His tag).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) showing antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin having a tag sequence may be a modified fibroin containing (iii) an amino acid sequence set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23 or SEQ ID NO: 24, or (iv) an amino acid sequence having 90% or more sequence identity with the amino acid sequence set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23, or SEQ ID NO: 24.

The amino acid sequences set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23 and SEQ ID NO: 24 are respectively amino acid sequences obtained by adding the amino acid sequence (including His tag) set forth in SEQ ID NO: 7 to the N-terminal of the amino acid sequences set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 and SEQ ID NO: 22. Since only the tag sequence is added to the N-terminal, the glutamine residue content rate are not changed, and any of the amino acid sequences set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23 and SEQ ID NO: 24 has the glutamine residue content rate of 9% or less (Table 4).

TABLE 4

| Modified fibroin | Glutamine residue content rate | GPGXX motif content rate | Hydrophobicity of REP |
|---|---|---|---|
| PRT888 (SEQ ID NO: 9) | 6.3% | 27.9% | −0.07 |
| M_PRT965 (SEQ ID NO: 10) | 0.0% | 27.9% | −0.65 |
| M_PRT889 (SEQ ID NO: 11) | 0.0% | 27.9% | 0.45 |
| M_PRT916 (SEQ ID NO: 12) | 0.0% | 27.9% | 0.47 |
| M_PRT918 (SEQ ID NO: 13) | 0.0% | 27.9% | 0.35 |
| M_PRT699 (SEQ ID NO: 19) | 3.6% | 26.4% | −0.78 |
| M_PRT698 (SEQ ID NO: 20) | 0.0% | 26.4% | −0.03 |
| M_PRT917 (SEQ ID NO: 23) | 0.0% | 27.9% | 0.46 |
| M_PRT1028 (SEQ ID NO: 24) | 0.0% | 28.1% | 0.05 |

The modified fibroin of (iii) may consist of the amino acid sequence set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23 or SEQ ID NO: 24.

The modified fibroin of (iv) includes an amino acid sequence having 90% or more sequence identity with the acid sequence set forth in SEQ ID NO: 9, SEQ ID NO: 10, SEQ ID NO: 11, SEQ ID NO: 12, SEQ ID NO: 13, SEQ ID NO: 19, SEQ ID NO: 20, SEQ ID NO: 23 or SEQ ID NO: 24. The modified fibroin of (iv) is also a protein including a domain sequence represented by Formula 1: $[(A)_n$ motif-$REP]_m$ or Formula 2: $[(A)_n$ motif-$REP]_m$–$(A)_n$ motif. The sequence identity is preferably 95% or more.

The modified fibroin of (iv) preferably has the glutamine residue content rate of 9% or less. In addition, the modified fibroin of (iv) preferably has the GPGXX motif content rate of 10% or more.

The above-mentioned modified fibroin may include a secretory signal for releasing the protein produced in the recombinant protein production system to the outside of a host. The sequence of the secretory signal can be appropriately set depending on the type of the host.

[Nucleic Acid]

The nucleic acid according to the present invention encodes the modified fibroin according to the present invention. Specific examples of the nucleic acid include nucleic acids encoding a modified fibroin including an amino acid sequence set forth in SEQ ID NO: 2, SEQ ID NO: 3, SEQ ID NO: 4, SEQ ID NO: 5, SEQ ID NO: 6, SEQ ID NO: 16, SEQ ID NO: 17, SEQ ID NO: 21 or SEQ ID NO: 22, or a protein or the like having an amino acid sequence (tag sequence) set forth in SEQ ID NO: 7 attached to either or both of the N-terminal and C-terminal of these amino acid sequences.

The nucleic acid according to one embodiment is a nucleic acid hybridizing with a complementary strand of the nucleic acid encoding the modified fibroin according to the present invention under stringent conditions and encoding a modified fibroin including a domain sequence represented by Formula 1: $[(A)_n$ motif-$REP]_m$, or Formula 2: $[(A)_n$ motif-REP] $(A)_n$ motif. The modified fibroin encoded by the nucleic acid preferably has the glutamine residue content rate of 9% or less. In addition, the modified fibroin encoded by the nucleic acid preferably has the GPGXX motif content rate of 10% or more.

The term "stringent conditions" refers to conditions under which a so-called specific hybrid is formed and a non-specific hybrid is not formed. The "stringent conditions" may be any of low stringent conditions, moderately stringent conditions and highly stringent conditions. The low stringent conditions mean that hybridization occurs only in the case where there is at least 85% or more identity between the sequences, and include, for example, conditions of hybridization at 42° C. using 5×SSC containing 0.5% SDS. The moderately stringent conditions mean that hybridization occurs only in the case where there is at least 90% or more identity between the sequences, and include, for example, conditions of hybridization at 50° C. using 5×SSC containing 0.5% SDS. The highly stringent conditions mean that hybridization occurs only in the case where there is at least 95% or more identity between the sequences, and include, for example, conditions of hybridization at 60° C. using 5×SSC containing 0.5% SDS.

The nucleic acid according to other embodiment is a nucleic acid having 90% or more sequence identity with the nucleic acid encoding the modified fibroin according to the present invention and encoding a modified fibroin including a domain sequence represented by Formula 1: $[(A)_n$ motif-$REP]_m$, or Formula 2: $[(A)_n$ motif-$REP]_m$–$(A)_n$ motif. The modified fibroin encoded by the nucleic acid preferably has the glutamine residue content rate of 9% or less. In addition, the modified fibroin encoded by the nucleic acid preferably has the GPGXX motif content rate of 10% or more.

[Host and Expression Vector]

An expression vector according to the present invention has a nucleic acid sequence according to the present invention and one or a plurality of regulatory sequences operably linked thereto. The regulatory sequence is a sequence (for example, a promoter, an enhancer, a ribosome binding sequence, or a transcription termination sequence) that controls the expression of a recombinant protein in a host, and can be appropriately selected depending on the type of the host. The type of the expression vector such as a plasmid vector, a viral vector, a cosmid vector, a fosmid vector, or an artificial chromosome vector can be appropriately selected depending on the type of the host.

The host according to the present invention is a host which has been transformed with the expression vector according to the present invention. Both prokaryotes and eukaryotes such as yeast, filamentous fungi, insect cells, animal cells, and plant cells can be suitably used as hosts.

As the expression vector, an expression vector which can autonomously replicate in a host cell or can be incorporated into a chromosome of a host and which contains a promoter at a position capable of transcribing the nucleic acid according to the present invention is suitably used.

In a case where a prokaryote such as a bacterium is used as a host, the expression vector according to the present invention is preferably a vector which is capable of autonomous replication in the prokaryote and at the same time includes a promoter, a ribosome binding sequence, a nucleic acid according to the present invention and a transcription termination sequence. A gene that controls a promoter may be included.

Examples of the prokaryote include microorganisms belonging to the genus *Escherichia, Brevibacillus, Serratia, Bacillus, Microbacterium, Brevibacterium, Corynebacterium* and *Pseudomonas*.

Examples of microorganisms belonging to the genus *Escherichia* include *Escherichia coli* BL21 (Novagen, Inc.), *Escherichia coli* BL21 (DE3) (Life Technologies Corporation), *Escherichia coli* BLR (DE3) (Merck KGaA), *Escheri-* chia coli Dill, *Escherichia coli* GI698, *Escherichia coli* HB101, *Escherichia coli* JM109, *Escherichia coli* KS (ATCC 23506), *Escherichia coli* KY3276, *Escherichia coli* MC1000, *Escherichia coli* MG1655 (ATCC 47076), *Escherichia coli* No. 49, *Escherichia coli* Rosetta (DE3) (Novagen, Inc.), *Escherichia coli* TB1, *Escherichia coli* Tuner (Novagen, Inc.), *Escherichia coli* Tuner (DE3) (Novagen, Inc.), *Escherichia coli* W1485, *Escherichia coli* W3110 (ATCC 27325), *Escherichia coli* XL1-Blue, and *Escherichia coli* XL2-Blue.

Examples of microorganisms belonging to the genus *Brevibacillus* include *Brevibacillus agri*, *Brevibacillus borstelensis*, *Brevibacillus centrosporus*, *Brevibacillus fomijiosus*, *Brevibacillus invocatus*, *Brevibacillus laterosporus*, *Brevibacillus limnophilus*, *Brevibacillus parabrevis*, *Brevibacillus reuszeri*, *Brevibacillus thermoruber*, *Brevibacillus brevis* 47 (FERM BP-1223), *Brevibacillus brevis* 47K (FERM BP-2308), *Brevibacillus brevis* 47-5 (FERM BP-1664), *Brevibacillus brevis* 47-5Q (JCM 8975), *Brevibacillus choshinensis* HPD31 (FERM BP-1087), *Brevibacillus choshinensis* HPD31-S (FERM BP-6623), *Brevibacillus choshinensis* 1-1PD31-OK (FERM BP-4573), and *Brevibacillus choshinensis* SP3 strain (manufactured by Takara Bio, Inc.).

Examples of microorganisms belonging to the genus *Serratia* include *Serratia liquefacience* ATCC 14460, *Serratia entomophila*, *Serratia ficaria*, *Serratia fonticola*, *Serratia grimesii*, *Serratia proteamaculans*, *Serratia odorifera*, *Serratia plymuthica*, and *Serratia rubidaea*.

Examples of microorganisms belonging to the genus *Bacillus* include *Bacillus subtilis* and *Bacillus amyloliquefaciens*.

Examples of microorganisms belonging to the genus *Microbacterium* include *Microbacterium* ammoniaphilum ATCC 15354.

Examples of microorganisms belonging to the genus *Brevibacterium* include *Brevibacterium divaricatum* (*Corynebacterium glutamicum*) ATCC 14020, *Brevibacterium flavum* (*Corynebacterium glutamicum* ATCC 14067) ATCC 13826, ATCC 14067, *Brevibacterium immariophilum* ATCC 14068, *Brevibacterium lactofermentum* (*Corynebacterium glutamicum* ATCC 13869) ATCC 13665, ATCC 13869, *Brevibacterium roseum* ATCC 13825, *Brevibacterium saccharolyticum* ATCC 14066, *Brevibacterium tiogenitalis* ATCC 19240, *Brevibacterium album* ATCC 15111, and *Brevibacterium cerinum* ATCC 15112.

Examples of microorganisms belonging to the genus *Corynebacterium* include *Corynebacterium ammoniagenes* ATCC 6871, ATCC 6872, *Corynebacterium glutamicum* ATCC 13032, *Corynebacterium glutamicum* ATCC 14067, *Corynebacterium acetoacidophilum* ATCC 13870, *Corynebacterium acetoglutamicum* ATCC 15806, *Corynebacterium alkanolyticum* ATCC 21511, *Corynebacterium callunae* ATCC 15991, *Corynebacterium glutamicum* ATCC 13020, ATCC 13032, ATCC 13060, *Corynebacterium lilium* ATCC 15990, *Corynebacterium melassecola* ATCC 17965, *Corynebacterium thermoaminogenes* AJ12340 (FERM BP-1539), and *Corynebacterium herculis* ATCC 13868.

Examples of microorganisms belonging to the genus *Pseudomonas* include *Pseudomonas putida*, *Pseudomonas fluorescens*, *Pseudomonas brassicacearum*, *Pseudomonas fulva*, and *Pseudomonas* sp. D-0110.

As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], a protoplast method (Japanese Unexamined Patent Publication No. S63-248394), or a method described in Gene, 17, 107 (1982) or Molecular & General Genetics, 168, 111 (1979).

Transformation of microorganisms belonging to the genus *Brevibacillus* can be carried out, for example, by the method of Takahashi et al. (J. Bacteriol., 1983, 156: 1130-1134), the method of Takagi et al. (Agric. Biol. Chem., 1989, 53: 3099-3100), or the method of Okamoto et al. (Biosci. Biotechnol. Biochem., 1997, 61: 202-203).

Examples of the vector into which the nucleic acid according to the present invention is introduced (hereinafter, simply referred to as "vector") include pBTrp2, pBTac1, and pBTac2 (all commercially available from Boehringer Mannheim GmbH), pKK233-2 (manufactured by Pharmacia Corporation), pSE280 (manufactured by Invitrogen Corporation), pGEMEX-1 (manufactured by Promega Corporation), pQE-8 (manufactured by QIAGEN Corporation), pKYP10 (Japanese Unexamined Patent Publication No. S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(-) (manufactured by Stratagene Corporation), pTrs30 [constructed from *Escherichia coli* JM109/pTrS30 (FERM BP-5407)], pTrs32 [constructed from *Escherichia coli* JMI109/pTrS32 (FEW BP-5408)], pGHA2 [constructed from *Escherichia coli* IGHA2 (FERM B-400), Japanese Unexamined Patent Publication No. S60-221091], pGKA2 [constructed from *Escherichia coli* IGKA 2 (FERM BP-6798), Japanese Unexamined Patent Publication No. 60-221091], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (manufactured by Pharmacia Corporation), and pET systems (manufactured by Novagen, Inc.).

In the case where *Escherichia coli* is used as a host, pUC18, pBluescriptII, pSupex, pET22b, pCold, or the like can be mentioned as a suitable vector.

Specific examples of vectors suitable for microorganisms belonging to the genus *Brevibacillus* include pUB110 or pHY500 (Japanese Unexamined Patent Publication No. H2-31682), pNY700 (Japanese Unexamined Patent Publication No. H4-278091), pHY4831 (J. Bacteriol., 1987, 1239-1245), pNU200 (UDAKA Shigezou, Journal of the Agricultural Chemical Society of Japan, 1987, 61: 669-676), pNU100 (Appl. Microbiol. Biotechnol., 1989, 30: 75-80), pNU211 (J. Biochem., 1992, 112: 488-491), pNU211R2L5 (Japanese Unexamined Patent Publication No. H7-170984), pNH301 (Appl. Environ. Microbiol., 1992, 58: 525-531), pNH326, pNH400 (J. Bacteriol., 1995, 177: 745-749), and pHT210 (Japanese Unexamined Patent Publication No. 116-133782), pHT110R2L5 (Appl. Microbiol. Biotechnol., 1994, 42: 358-363), which are known as *Bacillus subtilis* vectors; and pNCO2 (Japanese Unexamined Patent Publication No. 2002-238569) which is a shuttle vector between *Escherichia coli* and a microorganism belonging to the genus *Brevibacillus*.

The promoter is not limited as long as it functions in a host cell. Examples thereof include promoters derived from *Escherichia coli* or phage such as a trp promoter (Ptrp), a lac promoter, a PL promoter, a PR promoter, and a T7 promoter. Also, promoters artificially designed and modified, such as a promoter (Ptrp×2) in which two Ptrps are connected in series, a tac promoter, a lacT7 promoter, and a let I promoter, can also be used.

It is preferable to use a plasmid in which the distance between the Shine-Dalgarno sequence, which is a ribosome binding sequence, and the initiation codon is adjusted to an appropriate distance (for example, 6 to 18 bases). In the expression vector according to the present invention, a transcription termination sequence is not necessarily required for the expression of the nucleic acid according to the present invention, but it is preferable to arrange a transcription termination sequence immediately below a structural gene.

Examples of eukaryotic hosts include yeast, filamentous fungi (mold and the like), and insect cells.

Examples of the yeast include yeasts belonging to the genus *Saccharomyces, Schizosaccharomyces, Kluyveromyces, Trichosporon, Schwanniomyces, Pichia, Candida, Yarrowia, Hansenula*, and the like. More specific examples of the yeast include *Saccharomyces cerevisiae, Schizosaccharornyces pombe, Kluyveromyces lactis, Kluyveromyces marxianus, Trichosporon pullulans, Schwanniomyces alluvius, Schwanniomyces occidentalis, Candida utilis, Pichia pastoris, Pichia angusta, Pichia methanolica, Pichia polymorpha, Pichia stipitis, Yarrowia lipolytica*, and *Hansenula polymorpha*.

It is preferable that the expression vector in the case where yeast is used as a host cell usually include an origin of replication (in the case where amplification in a host is required), a selection marker for propagation of the vector in *Escherichia coli*, a promoter and a terminator for recombinant protein expression in yeast, and a selection marker for yeast.

In the case where the expression vector is a non-integrating vector, it is preferable to further include an autonomously replicating sequence (ARS). This makes it possible to improve the stability of the expression vectors in cells (Myers, A. M., et al. (1986) Gene 45: 299-310).

Examples of the vector in the case where yeast is used as a host include YEP13 (ATCC 37115), YEp24 (ATCC 37051), YCp50 (ATCC 37419), YIp, pHS19, pHS15, pA0804, pHIL3Ol, pHIL-S1, pPIC9K, pPICZα, pGAPZα, and pPICZ B.

The promoter is not limited as long as it can be expressed in yeast. Examples of the promoter include a promoter of glycolytic genes such as hexose kinase, a PHO5 promoter, a PGK promoter, a GAP promoter, an ADH promoter, a gal 1 promoter, a gal 10 promoter, a heat shock polypeptide promoter, an MFα1 promoter, a CUP 1 promoter, a pGAP promoter, a pGCW14 promoter, an AOX1 promoter, and an MOX promoter.

As a method for introducing an expression vector into yeast, any method can be used as long as it introduces DNA into yeast. Examples thereof include an electroporation method (Methods Enzymol., 194, 182 (1990)), a spheroplast method (Proc. Natl. Acad. Sci., USA, 81, 4889 (1984)), a lithium acetate method (J. Bacteriol., 153, 163 (1983)), and a method described in Proc. Natl. Acad. Sci. USA, 75, 1929 (1978).

Examples of filamentous fungi include fungi belonging to the genus *Acremonium, Aspergillus, Ustilago, Trichodenna, Neurospora, Fusarium, Humicola, Penicillium, Myceliophtora, Botryts, Magnaporthe, Mucor, Metarhizium, Monascus, Rhizopus*, and *Rhizomucor*.

Specific examples of filamentous fungi include *Acremonium alabamense, Acremonium cellulolyticus, Aspergillus aculeatus, Aspergillus awamori, Aspergillus oryzae, Aspergillus sake, Aspergillus sojae, Aspergillus tubigensis, Aspergillus niger, Aspergillus nidulans, Aspergillus parasiticus, Aspergillus ficuum, Aspergillus phoeicus, Aspergillus foetidus, Aspergillus flavus, Aspergillus fumigatus, Aspergillus japonicus, Trichoderma viride, Trichoderma harzianum, Trichoderma reseei, Chrysosporium lucknowense, Thermoascus, Sporotrichum, Sporotrichum cellulophilum, Talaromyces, Thielavia terrestris, Thielavia, Neurospora crassa, Fusarium oxysporus, Fusarium graminearum, Fusarium venenatum, Humicola insolens, Penicillium chrysogenum, Penicillium camemberti, Penicillium canescens, Penicillium emersonii, Penicillium funiculosum, Penicillium griseoroseum, Penicillium purpurogenum, Penicillium roqueforti, Myceliophtaora thermophilum, Mucor ambiguus, Mucor circinelloides, Mucor fragilis, Mucor hiemalis, Mucor inaequisporus, Mucor oblongiellipticus, Mucor racemosus, Mucor recurvus, Mocor saturninus, Mocor subtilissmus, Ogatac a polymorpha, Phanerochaete chrysosporium, Rhizomucor miehei, Rhizomucor pusillus*, and *Rhizopus arrhizus*.

The promoter in the case where the host is a filamentous fungus may be any one of a gene related to a glycolytic system, a gene related to constitutive expression, an enzyme gene related to hydrolysis, and the like. Specific examples thereof include amyB, glaA, agdA, glaB, TEF1, xynF1 tannase gene, No. 8AN, gpdA, pgkA, enoA, *melO*, sodM, catA, and catB.

Introduction of the expression vector into filamentous fungi can be carried out by a conventionally known method Examples thereof include the method of Cohen et al. (calcium chloride method) [Proc. Natl. Acad. Sci. USA, 69: 2110 (1972)], a protoplast method [Mol. Gen. Genet., 168: 111 (1979)], a competent method [J. Mol. Biol., 56: 209 (1971)], and an electroporation method.

Insect cells include, for example, lepidopteran insect cells, more specifically insect cells derived from *Spodoptera frugiperda* such as Sf9 and Sf21, and insect cells derived from *Trichoplusia ni* such as High 5.

Examples of the vector in the case where an insect cell is used as a host include baculoviruses such as *Autographa californica* nuclear polyhedrosis virus which is a virus that infects insects belonging to the family Noctuidae (Baculovirus Expression Vectors, A Laboratory Manual, W. H. Freeman and Company, New York (1992)).

In the case where an insect cell is used as a host, a polypeptide can be expressed by the method described in, for example, Current Protocols in Molecular Biology, Baculovirus Expression Vectors, A Laboratory Manual, W. H. Freeman and Company, New York (1992), or Bio/Technology, 6, 47 (1988). That is, a recombinant gene transfer vector and a baculovirus are co-introduced into an insect cell to obtain a recombinant virus (expression vector) in an insect cell culture supernatant, and then the recombinant virus is further infected into an insect cell, whereby the polypeptide can be expressed. Examples of the gene transfer vector used in the above method include pVL1392, pVL1393, and pBlueBacIII (all manufactured by Invitorogen Corporation).

As a method for co-introducing a recombinant gene transfer vector and a baculovirus into an insect cell for constructing the recombinant virus, for example, a calcium phosphate method (Japanese Unexamined Patent Publication No. H2-227075), a lipofection method (Proc. Natl. Acad. Sci. USA, 84, 7413 (1987)), or the like can be mentioned.

The recombinant vector according to the present invention preferably further contains a selection marker gene for selecting a transformant. For example, in *Escherichia coli*, resistance genes for various drugs such as tetracycline, ampicillin, and kanamycin can be used as selection marker genes. A recessive selection marker capable of complementing a genetic mutation involved in auxotrophy can also be used. In yeast, a resistance gene for geneticin can be used as a selection marker gene, and a gene complementing a genetic mutation involved in auxotrophy, or a selection marker such as LEU2, URA3, TRP1, or HIS3 can also be used. Examples of the selection marker gene for filamentous fungi include a marker gene selected from the group consisting of niaD (Biosci. Biotechnol. Biochem., 59, 1795-1797 (1995)), argB (Enzyme Microbiol Technol, 6, 386-389, (1984)), sC (Gene, 84, 329-334, (1989)), ptrA (BiosciBiotechnol Biochem, 64, 1416-1421, (2000)), pyrG (Biochem-Biophys Res Commun, 112, 284-289, (1983)), amdS (Gene, 26, 205-221, (1983)), aureobasidin resistance gene (Mol Gen Genet, 261, 290-296, (1999)), benomyl resistance gene (Proc Natl Acad Sci USA, 83, 4869-4873, (1986)) and hygromycin resistance gene (Gene, 57, 21-26, (1987)), and a leucine auxotrophy-complementing gene. Further, in the case where the host is an auxotrophic mutant strain, a wild-type gene complementing the auxotrophy can also be used as a selection marker gene.

The selection of the host transformed with the expression vector according to the present invention can be carried out by plaque hybridization and colony hybridization using a probe that selectively binds to the nucleic acid according to the present invention. As the probe, it is possible to use a probe obtained by modifying a partial DNA fragment amplified by a PCR method based on sequence information of the nucleic acid according to the present invention with a radioisotope or digoxigenin.

(Production of Modified Fibroin)

In the host transformed with the expression vector according to the present invention, the modified fibroin according to the present invention can be produced by expressing the nucleic acid according to the present invention. As for the expression method, secretory production, fusion protein expression, or the like, in addition to direct expression, can be carried out according to the method described in Molecular Cloning, 2nd edition. In the case where it is expressed by yeast, an animal cell, or an insect cell, a modified fibroin can be obtained as a polypeptide to which a sugar or sugar chain is added.

The modified fibroin according to the present invention can be produced, for example, by culturing a host transformed with the expression vector according to the present invention in a culture medium, producing and accumulating the modified fibroin according to the present invention in the culture medium, and then collecting the modified fibroin from the culture medium. The method for culturing the host according to the present invention in a culture medium can be carried out according to a method commonly used for culturing a host.

In the case where the host according to the present invention is a prokaryote such as Escherichia coli or a eukaryote such as yeast, any of a natural medium and a synthetic medium may be used as a culture medium of the host according to the present invention as long as it contains a carbon source, a nitrogen source, inorganic salts and the like which can be assimilated by the host and it is capable of efficiently culturing the host.

As the carbon source, any carbon source that can be assimilated by the host may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol.

Examples of the nitrogen source that can be used include ammonium salts of inorganic or organic acids such as ammonia, ammonium chloride, ammonium sulfate, ammonium acetate and ammonium phosphate, other nitrogen-containing compounds, peptone, meat extract, yeast extract, corn steep liquor, casein hydrolyzate, soybean cake and soybean cake hydrolyzate, various fermented microbial cells and digested products thereof.

Examples of the inorganic salt that can be used include potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as Escherichia coli or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

As a culture medium for insect cells, commonly used TNM-FH medium (manufactured by Pharmingen Inc.), Sf-900 II SFM medium (manufactured by Life Technologies Corporation), ExCell 400 and ExCell 405 (both manufactured by JRH Biosciences Inc.), Grace's Insect Medium (Nature, 195, 788 (1962)), and the like can be used.

Culture of insect cells can be carried out, for example, for a culture time of 1 to 5 days under conditions such as pH 6 to 7 of culture medium and culture temperature 25° C. to 30° C. In addition, an antibiotic such as gentamicin may be added to the culture medium as necessary during the culture.

In the case where the host is a plant cell, the transformed plant cell may be directly cultured, or it may be differentiated into a plant organ and then cultured. As the culture medium for culturing a plant cell, for example, commonly used Murashige and Skoog (MS) medium, White medium, or a medium in which a plant hormone such as auxin or cytokinin is added to these media can be used.

Culture of animal cells can be carried out, for example, for a culture time of 3 to 60 days under conditions such as pH 5 to 9 of the culture medium and culture temperature 20° C. to 40° C. In addition, an antibiotic such as kanamycin or hygromycin may be added to the medium as necessary during the culture.

As a method for producing a modified fibroin using a host transformed with the expression vector according to the present invention, there are a method for producing the modified fibroin in a host cell, a method for secreting the modified fibroin outside the host cell, and a method for producing the modified fibroin on the outer membrane of the host cell. Each of these methods can be selected depending on the host cell to be used and the structure of the modified fibroin to be produced.

For example, in the case where a modified fibroin is produced in the host cell or on the outer membrane of the host cell, the production method can be altered to actively secrete the modified fibroin outside the host cell according to the method of Paulson et al. (J. Biol. Chem., 264, 17619 (1989)), the method of Lowe et al. (Proc. Natl. Acad. Sci. USA, 86, 8227 (1989), Genes Develop., 4, 1288 (1990)), or the methods described in Japanese Unexamined Patent Publication No. H5-336963, International Publication No. WO 94/23021, and the like. That is, the modified fibroin can be actively secreted outside the host cell by expressing the modified fibroin in a form in which a signal peptide is added to a polypeptide containing an active site of a modified fibroin using a gene recombination technique.

The modified fibroin produced by the host transformed with the expression vector according to the present invention can be isolated and purified by a method commonly used for protein isolation and purification. For example, in the case where the modified fibroin is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), an cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

As the chromatography, column chromatography using phenyl-TOYOPEARL (available from Tosoh Corporation), DEAE-TOYOPEARL (available from Tosoh Corporation), and Sephadex G-150 (available from Pharmacia Biotech Inc.) is preferably used.

In the case where the modified fibroin is expressed by the formation of an insoluble matter in the cell, similarly, the host cells are recovered, disrupted and centrifuged to recover the insoluble matter of the modified fibroin as a precipitated fraction. The recovered insoluble matter of the modified fibroin can be solubilized with a protein denaturing agent. After this operation, a purified preparation of modified fibroin can be obtained by the same isolation and purification method as described above.

In the case where a modified fibroin or a derivative in which a sugar chain has been added to the modified fibroin is secreted extracellularly, the modified fibroin or the derivative thereof can be recovered from the culture supernatant. That is, a culture supernatant is obtained by treating the culture by a technique such as centrifugation, and a purified preparation can be obtained from the culture supernatant by using the same isolation and purification method as described above.

[Spinning]

The modified fibroin according to the present invention can be produced and purified as described above, and then spun by a method usually used for spinning fibroin. For example, a fiber framed with the modified fibroin according to the present invention can be obtained by spinning a spinning liquid (doping liquid) in which the modified fibroin according to the present invention is dissolved in a solvent.

The spinning liquid is prepared by adding a solvent to the modified fibroin and adjusting the viscosity thereof to allow spinning. Any solvent may be used as long as it can dissolve the modified fibroin. Examples of the solvent include an aqueous solution or the like, containing hexafluoroisopropanol (HFIP), hexafluoroacetone (HFA), dimethylsulfoxide (DMSO), N,N-dimethylformamide (DMF), formic acid, urea, guanidine, sodium dodecylsulfate (SDS), lithium bromide, calcium chloride, and lithium thiocyanate.

An inorganic salt may be added to the spinning liquid as necessary. The inorganic salts include, for example, inorganic salts consisting of the following Lewis acids and Lewis bases. Examples of the Lewis base include an oxo acid ion (such as a nitrate ion and a perchlorate ion), a metal oxo acid ion (such as a permanganate ion), a halide ion, a thiocyanate ion, a cyanate ion, and the like. Examples of the Lewis acid include a metal ions such as an alkali metal ion and an alkaline earth metal ion, a polyatomic ion such as an ammonium ion, and a complex ion. Specific examples of the inorganic salts consisting of a Lewis acid and a Lewis base include: lithium salts such as lithium chloride, lithium bromide, lithium iodide, lithium nitrate, lithium perchlorate, and lithium thiocyanate; calcium salts such as calcium chloride, calcium bromide, calcium iodide, calcium nitrate, calcium perchlorate and calcium thiocyanate; iron salts such as iron chloride, iron bromide, iron iodide, iron nitrate, iron perchlorate and iron thiocyanate; aluminum salts such as aluminum chloride, aluminum bromide, aluminum iodide, aluminum nitrate, aluminum perchlorate, and aluminum thiocyanate; potassium salts such as potassium chloride, potassium bromide, potassium iodide, potassium nitrate, potassium perchlorate, and potassium thiocyanate; sodium salts such as sodium chloride, sodium bromide, sodium iodide, sodium nitrate, sodium perchlorate and sodium thiocyanate; zinc salts such as zinc chloride, zinc bromide, zinc iodide, zinc nitrate, zinc perchlorate and zinc thiocyanate, chloride; magnesium salts such as magnesium chloride, magnesium bromide, magnesium iodide, magnesium nitrate, magnesium perchlorate, and magnesium thiocyanate; barium salts such as barium chloride, barium bromide, barium iodide, barium nitrate, barium perchlorate, and barium thiocyanate; and strontium salts such as strontium chloride, strontium bromide, strontium iodide, strontium nitrate, strontium perchlorate, and strontium thiocyanate.

The viscosity of the spinning liquid may be suitably set according to the spinning method and can be, for example, 100 to 15,000 cP (centipoise) at 35° C. The viscosity of the spinning liquid can be measured using, for example, a "EMS viscometer" (trade name) manufactured by Kyoto Electronics Manufacturing Co., Ltd.

The spinning method is not particularly limited as long as it is a method capable of spinning the modified fibroin according to the present invention, and examples thereof include dry-type spinning, melt spinning, and wet-type spinning A preferred spinning method is wet-type spinning.

In wet-type spinning, an undrawn yarn with the shape of yarn can be obtained by extruding, from a spinneret (nozzle), a solvent in which a modified fibroin is dissolved into a coagulation liquid (coagulation liquid bath) in which the modified fibroin is solidified. The coagulation liquid may be any solution that can be desolvated, and examples thereof include lower alcohols having 1 to 5 carbon atoms such as methanol, ethanol and 2-propanol, and acetone. Water may be appropriately added to the coagulation liquid. The temperature of the coagulation liquid is preferably 0° C. to 30° C. In a case where a syringe pump having a nozzle with a diameter of 0.1 to 0.6 mm is used as the spinneret, the extrusion speed is preferably 0.2 to 6.0 ml/hour per hole and more preferably 1.4 to 4.0 ml/hour. The length of the coagulation liquid bath is not limited as long as the desolvation can be efficiently carried out, and is, for example, 200 to 500 mm. The withdrawing speed of the undrawn yarn may be, for example, 1 to 20 m/min and preferably 1 to 3 m/min. The residence time may be, for example, 0.01 to 3 minutes and preferably 0.05 to 0.15 minutes. In addition, drawing (pre-drawing) may be performed in the coagulation liquid. In order to suppress evaporation of the lower alcohol, the coagulation liquid may be kept at a low temperature, and yarn may be withdrawn in an undrawn state. The coagulation liquid bath may be provided in multiple stages, and the drawing may be performed in each stage or in a specific stage as necessary.

The undrawn yarn (or pre-drawn yarn) obtained by the above-described method can be made into a drawn yarn (fibroin fiber) through a drawing step. Examples of the drawing method include wet heat drawing and dry heat drawing.

The wet heat drawing can be performed in warm water, in a solution obtained by adding an organic solvent or the like to warm water, or in heated steam. The temperature may be, for example, 50° C. to 90° C. and preferably 75° C. to 85° C. In the wet heat drawing, the undrawn yarn (or pre-drawn yarn) can be drawn, for example, by 1 to 10 times and preferably by 2 to 8 times.

The dry heat drawing can be performed using an electric tubular furnace, a dry heat plate, or the like. The temperature may be, for example, 140° C. to 270° C. and preferably 160° C. to 230° C. In the dry heat drawing, the undrawn yarn (or pre-drawn yarn) can be drawn, for example, by 0.5 to 8 times and preferably by 1 to 4 times.

The wet heat drawing and the dry heat drawing may be performed independently or in combination, or may be performed in multiple stages. That is, the wet heat drawing and the dry heat drawing can be performed in suitable combination, for example, in a manner in which a first stage drawing is performed by wet heat drawing and a second stage drawing is performed by dry heat drawing, or in a manner in which the first stage drawing is performed by wet heat drawing, the second stage drawing is performed by wet heat drawing, and a third stage drawing is performed by dry heat drawing.

The final drawing ratio in the drawing step is, for example, 5 to 20 times and preferably 6 to 11 times with respect to the undrawn yarn (or pre-drawn yarn).

The modified fibroin according to the present invention may be drawn into a fibroin fiber and then chemically crosslinked between polypeptide molecules in the fibroin fiber. Examples of functional groups that can be crosslinked include an amino group, a carboxyl group, a thiol groups, and a hydroxy group. For example, an amino group of a lysine side chain contained in the polypeptide can be crosslinked through an amide bond by dehydration condensation with a carboxyl group of a glutamic acid or aspartic acid side chain. The crosslinking may be performed by performing a dehydration condensation reaction under vacuum heating, or by a dehydration condensation agent such as carbodiimides.

The crosslinking between polypeptide molecules may be performed using a crosslinking agent such as carbodiimides or glutaraldehyde, or may be performed using an enzyme such as transglutaminase. Carbodiimides are compounds represented by the general formula $R_1N=C=NR_2$ (where $R_1$ and $R_2$ each independently represent an organic group containing an alkyl group having 1 to 6 carbon atoms or a cycloalkyl group). Specific examples of carbodiimides include 1-ethyl-3-(3-dimethylaminopropyl) carbodiimide hydrochloride (EDC), N,N'-dicyclohexylcarbodiimide (DCC), 1-cyclohexyl-3-(2-morpholinoethyl) carbodiimide, and diisopropyl carbodiimide (DIC). Among these, EDC and DIC are preferable because they have a high ability to form an amide bond between polypeptide molecules and easily perform a crosslinking reaction.

The crosslinking treatment is preferably performed by applying a crosslinking agent to the fibroin fiber and performing crosslinking with vacuum heating and drying. As the crosslinking agent, a pure product may be applied to the fibroin fiber, or a product diluted with a lower alcohol having 1 to 5 carbon atoms, a buffer solution, or the like to a concentration of 0.005 to 10 mass % may be applied to the fibroin fiber. The crosslinking treatment is preferably performed at a temperature of 20° C. to 45° C. for 3 to 42 hours. Higher stress (strength) can be imparted to the fibroin fiber by the crosslinking treatment.

[Evaluation of Shrinkability of Fibroin Fiber]

Figure 2:
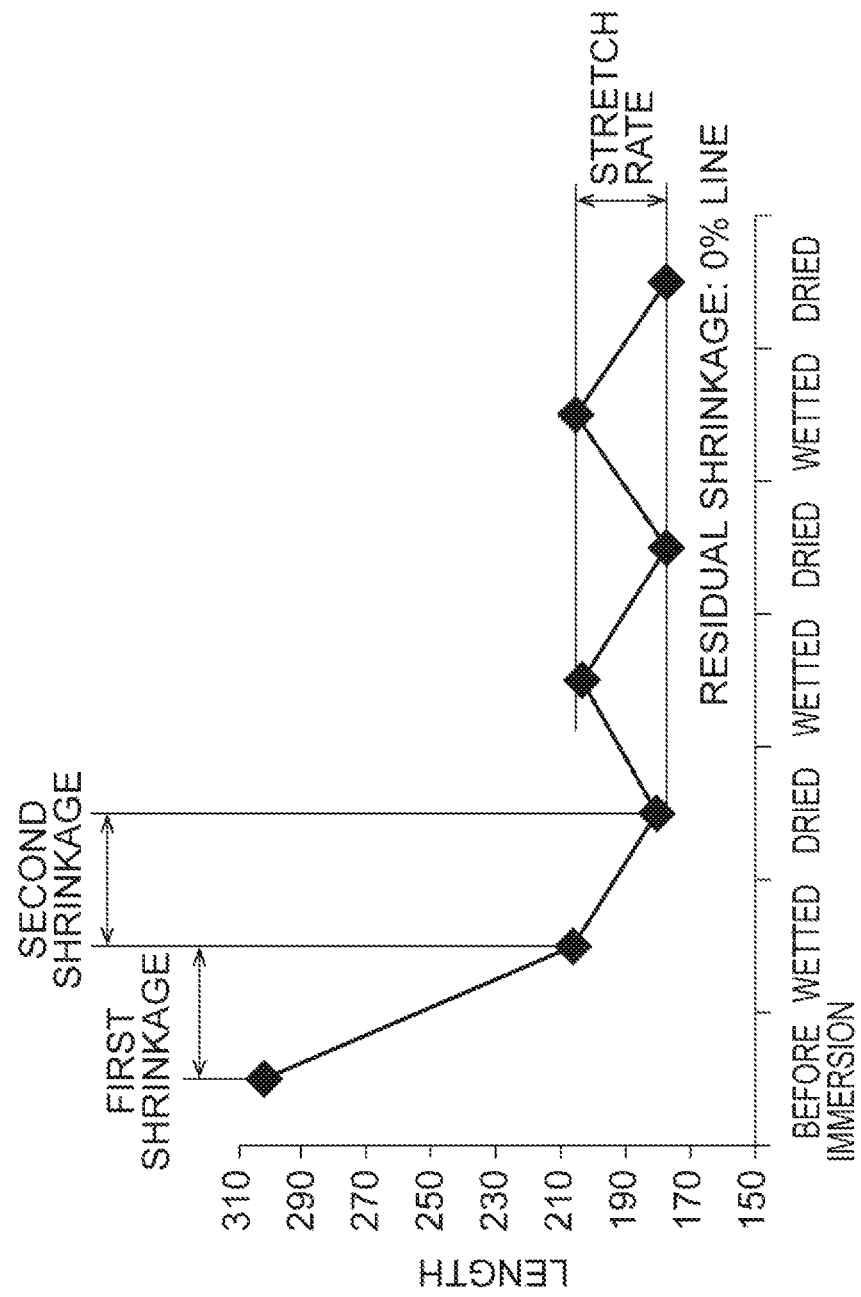

FIG. 2 is a graph showing an example of a change in the length of a fibroin fiber due to contact with water or the like. The fibroin fiber has the property of shrinking (first shrinkage) by contact (wetting) with water below the boiling point. After first shrinkage, the fibroin fiber further shrinks when dried (second shrinkage). After second shrinkage, the fibroin fiber swells again to the length before second shrinkage by contact with water below the boiling point, and then repeats shrinkage and swelling in a length range ("stretch rate" in FIG. 2) similar to the length range in second shrinkage in a case of subsequently repeating drying and wetting (FIG. 2). For the fibroin fiber, the smaller the shrinkage is, the better it is. In particular, in a product such as a fabric made of fibroin fiber, it is preferable that this second shrinkage is small.

Second shrinkage can be evaluated using a second shrinkage rate obtained by the following method as an index.

<Second Shrinkage Rate>

A plurality of fibroin fibers having a length of about 30 cm are bundled to form a fiber bundle having a fineness of 150 denier. With 0.8 g of lead weight being attached to this fiber bundle, the fiber bundle is immersed in water at 40° C. for 10 minutes to cause first shrinkage, and the length of the fiber bundle is measured in water.

The fiber bundle shrunk by first shrinkage is taken out of water and dried at room temperature for 2 hours with 0.8 g of lead weight attached. After drying, the length of the fiber bundle is measured. Again, wetting and drying are repeated at least three times, and an average length when wetted (Lwet) and an average length when dried (Ldry) are determined. The second shrinkage rate is calculated according to the following expression.

$$\text{second shrinkage rate } (\%) = (1-(L\text{dry}/L\text{wet}))*100 \quad \text{Expression:}$$

A fibroin fiber spun out of naturally occurring fibroin usually has a second shrinkage rate of 11% to 20%, whereas the fibroin fiber spun out of the modified fibroin according to the present invention can have a reduced second shrinkage rate of 8% or less.

[Film]

The film according to the present invention can be obtained by preparing a doping liquid in which the modified fibroin according to the present invention is dissolved in a solvent, cast-molding the doping liquid on the surface of a base material, and drying and/or desolvation.

Examples of the solvent include the same solvents as those exemplified for the spinning liquid (doping liquid). The solvent is preferably a polar solvent such as formic acid, hexafluoro-2-propanol (HFIP), or dimethyl sulfoxide. An inorganic salt may be added to the doping liquid as necessary. Examples of the inorganic salt include the same inorganic salts as those exemplified for the spinning liquid (doping liquid).

The viscosity of the doping liquid is preferably 15 to 80 cP (centipoise) and more preferably 20 to 70 cP.

The concentration of the modified fibroin according to the present invention is preferably 3 to 50 mass %, more preferably 3.5 to 35 mass %, and still more preferably 4.2 to 15.8 mass % in a case where the doping liquid is set to 100 mass %.

When preparing the doping liquid, heating may be performed at 30° C. to 60° C. Shaking and stirring may be performed to promote dissolution.

The base material may be a resin substrate, a glass substrate, a metal substrate, or the like. The base material is preferably a resin substrate from the viewpoint that the film after cast-molding can be easily peeled off. The resin substrate may be, for example, a polyethylene terephthalate (PET) film, a fluororesin film such as polytetrafluoroethylene, a polypropylene (PP) film, or a release film in which a silicone compound is immobilized on the surface of these films. It is more preferable that the base material is stable with respect to solvent such as HFIP and DMSO, is stably cast-molded with the doping liquid, and from the viewpoint that the film after molding can be easily peeled off is a release film in which the silicone compound is immobilized in the PET film or on the surface of the PET film.

The specific procedure is as follows. First, the doping liquid is cast on the surface of the base material, and a wet film having a predetermined thickness (for example, a thickness of 1 to 1,000 μm after drying and/or desolvation) is produced using a film thickness control means such as an applicator, a knife coater, and a bar coater.

Drying and/or desolvation can be performed by a dry-type method and/or by a wet-type method. Examples of the dry-type method include vacuum drying, hot air drying, and air drying. Examples of the wet-type method include a method in which a cast film is immersed in a desolvation liquid (also referred to as a coagulation liquid) to remove the solvent. Examples of the desolvation liquid include water, alcohol liquids such as lower alcohols having 1 to 5 carbon atoms including methanol, ethanol, and 2-propanol, and a mixed liquid of water and the alcohol. The temperature of the desolvation liquid (coagulation liquid) is preferably 0° C. to 90° C.

The unstretched film after drying and/or desolvation can be uniaxially or biaxially stretched in water. Biaxial stretching may be sequential stretching or simultaneous biaxial stretching. Multi-stage stretching of two or more stages may be performed. The stretching ratio is preferably 1.01 to 6 times and more preferably 1.05 to 4 times both in length and width. Within this range, it is easy to balance stress with strain. The stretching in water is preferably performed at a water temperature of 20° C. to 90° C. The stretched film is preferably heat-fixed by a dry heat of 50° C. to 200° C. for 5 to 600 seconds. This heat-fixing provides dimensional stability to the film at room temperature. A uniaxially stretched film becomes a uniaxially aligned film, and a biaxially stretched film becomes a biaxially aligned film.

[Evaluation of Waterproofness of Film]

The waterproofness of the film can be evaluated by measuring the degree of moisture absorption under high humidity using a saturated salt method using a saturated aqueous solution of salts.

Examples of the salts include potassium sulfate, potassium chloride, sodium chloride, sodium bromide, potassium carbonate, and magnesium chloride.

The waterproofness of the film can be evaluated by, for example, placing a film cut to a suitable size so that the film does not get immersed in the aqueous solution in an airtight container such as a Falcon tube containing a saturated aqueous solution of potassium sulfate, and, for example, leaving the film for 20 to 48 hours in air equilibrated in high humidity such as relative humidity of 98%, and by measuring the weight and the moisture content of the film to determine the moisture content rate from the moisture content per weight.

[Product]

The fibroin fiber formed of the modified fibroin according to the present invention can be applied to a woven fabric, a knitted fabric, a braided fabric, a non-woven fabric, and the like, as a fiber (such as a long fiber, a short fiber, a multifilament, and a monofilament) or a yarn (such as a spun yarn, a twisted yarn, a false twisted yarn, a processed yarn, a blended yarn, and a blended spun yarn). This fibroin fiber can also be applied to high strength applications such as a rope, a surgical suture, a flexible stop for electrical components, and a physiologically active material for implantation (for example, artificial ligament and aortic band).

In addition to the film, the modified fibroin according to the present invention can also be applied to a foam, a grain, a nanofibril, a gel (such as a hydrogel), a resin and equivalents thereof, which can be produced in accordance with the method described in Japanese Unexamined Patent Publication No. 2009-505668, Japanese Patent No. 5678283, Japanese Patent No. 4638735, or the like.

[Artificially Modified Fibroin Fiber]

The artificially modified fibroin fiber according to the present embodiment includes a modified fibroin, which elongates when wetted, and shrinks when dried from the wetted state (corresponds to stretch after "second shrinkage" in FIG. 2).

The modified fibroin in the artificially modified fibroin fiber according to the present embodiment is not limited to the modified fibroin having an amino acid sequence with a reduced content of glutamine residue, as long as it falls within the modified fibroin defined above. The modified fibroin may be a modified silk fibroin (a modified silk protein obtained by modifying an amino acid sequence of a silk protein produced by silkworm) and a modified spider silk fibroin (a modified spider silk protein obtained by modifying an amino acid sequence of a spider silk protein produced by spiders). The modified fibroin is preferably a modified spider silk fibroin. Specific examples of the modified fibroin include: a modified fibroin derived from a large sphincter bookmark silk protein produced in a major ampullate of spider (first modified fibroin); a modified fibroin having a domain sequence with a reduced content of glycine residue (second modified fibroin); a modified fibroin having a domain sequence with a reduced content of $(A)_n$ motif (third modified fibroin); a modified fibroin having a domain sequence with a reduced content of glycine residue and with a reduced content of $(A)_n$ motif (fourth modified fibroin); a modified fibroin having a domain sequence including a region locally having a high hydropathy index (fifth modified fibroin); and a modified fibroin having a domain sequence with a reduced content of glutamine residue (sixth modified fibroin).

The first modified fibroin include a protein including a domain sequence represented by Formula 1: $[(A)_n$ motif-REP$]_m$. In the first modified fibroin, the number of amino acid residues of $(A)_n$ motif is preferably an integer of 3 to 20, more preferably an integer of 4 to 20, still more preferably an integer of 8 to 20, even more preferably an integer of 10 to 20, even further more preferably an integer of 4 to 16, particularly preferably an integer of 8 to 16, and most preferably an integer of 10 to 16. In the first modified fibroin, the number of amino acid residues constituting REP in Formula 1 is preferably 10 to 200 residues, more preferably 10 to 150 residues, and still more preferably 20 to 100 residues, and even more preferably 20 to 75 residues. In the first modified fibroin, the total number of glycine residues, serine residues, and alanine residues contained in the amino acid sequence represented by Formula 1: [(A) n motif-REP]$_m$ is preferably 40% or more, more preferably 60% or more, and still more preferably 70% or more with respect to the total number of amino acid residues.

The first modified fibroin may be a polypeptide including an amino acid sequence unit represented by Formula 1: [(A)n motif-REP]$_m$, and including a C-terminal sequence which is the amino acid sequence set forth in any of SEQ ID NOs: 25 to 27 or a C-terminal sequence which is an amino acid sequence having 90% or more homology with the amino acid sequence set forth in any of SEQ ID NOs: 25 to 27.

The amino acid sequence set forth in SEQ ID NO: 25 is identical to the amino acid sequence consisting of 50 amino acid residues at the C-terminal of the amino acid sequence of ADF3 (GI: 1263287, NCBI). The amino acid sequence set forth in SEQ ID NO: 26 is identical to the amino acid sequence obtained by removing 20 residues from the C-terminal of the amino acid sequence set forth in SEQ ID NO: 25. The amino acid sequence set forth in SEQ ID NO: 27 is identical to the amino acid sequence obtained by removing 29 residues from the C-terminal of the amino acid sequence set forth in SEQ ID NO: 25.

More specific examples of the first modified fibroin can include a modified fibroin including (1-i) the amino acid sequence set forth in SEQ ID NO: 28 (recombinant spider silk protein ADF3KaiLargeNRSH1) and (1-ii) an amino acid sequence having 90% or more sequence identity with the amino acid sequence set forth in SEQ ID NO: 28. The sequence identity is preferably 95% or more.

The amino acid sequence set forth in SEQ ID NO: 28 is an amino acid sequence obtained by approximately doubling repeating regions from the first repeating region to the 13th repeating region and performing mutation such that translation is terminated at the 1154th amino acid residue in an amino acid sequence obtained by adding the amino acid sequence (SEQ ID NO: 29) consisting of a start codon, a His10 tag, and a recognition site for HRV3C protease (human rhinovirus 3C protease) to the N-terminal of ADF3. The C-terminal amino acid sequence of the amino acid sequence set forth in SEQ ID NO: 28 is identical to the amino acid sequence set forth in SEQ ID NO: 27.

The modified fibroin of (1-i) may consist of the amino acid sequence set forth in SEQ ID NO: 28.

The domain sequence of the second modified fibroin has an amino acid sequence with a reduced content of glycine residue, as compared with naturally occurring fibroin. It can be said that the second modified fibroin has an amino acid sequence equivalent to an amino acid sequence in which at least one or a plurality of glycine residues in REP are substituted with other amino acid residues, as compared with naturally occurring fibroin.

The domain sequence of the second modified fibroin may have an amino acid sequence equivalent to an amino acid sequence in which one glycine residue in at least one or the plurality of motif sequences, at least one of which is selected from GGX and GPGXX (where G represents a glycine residue, P represents a proline residue, and X represents an amino acid residue other than glycine) in REP, is substituted with other amino acid residue, as compared with naturally occurring fibroin.

In the second modified fibroin, the proportion of the motif sequences in which the above-described glycine residue is substituted with other amino acid residue may be 10% or more with respect to the entire motif sequences.

The second modified fibroin may include a domain sequence represented by Formula 1: [(A)$_n$ motif-REP]$_m$ and have an amino acid sequence in which z/w is 30% or more, 40% or more, 50% or more, or 50.9% or more, in a case where the total number of amino acid residues in the amino acid sequence consisting of XGX (where X represents an amino acid residue other than glycine) in all REPs in a sequence excluding the sequence from the $(A)_n$ motif located at the most C-terminal side to the C-terminal of the domain sequence from the domain sequence is set as z, and the total number of amino acid residues in the sequence excluding the sequence from the $(A)_n$ motif located at the most C-terminal side to the C-terminal of the domain sequence from the domain sequence is set as w. The number of alanine residues is 83% or more with respect to the total number of amino acid residues in the $(A)_n$ motif, preferably 86% or more, more preferably 90% or more, still more preferably 95% or more, and even still more preferably 100% (which means that the $(A)_n$ motif consists of only alanine residues).

In the second modified fibroin, the content proportion of an amino acid sequence consisting of XGX is preferably increased by substituting one glycine residue in GGX motif with other amino acid residue. In the second modified fibroin, the content proportion of an amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content proportion of an amino acid sequence consisting of GGX in a domain sequence can be calculated by the same method as the method for calculating the content ratio (z/w) of the amino acid sequence consisting of XGX.

In the second modified fibroin, z/w is preferably 50.9% or more, more preferably 56.1% or more, still more preferably 58.7% or more, even still more preferably 70% or more, and still further preferably 80% or more. The upper limit of z/w is not particularly limited, but it may be 95% or less, for example.

The second modified fibroin cab be obtained by, for example, modifying a cloned naturally occurring fibroin gene sequence such that at least a part of a base sequence encoding a glycine residue is substituted with other amino acid residue to encode other amino acid residue. At this time, one glycine residue in GGX motif and GPGXX motif may be selected as the glycine residue to be modified, or may be substituted so that z/w is 50.9% or more. Alternatively, the second modified fibroin according to the present embodiment may also be obtained, for example, by designing an amino acid sequence satisfying the above-described aspect based on the amino acid sequence of naturally occurring fibroin and chemically synthesizing a nucleic acid encoding the designed amino acid sequence. In any case, with respect to the amino acid sequence of naturally occurring fibroin, in addition to the modification equivalent to substitution of glycine residue in REP with other amino acid residue, further modification of amino acid sequence equivalent to substitution, deletion, insertion and/or addition of one or a plurality of amino acid residues may be carried out.

The other amino acid residue described above is not particularly limited as long as it is an amino acid residue other than glycine residue, but is preferably a hydrophobic amino acid residue such as valine (V) residue, leucine (L) residue, isoleucine (I) residue, methionine (M) residue, proline (P) residue, phenylalanine (F) residue, and tryptophan (W) residue, or a hydrophilic amino acid residues such glutamine (Q) residue, asparagine (N) residue, serine (S) residue, lysine (K) residue, and glutamic acid (E) residue, more preferably valine (V) residue, leucine (L) residue, isoleucine (I) residue, phenylalanine (F) residue, and glutamine (Q) residue, and still more preferably glutamine (Q) residue.

More specific examples of the second modified fibroin can include a modified fibroin including (2-i) the amino acid sequence set forth in SEQ ID NO: 30 (Met-PRT380), SEQ ID NO: 31 (Met-PRT410), SEQ ID NO: 32 (Met-PRT525), or SEQ ID NO: 33 (Met-PRT799), and (2-ii) an amino acid sequence having 90% or more sequence identity with the amino acid sequence set forth in SEQ ID NO: 30, SEQ ID NO: 31, SEQ ID NO: 32, or SEQ ID NO: 33.

The modified fibroin of (2-i) will be described. The amino acid sequence set forth in SEQ ID NO: 30 is obtained by substituting all GGXs in REP of the amino acid sequence set forth in SEQ ID NO: 34 (Met-PRT313) equivalent to naturally occurring fibroin with GQX. The amino acid sequence set forth in SEQ ID NO: 31 is obtained by deleting one of every two $(A)_n$ motifs from the N-terminal side to the C-terminal side in the amino acid sequence set forth in SEQ ID NO: 30 and further inserting one $[(A)_n$ motif-REP] just before the C-terminal sequence. The amino acid sequence set forth in SEQ ID NO: 32 is obtained by inserting two alanine residues at the C-terminal side of each $(A)_n$ motif of the amino acid sequence set forth in SEQ ID NO: 31, and further substituting a part of glutamine (Q) residues with serine (S) residues and deleting a part of amino acids on the C-terminal side such that the molecular weight thereof becomes approximately the same as that of SEQ ID NO: 31. The amino acid sequence set forth in SEQ ID NO: 33 is an amino acid sequence obtained by adding a predetermined hinge sequence and a His tag sequence to the C-terminal of a sequence obtained by repeating a region of 20 domain sequences (where several amino acid residues on the C-terminal side of the region are substituted) present in the amino acid sequence set forth in SEQ ID NO: 31 four times.

The value of z/w in the amino acid sequence set forth SEQ ID NO: 34 (equivalent to naturally occurring fibroin) is 46.8%. The values of z/w in the amino acid sequence set forth in SEQ ID NO: 30, the amino acid sequence set forth in SEQ ID NO: 31, the amino acid sequence set forth in SEQ ID NO: 32, and the amino acid sequence set forth in SEQ ID NO: 33 are respectively 58.7%, 70.1%, 66.1%, and 70.0%. In addition, the values of x/y with a Giza ratio (described later) of 1:1.8 to 11.3 in the amino acid sequences set forth in SEQ ID NO: 34, SEQ ID NO: 30, SEQ ID NO: 31, SEQ ID NO: 32 and SEQ ID NO: 33 are respectively 15.0%, 15.0%, 93.4%, 92.7%, and 89.8%.

The modified fibroin of (2-i) may consist of the amino acid sequence set forth in SEQ ID NO: 30, SEQ ID NO: 31, SEQ ID NO: 32, or SEQ ID NO: 33.

The modified fibroin of (2-ii) includes an amino acid sequence having 90% or more sequence identity with the amino acid sequence set forth in SEQ ID NO: 30, SEQ ID NO: 31, SEQ ID NO: 32, or SEQ ID NO: 33. The modified fibroin of (2-ii) is also a protein including a domain sequence represented by Formula 1: $[(A)_n$ motif-REP$]_m$. The sequence identity is preferably 95% or more.

The modified fibroin of (2-ii) preferably has 90% or more sequence identity with the amino acid sequence set forth in SEQ ID NO: 30, SEQ ID NO: 31, SEQ ID NO: 32, or SEQ ID NO: 33, and in a case where the total number of amino acid residues in the amino acid sequence consisting of XGX (where X represents an amino acid residue other than glycine) included in REP is z, and the total number of amino acid residues in REP in the domain sequence is w, z/w is preferably 50.9% or more.

The second modified fibroin may include a tag sequence at either or both of the N-terminal and C-terminal. This makes it possible to isolate, immobilize, detect, and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may include the amino acid sequence set forth in SEQ ID NO: 35 (amino acid sequence including a His tag sequence and a hinge sequence).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) showing antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including a tag sequence may be a modified fibroin including (2-iii) the amino acid sequence set forth in SEQ ID NO: 36 (PRT380), SEQ ID NO: 37 (PRT410), SEQ ID NO: 38 (PRT525), or SEQ ID NO: 39 (PRT799), or (2-iv) an amino acid sequence having 90% or more sequence identity with the amino acid sequence set forth in SEQ ID NO: 36, SEQ ID NO: 37, SEQ ID NO: 38, or SEQ ID NO: 39.

The amino acid sequences set forth in SEQ ID NO: 40 (PRT313), SEQ ID NO: 36, SEQ ID NO: 37, SEQ ID NO: 38, and SEQ ID NO: 39 are respectively amino acid sequences obtained by adding the amino acid sequence (including a His tag sequence and a hinge sequence) set forth in SEQ ID NO: 35 to the N-terminal of the amino acid sequences set forth in SEQ ID NO: 40, SEQ ID NO: 30, SEQ ID NO: 31, SEQ ID NO: 32, and SEQ ID NO: 33.

The modified fibroin of (2-iii) may consist of the amino acid sequence set forth in SEQ ID NO: 36, SEQ ID NO: 37, SEQ ID NO: 38, or SEQ ID NO: 39.

The modified fibroin of (2-iv) includes an amino acid sequence having 90% or more sequence identity with the amino acid sequence set forth in SEQ ID NO: 36, SEQ ID NO: 37, SEQ ID NO: 38, or SEQ ID NO: 39. The modified fibroin of (2-iv) is also a protein including a domain sequence represented by Formula 1: [(A)$_n$ motif-REP]$_m$. The sequence identity is preferably 95% or more.

The modified fibroin of (2-iv) preferably has 90% or more sequence identity with the amino acid sequence set forth in SEQ ID NO: 36, SEQ ID NO: 37, SEQ ID NO: 38, or SEQ ID NO: 39, and in a case where the total number of amino acid residues in the amino acid sequence consisting of XGX (where X represents an amino acid residue other than glycine) included in REP is z, and the total number of amino acid residues in REP in the domain sequence is w, z/w is preferably 50.9% or more.

The second modified fibroin may include a secretory signal for releasing the protein produced in the recombinant protein production system to the outside of a host. The sequence of the secretory signal can be appropriately set depending on the type of the host.

The domain sequence of the third modified fibroin has an amino acid sequence in which the content of (A)$_n$ motif is reduced, as compared with naturally occurring fibroin. It can be said that the domain sequence of the third modified fibroin has an amino acid sequence equivalent to an amino acid sequence in which at least one or a plurality of (A)$_n$ motifs are deleted, as compared with naturally occurring fibroin.

The third modified fibroin may have an amino acid sequence equivalent to an amino acid sequence in which 10% to 40% of (A)$_n$ motifs is deleted from naturally occurring fibroin.

The domain sequence of the third modified fibroin may have an amino acid sequence equivalent to an amino acid sequence obtained by deleting one of every one to three (A)$_n$ motifs at least from the N-terminal side to the C-terminal side, as compared with naturally occurring fibroin.

The domain sequence of the third modified fibroin may have an amino acid sequence equivalent to an amino acid sequence obtained by repeating deletion of at least two consecutive (A)$_n$ motifs and deletion of one (A)$_n$ motif in this order from the N-terminal side to the C-terminal side, as compared with naturally occurring fibroin.

The domain sequence of the third modified fibroin may have an amino acid sequence equivalent to an amino acid sequence obtained by deleting one of every two (A)$_n$ motifs at least from the N-terminal side to the C-terminal side.

The third modified fibroin may include a domain sequence represented by Formula 1: [(A)$_n$ motif-REP]$_m$, and have an amino acid sequence in a case where the number of amino acid residues of two [(A)$_n$ motif-REP] units adjacent to each other is sequentially compared from the N-terminal side to the C-terminal side, then the number of amino acid residues of REP having a small number of amino acid residues is set as 1, the maximum total value of the number of amino acid residues of two [(A)$_n$ motif-REP] units adjacent to each other, in which the ratio (Giza ratio) of the number of amino acid residues of the other REP is 1.8 to 11.3, is set as x, and the total number of amino acid residues in the domain sequence is set as y, x/y may be 20% or more, 30% or more, 40% or more, or 50% or more. The number of alanine residues is 83% or more with respect to the total number of amino acid residues in the (A)$_n$ motif, preferably 86% or more, more preferably 90% or more, still more preferably 95% or more, and even still more preferably 100% (which means that the (A)$_n$ motif consists of only alanine residues).

In the third modified fibroin, x/y is preferably 50% or more, more preferably 60% or more, still more preferably 65% or more, even still more preferably 70% or more, still further preferably 75% or more, and particularly preferably 80% or more. The upper limit of x/y is not particularly limited, but it may be 100% or less, for example. In a case where the Giza ratio is 1:1.9 to 11.3, x/y is preferably 89.6% or more. In a case where the Giza ratio is 1:1.8 to 3.4, x/y is more preferably 77.1% or more. In a case where the Giza ratio is 1:1.9 to 8.4, x/y is still more preferably 75.9% or more. In a case where the Giza ratio is 1:1.9 to 4.1, x/y is even still more preferably 64.2% or more.

In a case where the third modified fibroin is a modified fibroin in which at least seven of multiple (A)$_n$ motifs present in the domain sequence are composed of only alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited as long as it is 100% or less.

The third modified fibroin, for example, can be obtained by deleting one or a plurality sequences encoding (A)$_n$ motif from a cloned gene sequence of naturally occurring fibroin such that x/y is 64.2% or more. Alternatively, the third modified fibroin may also be obtained, for example, by designing an amino acid sequence equivalent to an amino acid sequence obtained by deleting one or a plurality (A)$_n$ motifs such that x/y is 64.2% or more based on the amino acid sequence of naturally occurring fibroin and chemically synthesizing a nucleic acid encoding the designed amino acid sequence. In any case, with respect to the amino acid sequence of naturally occurring fibroin, in addition to the modification equivalent to deletion of (A)$_n$ motif, further modification of amino acid sequence equivalent to substitution, deletion, insertion and/or addition of one or a plurality of amino acid residues may be carried out.

More specific examples of the third modified fibroin can include a modified fibroin including (3-i) the amino acid sequence set forth in SEQ ID NO: 41 (Met-PRT399), SEQ ID NO: 31 (Met-PRT410), SEQ ID NO: 32 (Met-PRT525), or SEQ ID NO: 33 (Met-PRT799), and (3-ii) an amino acid sequence having 90% or more sequence identity with the amino acid sequence set forth in SEQ ID NO: 41, SEQ ID NO: 31, SEQ ID NO: 32, or SEQ ID NO: 33.

The modified fibroin of (3-i) will be described. The amino acid sequence set forth in SEQ ID NO: 41 is obtained by deleting one of every two (A)$_n$ motifs from the N-terminal side to the C-terminal side in the amino acid sequence set forth in SEQ ID NO: 34 (Met-PRT313) equivalent to naturally occurring fibroin and by further inserting one [(A)$_n$ motif-REP] just before the C-terminal sequence. The amino acid sequence set forth in SEQ ID NO: 31, SEQ ID NO: 32, or SEQ ID NO: 33 is as described in the second modified fibroin.

The value of x/y with a Giza ratio of 1:1.8 to 11.3 in the amino acid sequence set forth in SEQ ID NO: 34 (equivalent to naturally occurring fibroin) is 15.0%. Both the value of x/y in the amino acid sequence set forth in SEQ ID NO: 41 and the value of x/y in the amino acid sequence set forth in SEQ ID NO: 31 are 93.4%. The value of x/y in the amino acid sequence set forth in SEQ ID NO: 32 is 92.7%. The value of x/y in the amino acid sequence set forth in SEQ ID NO: 33 is 89.8%. The values of z/w in the amino acid sequences set forth in SEQ ID NO: 34, SEQ ID NO: 41, SEQ ID NO: 31, SEQ ID NO: 32, and SEQ ID NO: 33 are respectively 46.8%, 56.2%, 70.1%, 66.1%, and 70.0%.

The modified fibroin of (3-i) may consist of the amino acid sequence set forth in SEQ ID NO: 41, SEQ ID NO: 31, SEQ ID NO: 32, or SEQ ID NO: 33.

The modified fibroin of (3-ii) includes an amino acid sequence having 90% or more sequence identity with the amino acid sequence set forth in SEQ ID NO: 41, SEQ ID NO: 31, SEQ ID NO: 32, or SEQ ID NO: 33. The modified fibroin of (340 is also a protein including a domain sequence represented by Formula 1: $[(A)_n \text{ motif-REP}]_m$. The sequence identity is preferably 95% or more.

The modified fibroin of (340 preferably has 90% or more sequence identity with the amino acid sequence set forth in SEQ ID NO: 41, SEQ ID NO: 31, SEQ ID NO: 32, or SEQ ID NO: 33, and in a case where the number of amino acid residues of two $[(A)_n \text{ motif-REP}]$ units adjacent to each other is sequentially compared from the N-terminal side to the C-terminal side, then the number of amino acid residues of one REP having a small number of amino acid residues is set as 1, the maximum total value of the number of amino acid residues of two $[(A)_n \text{ motif-REP}]$ units adjacent to each other, in which the ratio (1:1.8 to 11.3 as a Giza ratio) of the number of amino acid residues of the other REP is 1.8 to 11.3, is set as x, and the total number of amino acid residues in the domain sequence is set as y, x/y is preferably 64.2% or more.

The third modified fibroin may include a tag sequence described above at either or both of the N-terminal and C-terminal.

A more specific example of the modified fibroin including a tag sequence may be a modified fibroin including (3-iii) the amino acid sequence set forth in SEQ ID NO: 42 (PRT399), SEQ ID NO: 37 (PRT410), SEQ ID NO: 38 (PRT525), or SEQ ID NO: 39 (PRT799), or (3-iv) an amino acid sequence having 90% or more sequence identity with the amino acid sequence set forth in SEQ ID NO: 42, SEQ ID NO: 37, SEQ ID NO: 38, or SEQ ID NO: 39.

The amino acid sequences set forth in SEQ ID NO: 42, SEQ ID NO: 37, SEQ ID NO: 38, and SEQ ID NO: 39 are respectively amino acid sequences obtained by adding the amino acid sequence (including a His tag sequence and a hinge sequence) set forth in SEQ ID NO: 35 to the N-terminal of the amino acid sequences set forth in SEQ ID NO: 41, SEQ ID NO: 31, SEQ ID NO: 32, and SEQ ID NO: 33.

The modified fibroin of (3-iii) may consist of the amino acid sequence set forth in SEQ ID NO: 42, SEQ ID NO: 37, SEQ ID NO: 38, or SEQ ID NO: 39.

The modified fibroin of (3-iv) includes an amino acid sequence having 90% or more sequence identity with the amino acid sequence set forth in SEQ ID NO: 42, SEQ ID NO: 37, SEQ ID NO: 38, or SEQ ID NO: 39. The modified fibroin of (3-iv) is also a protein including a domain sequence represented by Formula 1: $[(A)_n \text{ motif-REP}]_m$. The sequence identity is preferably 95% or more.

The modified fibroin of (3-iv) preferably has 90% or more sequence identity with the amino acid sequence set forth in SEQ ID NO: 42, SEQ ID NO: 37, SEQ ID NO: 38, or SEQ ID NO: 39, and in a case where the number of amino acid residues of two $[(A)_n \text{ motif-REP}]$ units adjacent to each other is sequentially compared from the N-terminal side to the C-terminal side, then the number of amino acid residues of one REP having a small number of amino acid residues is set as 1, the maximum total value of the number of amino acid residues of two $[(A)_n \text{ motif-REP}]$ units adjacent to each other, in which the ratio of the number of amino acid residues of the other REP is 1.8 to 11.3, is set as x, and the total number of amino acid residues in the domain sequence is set as y, is preferably 64.2% or more.

The third modified fibroin may include a secretory signal for releasing the protein produced in the recombinant protein production system to the outside of a host. The sequence of the secretory signal can be appropriately set depending on the type of the host.

The domain sequence of the fourth modified fibroin has an amino acid sequence with not only a reduced content of $(A)_n$ motif but also a reduced content of glycine residue, as compared with naturally occurring fibroin. It can be said that the domain sequence of the fourth modified fibroin has an amino acid sequence equivalent to an amino acid sequence in which at least one or a plurality of $(A)_n$ motifs are deleted and at least one or a plurality of glycine residues in REP are further substituted with other amino acid residues, as compared with naturally occurring fibroin. That is, the fourth modified fibroin is a modified fibroin having the characteristics of the second modified fibroin and the third modified fibroin described above. Specific aspects and the like of the fourth modified fibroin are as described in the second modified fibroin and the third modified fibroin.

More specific examples of the fourth modified fibroin can include a modified fibroin including (4-i) the amino acid sequence set forth in SEQ ID NO: 31 (Met-PRT410), SEQ ID NO: 32 (Met-PRT525), SEQ ID NO: 33 (Met-PRT799), SEQ ID NO: 37 (PRT410), SEQ ID NO: 38 (PRT525), or SEQ ID NO: 39 (PRT799), and (4-ii) an amino acid sequence having 90% or more sequence identity with the amino acid sequence set forth in SEQ ID NO: 31, SEQ ID NO: 32, SEQ ID NO: 33, SEQ ID NO: 37, SEQ ID NO: 38, or SEQ ID NO: 39. Specific aspects of the modified fibroin including the amino acid sequence set forth SEQ ID NO: 31, SEQ ID NO: 32, SEQ ID NO: 33, SEQ ID NO: 37, SEQ ID NO: 38, or SEQ ID NO: 39 are as described above.

The domain sequence of the fifth modified fibroin may include a domain sequence having an amino acid sequence locally containing a region with a high hydropathy index equivalent to an amino acid sequence in which one or a plurality of amino acid residues in REP are substituted with amino acid residues with a high hydropathy index and/or one or a plurality of amino acid residues with a high hydropathy index are inserted into REP, as compared with naturally occurring fibroin.

It is preferable that the region locally having high hydropathy index is constituted of two to four consecutive amino acid residues.

It is more preferable that the amino acid residues with a high hydropathy index are selected from isoleucine (I), valine (V), leucine (L), phenylalanine (F), cysteine (C), methionine (M), and alanine (A).

The fifth modified fibroin may further include an amino acid sequence equivalent to an amino acid sequence in which one or a plurality of amino acid residues are substituted, deleted, inserted and/or added, as compared with naturally occurring fibroin, in addition to a modification corresponding to the modification in which one or a plurality of amino acid residues in REP are substituted with amino acid residues with a high hydropathy index and/or one or a plurality of amino acid residues with a high hydropathy index are inserted into REP, as compared with naturally occurring fibroin.

The fifth modified fibroin may be obtained by, with respect to a cloned gene sequence of naturally occurring fibroin, substituting one or a plurality of hydrophilic amino acid residues in REP (for example, amino acid residues having a negative hydropathy index) with a hydrophobic amino acid residue (for example, amino acid residues having a positive hydropathy index), and/or inserting one or a plurality of hydrophobic amino acid residues into REP. Further, for example, the fifth modified fibroin may also be obtained by designing an amino acid sequence equivalent to an amino acid sequence in which with respect to the amino acid sequence of naturally occurring fibroin, one or a plurality of hydrophilic amino acid residues in REP are substituted with hydrophobic amino acid residues and/or one or a plurality of hydrophobic amino acid residues are inserted into REP, and chemically synthesizing a nucleic acid encoding the designed amino acid sequence. In any case, with respect to the amino acid sequence naturally occurring fibroin, in addition to the modification equivalent to substitution of one or a plurality of hydrophilic amino acid residues in REP with hydrophobic amino acid residues and/or insertion of one or a plurality of hydrophobic amino acid residues into REP, further modification of amino acid sequence equivalent to substitution, deletion, insertion and/or addition of one or a plurality of amino acid residues may be carried out.

A fifth modified fibroin may include a domain sequence represented by Formula 1: $[(A)_n \text{ motif-REP}]_m$ and have an amino acid sequence in which p/q is 6.2% or more, in a case where in all REPs included in a sequence excluding a sequence from a $(A)_n$ motif located to most C-terminal side to the C-terminal of the domain sequence from the domain sequence, the total number of amino acid residues contained in a region where an average value of hydropathy indices of four consecutive amino acid residues is 2.6 or more is set as p, and the total number of amino acid residues contained in the sequence excluding the sequence from the $(A)_n$ motif located the most C-terminal side to the C-terminal of the domain sequence from the domain sequence is set as q.

Regarding the hydropathy index of amino acid residues, known indices (Hydropathy index: Kyte J, & Doolittle R (1982) from "A simple method for displaying the hydropathic character of a protein", J. Mol. Biol., 157, pp. 105-132) may be used as a reference. Specifically, the hydropathy index (hereinafter also referred to as "HI") of each amino acid is as shown in Table 1 above.

The calculation method of p/q will be described in more detail. In the calculation, the sequence (hereinafter also referred to as "sequence A") excluding the sequence from the $(A)_n$ motif located at the most C-terminal side to the C-terminal of the domain sequence from the domain sequence represented by Formula 1: $[(A)_n \text{ motif-REP}]_m$ is used. First, in all REPs included in the sequence A, average values of hydropathy indices of four consecutive amino acid residues are calculated. The average value of the hydropathy indices is obtained by dividing the total sum of HI of each of the amino acid residues contained in the four consecutive amino acid residues by 4 (the number of amino acid residues). The average value of the hydropathy indices is obtained for all of the four consecutive amino acid residues (each of the amino acid residues is used for calculating the average value 1 to 4 times). Next, a region where the average value of the hydropathy indices of the four consecutive amino acid residues is 2.6 or more is specified. Even if a plurality of a certain amino acid residue are determined to correspond to the "four consecutive amino acid residues having an average value of the hydropathy indices of 2.6 or more", the amino acid residue is counted as one amino acid residue in the region. The total number of amino acid residues included in the region is set as p. The total number of amino acid residues included in the sequence A is set as q.

For example, in a case where the feature "four consecutive amino acid residues whose average value of the hydropathy indices is 2.6 or more" is extracted from 20 places (no overlap), in the region where the average value of the hydropathy indices of four consecutive amino acid residues is 2.6 or more, the number of the four consecutive amino acid residues (no overlap) is 20, and thus p is 20×4=80. In addition, for example, when two of the "four consecutive amino acid residues having an average value of the hydropathy indices of 2.6 or more" overlap by one amino acid residue, in the region where the average value of the hydropathy indices of the four consecutive amino acid residues is 2.6 or more, the number of amino acid residues being included is 7(p=2×4-1=7. "-1" is the deduction of overlap).

In the fifth modified fibroin, p/q is preferably 6.2% or more, more preferably 7% or more, still more preferably 10% or more, even still more preferably 20% or more, and still further preferably 30% or more. The upper limit of p/q is not particularly limited, but it may be 45% or less, for example.

The fifth modified fibroin may be obtained by, for example, modifying an amino acid sequence of cloned naturally occurring fibroin into an amino acid sequence containing a region locally having a high hydropathy index by substituting one or a plurality of hydrophilic amino acid residues in REP (for example, amino acid residues having a negative hydropathy index) with hydrophobic amino acid residues (for example, amino acid residues having a positive hydropathy index), and/or inserting one or a plurality of hydrophobic amino acid residues into REP, such that the p/q condition is satisfied. Alternatively, the fifth modified fibroin may also be obtained, for example, by designing an amino acid sequence satisfying the p/q condition based on the amino acid sequence of naturally occurring fibroin and chemically synthesizing a nucleic acid encoding the designed amino acid sequence. In any case, in addition to the modification equivalent to substitution of one or a plurality of amino acid residues in REP with amino acid residues with a high hydropathy index and/or insertion of one or a plurality of amino acid residues with a high hydropathy index into REP, as compared with the naturally occurring fibroin, further modification equivalent to substitution, deletion, insertion, and/or addition of one or a plurality of amino acid residues may be carried out.

The amino acid residues with a high hydropathy index is preferably isoleucine (I), valine (V), leucine (L), phenylalanine (F), cysteine (C), methionine (M), and alanine (A), and more preferably valine (V), leucine (L), and isoleucine (I), but not particularly thereto.

More specific examples of the fifth modified fibroin can include a modified fibroin including (5-i) the amino acid sequence set forth in SEQ ID NO: 43 (Met-PRT720), SEQ ID NO: 44 (Met-PRT665), or SEQ ID NO: 45 (Met-PRT666), and (5-ii) an amino acid sequence having 90% or more sequence identity with the amino acid sequence set forth in SEQ ID NO: 43, SEQ ID NO: 44, or SEQ ID NO: 45.

The modified fibroin of (5-i) will be described. The amino acid sequence set forth in SEQ ID NO: 43 is obtained by inserting an amino acid sequence consisting of three amino acid residues (VLI) at two sites for each REP with respect to the amino acid sequence set forth in SEQ ID NO: 31 (Met-PRT410), except for the domain sequence at the end on the C-terminal side, and further substituting a part of glutamine (Q) residues with serine (S) residues and deleting a part of amino acids on the C-terminal side. The amino acid sequence set forth in SEQ ID NO: 44 is obtained by inserting an amino acid sequence consisting of three amino acid residues (VLI) at one site for each REP with respect to the amino acid sequence set forth in SEQ ID NO: 42 (Met- PRT525). The amino acid sequence set forth in SEQ ID NO: 45 is obtained by inserting an amino acid sequence consisting of three amino acid residues (VLI) at two sites for each REP with respect to the amino acid sequence set forth in SEQ ID NO: 32.

The modified fibroin of (5-i) may consist of the amino acid sequence set forth in SEQ ID NO: 43, SEQ ID NO: 44, or SEQ ID NO: 45.

The modified fibroin of (5-ii) includes an amino acid sequence having 90% or more sequence identity with the amino acid sequence set forth in SEQ ID NO:43, SEQ ID NO: 44, or SEQ ID NO: 45. The modified fibroin of (5-ii) is also a protein including a domain sequence represented by Formula 1: $[(A)_n \text{ motif-REP}]_m$. The sequence identity is preferably 95% or more.

The modified fibroin of (5-ii) preferably has 90% or more sequence identity with the amino acid sequence set forth in SEQ ID NO: 43, SEQ ID NO: 44, or SEQ ID NO: 45, and preferably has an amino acid sequence in which p/q is 6.2% or more, in a case where in all REPs included in a sequence excluding a sequence from a $(A)_n$ motif located the most C-terminal side to the C-terminal of the domain sequence from the domain sequence, the total number of amino acid residues contained in a region where an average value of hydropathy indices of four consecutive amino acid residues is 2.6 or more is set as p, and the total number of amino acid residues contained in the sequence excluding the sequence from the $(A)_n$ motif located the most C-terminal side to the C-terminal of the domain sequence from the domain sequence is set as q.

The fifth modified fibroin may include a tag sequence at either or both of the N-terminal and C-terminal.

A more specific example of the modified fibroin including a tag sequence may be a modified fibroin including (5-iii) the amino acid sequence set forth in SEQ ID NO: 46 (PRT720), SEQ ID NO: 47 (PRT665), or SEQ ID NO: 48 (PRT666), or (5-iv) an amino acid sequence having 90% or more sequence identity with the amino acid sequence set forth in SEQ ID NO: 46, SEQ ID NO: 47, or SEQ ID NO: 48.

The amino acid sequences set forth in SEQ ID NO: 46, SEQ ID NO: 47, and SEQ ID NO: 48 are respectively amino acid sequences obtained by adding the amino acid sequence (including a His tag and a hinge sequence) set forth in SEQ ID NO: 35 to the N-terminal of the amino acid sequences set forth in SEQ ID NO: 43, SEQ ID NO: 44, and SEQ ID NO: 45.

The modified fibroin of (5-iii) may consist of the amino acid sequence set forth in SEQ ID NO: 46, SEQ ID NO: 47, or SEQ ID NO: 48.

The modified fibroin of (5-iv) includes an amino acid sequence having 90% or more sequence identity with the amino acid sequence set forth in SEQ ID NO: 46, SEQ ID NO: 47, or SEQ ID NO: 48. The modified fibroin of (5-iv) is also a protein including a domain sequence represented by Formula 1: $[(A)_n \text{ motif-REP}]_m$. The sequence identity is preferably 95% or more.

The modified fibroin of (5-iv) preferably has 90% or more sequence identity with the amino acid sequence set forth in SEQ ID NO: 46, SEQ ID NO: 47, or SEQ ID NO: 48, and preferably has an amino acid sequence in which p/q is 6.2% or more, in a case where in all REPs included in a sequence excluding a sequence from a $(A)_1$ motif located the most C-terminal side to the C-terminal of the domain sequence from the domain sequence, the total number of amino acid residues contained in a region where an average value of hydropathy indices of four consecutive amino acid residues is 2.6 or more is set as p, and the total number of amino acid residues contained in the sequence excluding the sequence from the $(A)_n$ motif located the most C-terminal side to the C-terminal of the domain sequence from the domain sequence is set as q.

The fifth modified fibroin may include a secretory signal for releasing the protein produced in the recombinant protein production system to the outside of a host. The sequence of the secretory signal can be appropriately set depending on the type of the host.

The sixth modified fibroin has an amino acid sequence with a reduced content of glutamine residue, as compared with naturally occurring fibroin. Preferred aspects and the like of the sixth modified fibroin are as described above.

As the modified fibroin in the artificially modified fibroin fiber according to the present embodiment, the sixth modified fibroin is preferable due to the fact that, when the dimension changes (elongation and shrinkage) due to contact with water and subsequent drying, the degree of elongation is approximately the same as the degree of shrinkage (restoration rate is close to 100%) and the sixth modified fibroin has the characteristic of being able to restore the original length thereof, and the dimensional change of the sixth modified fibroin due to contact with water and subsequent drying is reduced.

The artificially modified fibroin fiber according to the present embodiment can be obtained by a production method including a shrinking step of shrinking a raw fiber obtained by spinning the modified fibroin with water. The shrinking step may include, for example, a step (contact step) of irreversibly shrinking the raw fiber (raw fiber before contact with water after spinning) by bring the raw fiber into contact with water. The shrinking step may include a step (drying step) of drying and further shrinking the fiber after the contact step.

The raw fiber can be produced using a known spinning method. Specifically, for example, the raw fiber can be produced according to the fibroin fiber spinning method described above.

Figure 3:
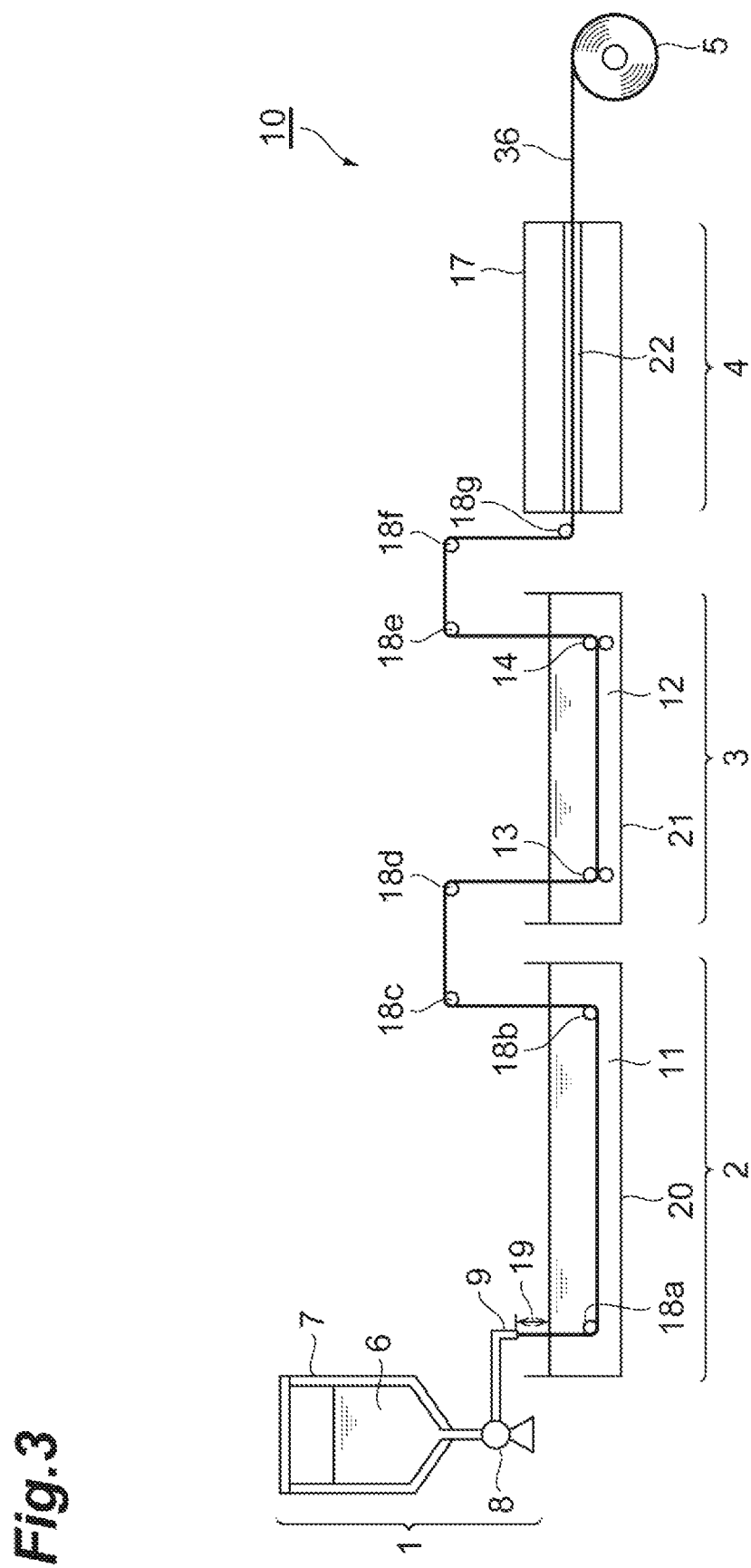
FIG. 3 is an illustrative view schematically showing an example of a spinning device for producing raw fiber.

FIG. 3 is an illustrative view schematically showing an example of a spinning device for producing raw fiber. A spinning device 10 shown in FIG. 3 is an example of a spinning device for dry-wet-type spinning, and includes an extrusion device 1, an undrawn yarn production device 2, a wet heat drawing device 3, and a drying device 4.

A spinning method using the spinning device 10 will be described. First, a doping liquid 6 stored in a storage tank 7 is pushed out from a spinneret 9 by a gear pump 8. In the laboratory scale, the doping liquid may be filled in a cylinder and extruded from a nozzle using a syringe pump. Next, the extruded doping liquid 6 is supplied into a coagulation liquid 11 in a coagulation liquid bath 20 via an air gap 19, solvent is removed, the modified fibroin is coagulated, and a fibrous coagulate is formed. Then, the fibrous coagulate is supplied into a hot water 12 in a drawing bath 21 and is drawn. A drawing ratio is determined according to a speed ratio between a supply nip roller 13 and an withdrawing nip roller 14. Thereafter, the drawn fibrous coagulate is supplied to a drying device 4 and dried in a yarn path 22, and the raw fiber is obtained as a wound yarn body 5. Reference signs 18a to 18g indicate yarn guides.

The coagulation liquid 11 may be any solvent that can be desolvated, and examples thereof include lower alcohols having 1 to 5 carbon atoms such as methanol, ethanol, and 2-propanol, and acetone. The coagulation liquid 11 may appropriately contain water. The temperature of the coagulation liquid 11 is preferably 0° C. to 30° C. In a case where a syringe pump having a nozzle with a diameter of 0.1 to 0.6 mm is used as the spinneret 9, the extrusion speed is preferably 0.2 to 6.0 ml/hour per hole and more preferably 1.4 to 4.0 ml/hour. The distance that the coagulated protein passes through the coagulation liquid 11 (substantially, the distance from the yarn guide 18*a* to the yarn guide 18*b*) may be a length that allows efficient desolvation, for example, 200 to 500 mm. The withdrawing speed of the undrawn yarn may be, for example, 1 to 20 m/min and preferably 1 to 3 m/min. The residence time in the coagulation liquid 11 may be, for example, 0.01 to 3 minutes and preferably 0.05 to 0.15 minutes. In addition, drawing (pre-drawing) may be performed in the coagulation liquid 11. The coagulation liquid bath 20 may be provided in multiple stages, and the drawing may be performed in each stage or in a specific stage as necessary.

As the drawing performed when obtaining the raw fiber, for example, a pre-drawing performed in the coagulation liquid bath 20 and a wet heat drawing performed in the drawing bath 21 are employed, and a dry heat drawing is also employed.

The wet heat drawing can be performed in warm water, in a solution obtained by adding an organic solvent or the like to warm water, or in heated steam. The temperature may be, for example, 50° C. to 90° C. and preferably 75° C. to 85° C. In the wet heat drawing, the undrawn yarn (or pre-drawn yarn) can be drawn, for example, by 1 to 10 times and preferably by 2 to 8 times.

The dry heat drawing can be performed using an electric tubular furnace, a dry heat plate, or the like. The temperature may be, for example, 140° C. to 270° C. and preferably 160° C. to 230° C. In the dry heat drawing, the undrawn yarn (or pre-drawn yarn) can be drawn, for example, by 0.5 to 8 times and preferably by 1 to 4 times.

The wet heat drawing and the dry heat drawing may be performed independently or in combination, or may be performed in multiple stages. That is, the wet heat drawing and the dry heat drawing can be performed in suitable combination, for example, in a manner in which a first stage drawing is performed by wet heat drawing and a second stage drawing is performed by dry heat drawing or in a manner in which the first stage drawing is performed by wet heat drawing, the second stage drawing is performed by wet heat drawing, and a third stage drawing is performed by dry heat drawing.

The lower limit value of the final drawing ratio with respect to the undrawn yarn (or pre-drawn yarn) is preferably any of more than 1 time, 2 times or more, 3 times or more, 4 times or more, 5 times or more, 6 times or more, 7 times or more, 8 times or more, or 9 times or more, and the upper limit value is preferably 40 times or less, 30 times or less, 20 times or less, 15 times or less, 14 times or less, 13 times or less 12 times or less, 11 times or less, or 10 times or less. In a case where the raw fiber is a fiber spun at a drawing ratio of 2 times or more, the shrinkage rate when the raw fiber is wetted by being brought into contact with water becomes higher.

As shown in FIG. 2, the raw fiber (fiber containing the modified fibroin) has a characteristic of shrinkage (change in length indicated by "first shrinkage" in FIG. 2) by contacting (wetting) with water. After first shrinkage, the raw fiber further shrinks when dried (change in length indicated by "second shrinkage" in FIG. 2). After second shrinkage, the fibroin fiber elongates again to the same or similar length before second shrinkage by contact with water, and then repeats shrinkage and elongation in a length range (indicated by "stretch rate" in FIG. 2) similar to the length range in second shrinkage in a case of subsequently repeating drying and wetting. Accordingly, the artificially modified fibroin fiber according to the present embodiment can be obtained by a production method including a shrinking step including at least the contact step.

The irreversible shrinkage ("first shrinkage" in FIG. 2) of the raw fiber (fiber containing the modified fibroin) in the contact step is considered to occur, for example, due to the following reason. That is, one reason is considered to be due to the secondary structure and tertiary structure of the raw fiber (fiber containing modified fibroin). Another reason is considered to be that, for example, in the raw fiber (fiber containing modified fibroin) having a residual stress due to drawing or the like in the production process, the residual stress is relieved by water entering between fibers or into the fiber. Accordingly, it is thought that it is possible to freely control the shrinkage rate of the raw fiber (fiber containing modified fibroin) in the shrinking step, for example, according to the size of the drawing ratio in the manufacturing process of the raw fiber (fiber containing modified fibroin) described above.

In the contact step, the raw fiber before contact with water and after spinning is brought into contact with water to make the raw fiber wetted. The wetted state means a state in which at least a part of the raw fiber is wetted with water. As a result, the raw fiber can be shrunk without external force. This shrinkage is irreversible (corresponds to "first shrinkage" in FIG. 2).

The temperature of the water contacted with the raw fiber in the contact step may be lower than the boiling point. As a result, the handleability and the workability in the shrinkage step are improved. In addition, from the viewpoint of sufficiently shortening the shrinkage time, the lower limit value of the water temperature is preferably 10° C. or higher, more preferably 40° C. or higher, and still more preferably 70° C. or higher. The upper limit value of the water temperature is preferably 90° C. or lower.

In the contact step, the method of bringing water into contact with the raw fiber is not particularly limited. Examples of the method thereof include a method of immersing the raw fiber in water, a method of spraying water on the raw fiber at room temperature, in heated steam, or the like, and a method of exposing the raw fiber to a high humid environment in which water vapor is filled. Among these methods, the method of immersing the raw fiber in water is preferable in the contact step, since the shrinkage time can be effectively shortened and the processing equipment can be simplified.

In a case where the raw fiber is brought into contact with water in a relaxed state in the contact step, the raw fiber may not only shrink but also be curled to be wavy. In order to prevent the occurrence of curling, for example, the contact step may be performed in a state where the raw fiber is not relaxed, for example in a state where the raw fiber is brought into contact with water while being tensioned (pulled) in a fiber axis direction.

The method for producing the artificially modified fibroin fiber according to the present embodiment may further include the drying step. The drying step is a step of drying and further shrinking the raw fiber (or artificially modified fibroin fiber obtained through the contact step) that has passed the contact step (corresponds to "second shrinkage" in FIG. 2). Drying may be, for example, a natural drying or a forced drying using a drying equipment. As the drying equipment, any known drying equipment of contact type or non-contact type can be used. In addition, the drying temperature is not limited as long as it is lower than the temperature at which the protein contained in the raw fiber is degraded or the raw fiber is thermally damaged. Generally, the temperature is in the range of 20° C. to 150° C., and the temperature is preferably in the range of 50° C. to 100° C. With the temperature in this range, the fiber is dried more quickly and efficiently without thermal damage to the fiber or degradation of the protein contained in the fiber. The drying time is appropriately set according to the drying temperature or the like, and for example, a time during which the influence on the quality and physical properties of the artificially modified fibroin fiber due to overdrying can be eliminated as much as possible is employed.

The artificially modified fibroin fiber according to the present embodiment is obtained, for example, by the above-described production method, and therefore substantially contain no residual stress generated by drawing in the spinning process.

The artificially modified fibroin fiber according to the present embodiment may have a restoration rate defined by Expression (1) of 95% or more.

restoration rate=(length of artificially modified fibroin fiber when dried from wetted state/ length of artificially modified fibroin fiber before being wetted)×100(%)  Expression (1):

It can be said that the higher the restoration rate defined by Expression (1), the more the artificially modified fibroin fiber can restore the original length when wetted/dried. In the artificially modified fibroin fiber according to the present embodiment, the restoration rate defined by Expression (1) is preferably 96% or more, more preferably 97% or more, still more preferably 98% or more, and even still more preferably 99% or more.

The artificially modified fibroin fiber according to the present embodiment may have an elongation rate defined by Expression (4) of 17% or less. The elongation rate defined by Expression (4) is an index of elongatability when the artificially modified fibroin fiber is in a wetted state.

elongation rate={(length of artificially modified fibroin fiber when wetted/length of artificially modified fibroin fiber before being wetted)−1}× 100(%)  Expression (4):

The upper limit of the elongation rate defined by Expression (4) is, for example, 15% or less, 13% or less, 10% or less, or 5% or less, and the lower limit is, for example, more than 0%, 1% or more, 2% or more, 5% or more, 10% or more, or 13% or more. The elongation rate defined by Expression (4) may be, for example, more than 0% and 17% or less, more than 0% and 15% or less, 2% or more and 15% or less, 5% or more and 15% or less, 5% or more and 13% or less, 5% or more and 10% or less, more than 0% and 10% or less, or more than 0% and 5% or less.

The artificially modified fibroin fiber according to the present embodiment may have a shrinkage rate C defined by Expression (5) of 17% or less. The shrinkage rate C defined by Expression (5) is an index of shrinkability when the artificially modified fibroin fiber is dried from a wetted state.

shrinkage rate C={1−(length of artificially modified fibroin fiber when dried from wetted state/ length of artificially modified fibroin fiber when wetted)}×100(%)  Expression (5):

The upper limit of the shrinkage rate C defined by Expression (5) is, for example, 15% or less, 13% or less, 10% or less, or 5% or less, and the lower limit is, for example, more than 0%, 1% or more, 2% or more, 5% or more, 10% or more, or 13% or more. The shrinkage rate C defined by Expression (5) may be, for example, more than 0% and 17% or less, more than 0% and 15% or less, 2% or more and 15% or less, 5% or more and 15% or less, 5% or more and 13% or less, 5% or more and 10% or less, more than 0% and 10% or less, or more than 0% and 5% or less.

The artificially modified fibroin fiber according to the present embodiment is preferably a fiber having a shrinkage history of irreversibly being shrunk by contact with water after spinning and a shrinkage rate A defined by Expression (2) of 2% or more. The shrinkage rate A defined by Expression (2) is an index indicating characteristics relating to the first shrinkage of the raw fiber (see FIG. 2). In a case where the shrinkage rate A defined by Expression (2) is 2% or more, the restoration rate defined by Expression (1) becomes higher.

shrinkage rate A={1−(length of fiber irreversibly shrunk by contact with water after spinning/ length of fiber before contact with water and after spinning)}×100(%)  Expression (2):

The shrinkage rate A defined by Expression (2) may be 2.5% or more, 3% or more, 3.5% or more, 4% or more, 4.5% or more, 5% or more, 5.5% or more, 6% more, 10% or more, 15% or more, 20% or more, or 25% or more. The upper limit of the shrinkage rate A defined by Expression (2) is not particularly limited, but is 80% or less, 60% or less, 40% or less, 20% or less, 10% or less, 7% or less, 6% or less, 5% or less, 4% or less, or 3% or less.

The artificially modified fibroin fiber according to the present embodiment is preferably a fiber having a shrinkage history of irreversibly being shrunk by contact with water after spinning and then further being shrunk by drying and a shrinkage rate B defined by Expression (3) of 7% or more. The shrinkage rate B defined by Expression (3) is an index indicating characteristics relating to the first shrinkage and the second shrinkage of the raw fiber (see FIG. 2). In a case where the shrinkage rate B defined by Expression (3) is more than 7%, the restoration rate defined by Expression (1) becomes higher.

shrinkage rate B={1−(length of fiber irreversibly shrunk by contact with water after spinning and then further shrunk by drying/length of fiber before contact with water and after spinning)}× 100(%)  Expression (3):

The shrinkage rate B defined by Expression (3) may be 10% or more, 15% or more, more than 25%, 32% or more, 40% or more, 48% or more, 56% or more, 64% or more, or 72% or more. The upper limit of the shrinkage rate B defined by Formula (3) is not particularly limited, but is usually 80% or less.

EXAMPLES

Hereinafter, the present invention will be described more specifically based on Examples. However, the present invention is not limited to following Examples.

Test Example 1

[(1) Synthesis of Nucleic Acid Encoding Modified Fibroin and Construction of Expression Vector]

Based on the base sequence and amino acid sequence of *Nephila clavipes* (GenBank Accession Number: P46804.1, GI: 1174415) which is naturally occurring fibroin, fibroins and modified fibroins having amino acid sequences set forth in SEQ ID NOs: 8 to 14 and 18 to 20 were designed.

The amino acid sequence set forth in SEQ ID NO: 8 (PRT410: Test Example 1-1) is obtained by adding the amino acid sequence set forth in SEQ ID NO: 7 (tag sequence and hinge sequence) to the N-terminal of the amino acid sequence set forth in SEQ ID NO: 1 (M_PRT410). M_PRT410 (SEQ ID NO: 1) is a modified amino acid sequence obtained by changing the number of consecutive alanine residues in (A)$_n$ motif to five, or the like, so as to improve productivity, based on the base sequence and amino acid sequence of *Nephila clavipes* (GenBank Accession Number: P46804.1, GI: 1174415) which is naturally occurring fibroin. However, since M_PRT410 (SEQ ID NO: 1) has no modification of glutamine residue (Q), the glutamine residue content rate thereof is the same as the glutamine residue content of naturally occurring fibroin.

The amino acid sequence set forth in SEQ ID NO: 9 (PRT888: Test Example 1-2) is obtained by adding the amino acid sequence set forth in SEQ ID NO: 7 (tag sequence and hinge sequence) to the N-terminal of the amino acid sequence set forth in SEQ ID NO: 2 (M_PRT888). M_PRT888 (SEQ ID NO: 2) is obtained by substituting all QQs in M_PRT410 (SEQ ID NO: 1) with VL.

The amino acid sequence set forth in SEQ ID NO: 10 (PRT965: Test Example 1-3) is obtained by adding the amino acid sequence set forth in SEQ ID NO: 7 (tag sequence and hinge sequence) to the N-terminal of the amino acid sequence set forth in SEQ ID NO: 3 (M_PRT965). M_PRT965 (SEQ ID NO: 3) is obtained by substituting all QQs in M_PRT410 (SEQ ID NO: 1) with TS and substituting the remaining Q with A.

The amino acid sequence set forth in SEQ ID NO: 11 (PRT889: Test Example 1-4) is obtained by adding the amino acid sequence set forth in SEQ ID NO: 7 (tag sequence and hinge sequence) to the N-terminal of the amino acid sequence set forth in SEQ ID NO: 4 (M_PRT889). M_PRT889 (SEQ ID NO: 4) is obtained by substituting all QQs in M_PRT410 (SEQ ID NO: 1) with VL and substituting the remaining Q with I.

The amino acid sequence set forth in SEQ ID NO: 12 (PRT916: Test Example 1-5) is obtained by adding the amino acid sequence set forth in SEQ ID NO: 7 (tag sequence and hinge sequence) to the N-terminal of the amino acid sequence set forth in SEQ ID NO: 5 (M_PRT916). M_PRT916 (SEQ ID NO: 5) is obtained by substituting all QQs in M_PRT410 (SEQ ID NO: 1) with VI and substituting the remaining Q with L.

The amino acid sequence set forth in SEQ ID NO: 13 (PRT918: Test Example 1-6) is obtained by adding the amino acid sequence set forth in SEQ ID NO: 7 (tag sequence and hinge sequence) to the N-terminal of the amino acid sequence set forth in SEQ ID NO: 6 (M_PRT918). M_PRT918 (SEQ ID NO: 6) is obtained by substituting all QQs in M_PRT410 (SEQ ID NO: 1) with VF and substituting the remaining Q with I.

The amino acid sequence set forth in SEQ ID NO: 14 (PRT720: Test Example 1-7) is obtained by inserting an amino acid sequence consisting of three amino acid residues (VLI) at two sites for each REP with respect PRT410 (SEQ ID NO: 8), and deleting a part of the amino acids on the N-terminal side therefrom such that the molecular weight thereof is set to be approximately the same as that of PRT410 (SEQ ID NO: 8).

The amino acid sequence set forth in SEQ ID NO: 18 (PRT525: Test Example 1-8) is obtained by adding the amino acid sequence set forth in SEQ ID NO: 0.7 (tag sequence and hinge sequence) to the N-terminal of the amino acid sequence set forth in SEQ ID NO: 15 (M_PRT525). M_PRT525 (SEQ ID NO: 15) is obtained by, with respect to M_PRT410 (SEQ ID NO: 1), inserting two alanine residues in a region (A$_5$) in which alanine residues are consecutive, and by deleting two domain sequences at the C-terminal side and substituting 13 glutamine (Q) residues with serine (S) residue or proline (P) residue such that the molecular weight thereof becomes approximately the same as that of M_PRT410.

The amino acid sequence set forth in SEQ ID NO: 19 (PRT699: Test Example 1-9) is obtained by adding the amino acid sequence set forth in SEQ ID NO: 7 (tag sequence and hinge sequence) to the N-terminal of the amino acid sequence set forth in SEQ ID NO: 16 (M_PRT699). M_PRT699 (SEQ ID NO: 16) is obtained by substituting all QQs in M_PRT525 (SEQ ID NO: 15) with VL.

The amino acid sequence set forth in SEQ ID NO: 20 (PRT698: Test Example 1-10) is obtained by adding the amino acid sequence set forth in SEQ ID NO: 7 (tag sequence and hinge sequence) to the N-terminal of the amino acid sequence set forth in SEQ ID NO: 17 (M_PRT698). M_PRT698 (SEQ ID NO: 17) is obtained by substituting all QQs in M_PRT525 (SEQ ID NO: 15) with VL and substituting the remaining Q with I.

Each of nucleic acids designed to encode proteins having amino acid sequences set forth in SEQ ID NOs: 8 to 14 and SEQ ID NOs: 18 to 20 was synthesized. In the nucleic acid, an NdeI site was added to the 5' end and an EcoRI site was added downstream of the stop codon. These five kinds of nucleic acids were cloned into a cloning vector (pUC118). Thereafter, the nucleic acid was enzymatically cleaved by treatment with NdeI and EcoRI, and then recombinated into a protein expression vector pET-22b(+) to obtain an expression vector.

[(2) Expression of Protein]

*Escherichia coli* BLR (DE3) was transformed with a pET22b(+) expression vector including each of nucleic acids encoding proteins having the amino acid sequences set forth in SEQ ID NOs: 8 to 14 and SEQ ID NOs: 18 to 20. The transformed *Escherichia coli* was cultured in 2 mL of an LB medium containing ampicillin for 15 hours. The culture solution was added to 100 mL of a seed culture medium (Table 5) containing ampicillin so that the OD$_{600}$ was 0.005. While maintaining the temperature of the culture solution at 30° C., flask culture was carried out (for about 15 hours) until the OD$_{600}$ reached 5, thereby obtaining a seed culture solution.

TABLE 5

| Seed culture medium (per 1 L at the time of culture start) | |
|---|---|
| Glucose | 5 g |
| KH$_2$PO$_4$ | 4 g |
| K$_2$HPO$_4$ | 10 g |
| Yeast Extract | 6 g |

The seed culture solution was added to a jar fermenter containing 500 mL of a production medium (Table 6) so that the transformed *Escherichia coli* was inoculated at the OD$_{600}$ of 0.05. The culture was carried out while keeping the culture solution temperature at 37° C. and controlling the pH constant at 6.9. Further, the dissolved oxygen concentration in the culture solution was maintained at 20% of the dissolved oxygen saturation concentration.

TABLE 6

| Production medium (per 1 L at the time of culture start) | |
|---|---|
| Glucose | 12 g |
| KH$_2$PO$_4$ | 9 g |
| MgSO$_4$•7H$_2$O | 2.4 g |
| Yeast Extract | 15 g |
| FeSO$_4$•7H$_2$O | 40 mg |
| MnSO$_4$•5H$_2$O | 40 mg |
| CaCl$_2$•2H$_2$O | 40 mg |
| GD-113 (anti-foaming agent) | 0.1 mL |

Immediately after glucose in the production medium was completely consumed, a feed solution (455 g/1 L of glucose and 120 g/1 L of Yeast Extract) was added at a rate of 1 mL/min. The culture was carried out while keeping the culture solution temperature at 37° C. and controlling the pH constant at 6.9. Further, the dissolved oxygen concentration in the culture solution was maintained at 20% of the dissolved oxygen saturation concentration, and the culture was carried out for. 20 hours. Thereafter, 1 M isopropyl-β-thiogalactopyranoside (IPTG) was added to the culture solution to a final concentration of 1 mM to induce the expression of the target protein. 20 hours after addition of IPTG, the culture solution was centrifuged to recover the bacterial cell pellet. SDS-PAGE was carried out using bacterial cell pellets prepared from the culture solution before the addition of IPTG and after the addition of IPTG, and the expression of the target protein was checked by the IPTG addition-dependent appearance of a band equivalent to a target protein size.

[(3) Purification of Protein]

The bacterial cell pellet recovered 2 hours after the addition of IPTG were washed with 20 mM Tris-HCl buffer solution (pH 7.4). The bacterial cell pellet after washing were suspended in 20 mM Tris-HCl buffer solution (pH 7.4) containing about 1 mM PMSF, and the cell suspension was disrupted with a high-pressure homogenizer (available from GEA Niro Soavi SpA). The disrupted cells were centrifuged to obtain a precipitate. The obtained precipitate was washed with 20 mM Tris-HCl buffer solution (pH 7.4) until the obtained precipitate became highly pure. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so that the concentration of the suspension was 100 mg/mL, and dissolved by stirring with a stirrer at 60° C. for 30 minutes. After dissolution, dialysis was carried out in water using a dialysis tube (cellulose tube 36/32 manufactured by Sanko Junyaku Co., Ltd.). The white protein aggregate obtained after dialysis was recovered by centrifugation, the water content was removed with a lyophilizer, and lyophilized powder was recovered.

[(4) Preparation of Spinning Liquid (Doping Liquid)]

Using DMSO in which lithium chloride was dissolved to be 4 mass % as a solvent, lyophilized protein powder of PRT410 (SEQ ID NO: 8: Test Example 1-1), PRT888 (SEQ ID NO: 9: Test Example 1-2), PRT965 (SEQ ID NO: 10: Test Example 1-3), PRT889 (SEQ ID NO: 11: Test Example 1-4), PRT916 (SEQ ID NO: 12: Test Example 1-5), PRT918 (SEQ ID NO: 13: Test Example 1-6), or PRT720 (SEQ ID NO: 14: Test Example 1-7) was added to the solvent so that the concentration thereof was 24 mass %. After dissolving with an aluminum block heater at 90° C. for 1 hour, insoluble matters and bubbles were removed to obtain a spinning liquid (doping liquid).

[(5) Spinning]

The spinning liquid was filled into a reserve tank and discharged from a monohole nozzle having a diameter of 0.1 or 0.2 mm into a coagulation bath containing 100 mass % methanol using a gear pump. The discharge rate was adjusted to 0.01 to 0.08 mL/min. After coagulation, washing and drawing were performed in the coagulation bath containing 100 mass % methanol. After washing and drawing, the obtained raw yarn (fibroin fiber) was dried using a dry heat plate and wound up.

[(6) Evaluation of Shrinkability of Fibroin Fiber]

The obtained raw yarn was arranged to have a length of about 30 cm and bundled to form a fibroin fiber bundle having a fineness of 150 denier. With 0.8 g of lead weight being attached to each fibroin fiber bundle, the fiber bundle was immersed in water at 40° C. for 10 minutes to cause first shrinkage, and the length of the fibroin fiber bundle was measured in water. The fibroin fiber bundle shrunk by first shrinkage was taken out of water and dried at room temperature for 2 hours with 0.8 g of lead weight being attached. After drying, the length of each fibroin fiber bundle was measured. This operation of wetting and drying was repeated three times, and then the average length when wetted (Lwet: cm unit) and the average length when dried (Ldry: cm unit) were determined to calculate the second shrinkage rate according to the following expression. The results are shown in Table. 7.

Second shrinkage rate (%)={1−(Ldry/Lwet)}*100

TABLE 7

| | Protein | Glutamine residue content rate | Hydrophobicity of REP | Second shrinkage rate (%) |
|---|---|---|---|---|
| Test Example 1-1 | PRT410 (SEQ ID NO: 8) | 17.7% | −1.52 | 12.0 |
| Test Example 1-2 | PRT888 (SEQ ID NO: 9) | 6.3% | −0.07 | 8.0 |
| Test Example 1-3 | PRT965 (SEQ ID NO: 10) | 0.0% | −0.65 | 8.2 |
| Test Example 1-4 | PRT889 (SEQ ID NO: 11) | 0.0% | 0.45 | 5.6 |
| Test Example 1-5 | PRT916 (SEQ ID NO: 12) | 0.0% | 0.47 | 4.2 |
| Test Example 1-6 | PRT918 (SEQ ID NO: 13) | 0.0% | 0.35 | 4.6 |
| Test Example 1-7 | PRT720 (SEQ ID NO: 14) | 15.0% | −0.10 | 12.0 |

PRT720 (Test Example 1-7) has the amino acid sequence obtained by inserting hydrophobic amino acid residues in PRT410 (Test Example 1-1). Due to the insertion of hydrophobic amino acid residues, the glutamine residue content of PRT720 (Test Example 1-7) is slightly low and the hydrophobicity of REP is remarkably increased in comparison with PRT410 (Test Example 1-1). However, there was no difference in second shrinkage rate between the fiber spun from PRT720 (Test Example 1-7) protein and the fiber spun from PRT410 (Test Example 1-1) protein (Test Example 1-1 and Test Example 1-7 in Table 7). From this result, it has been found that second shrinkage rate cannot be expected to be reduced in a case where only the hydrophobicity is increased.

On the other hand, in PRT888 (SEQ ID NO: 9) in which REP was designed to have approximately the same hydrophobicity as REP in PRT720 (Test Example 1-7) by substituting glutamine residue (Q) in the domain with other amino acid residue so that the glutamine residue content was reduced (6.3%), a remarkable effect of reducing the second shrinkage rate was observed (Test Example 1-2 in Table 7). This effect of reducing the second shrinkage rate was observed even in a case where the hydrophobicity of REP was not increased as in the case of PRT888, by further reducing (0%) the glutamine residue content (Test Example 1-3 in Table 7). In addition, the effect of reducing the second shrinkage rate was more remarkable in case of further reducing the glutamine residue content (0%) and substituting glutamine residue with an amino acid residue having higher hydrophobicity (Test Example 1-4 to Test Example 1-6 in Table 7).

[(7) Preparation of Doping Liquid for Film Production]

The lyophilized protein powder of PRT410 (SEQ ID NO: 8: Test Example 1-1), PRT525 (SEQ ID NO: 18: Test Example 1-8), PRT699 (SEQ ID NO: 19: Test Example 1-9), or PRT698 (SEQ ID NO: 20: Test Example 1-10) was added to 99% hexafluoro-2-propanol (HFIP) to a concentration of 10 mass %, shaken at 400 rpm and at 55° C. for 20 minutes, and dissolved to obtain a doping liquid.

[(8) Cast-Molding of Film]

A release film (manufactured by Mitsui Chemicals, Inc., product number "SP-PET-01-75-BU") having a silicone compound immobilized on the surface of a polyethylene terephthalate (PET) film having a thickness of 75 μm was used as a substrate. Using a batch type coating machine (manufactured by Imoto Seisakusho), the doping liquid prepared above was cast-molded on the surface of the substrate under the conditions of a feed speed of 20 mm/second and a slit width of 0.18 mm to prepare a wet film.

[(9) Drying and Desolvation]

The molded wet film was allowed to be left for 12 hours in a thermostatic chamber (manufactured by ESPEC CORP.) at 55° C. and dried. Thereafter, the dried film was peeled off from the substrate and immersed in methanol for 12 hours. The molded wet film was again allowed to be left for 12 hours in a thermostatic chamber (manufactured by ESPEC CORP.) at 60° C. and dried. The obtained film was cut to 30 mm square and subjected to the following waterproofness evaluation.

[(10) Evaluation of Waterproofness of Film]

The film cut to 30 mm square was placed in a Falcon tube containing a saturated aqueous solution of potassium sulfate ($K_2SO_4 \cdot H_2O$) so as not to be immersed in the aqueous solution, and was allowed to be left at 98% high humidity for 48 hours. Then, the moisture content of the film was determined as a moisture content rate (%) by measuring the degree of moisture absorption with a Karl Fischer (manufactured by Kyoto Electronics Industry Co., Ltd.). The results are shown in Table. 8.

TABLE 8

| | Protein | Glutamine residue content rate | Hydrophobicity of REP | Moisture content rate |
|---|---|---|---|---|
| Test Example 1-1 | PRT410 (SEQ ID NO: 8) | 17.7% | −1.52 | 23.31% |
| Test Example 1-8 | PRT525 (SEQ ID NO: 18) | 13.7% | −1.24 | 22.39% |
| Test Example 1-9 | PRT699 (SEQ ID NO: 19) | 3.6% | −0.78 | 18.18% |
| Test Example 1-10 | PRT698 (SEQ ID NO: 20) | 0.0% | −0.03 | 16.24% |

It has been found that the water absorbency of the film is reduced as the glutamine residue content is reduced and the waterproofness is improved.

Test Example 2

[(1) Production of Modified Fibroin]

The lyophilized powder of the modified fibroin was obtained in the same procedure as in Test Example 1 except that a modified fibroin having the amino acid sequence set forth in SEQ ID NO: 23 (PRT917) and a modified fibroin having the amino acid sequence set forth in SEQ ID NO: 24 (PRT1028) were designed as the modified fibroin.

[(2) Production of Raw Fiber]

Using DMSO in which lithium chloride was dissolved to be 4 mass % as a solvent, the lyophilized powder of modified fibroin was added to the solvent so that the concentration thereof was 24 mass %. After dissolving with an aluminum block heater at 90° C. for 1 hour, insoluble matters and bubbles were removed to obtain a doping liquid (spinning raw liquid).

The doping liquid was filled into a reserve tank and discharged from a monohole nozzle having a diameter of 0.3 mm into a coagulation bath (coagulation bath temperature 12° C.) containing 100 mass % methanol using a gear pump. After coagulation, washing and drawing were performed in the coagulation bath containing 100 mass % methanol. After washing and drawing, the obtained raw yarn (raw fiber) was dried using a dry heat plate (drying temperature 80° C.) and wound up. The drawing ratio was 6 times.

[(3) Production of Artificially Modified Fibroin Fiber]

Each of the raw fiber was arranged to have a length of about 30 cm and bundled to form a raw fiber bundle having a fineness of 150 denier. With 0.8 g of lead weight being attached to each of the raw fiber bundle, the raw fiber bundle was immersed to be shrunk in water at 40° C. for 10 minutes (contact step) and taken out of water. With 0.8 g of lead weight being attached to each of the raw fiber bundle, the raw fiber bundle was dried at room temperature for 2 hours (drying step) to obtain the artificially modified fibroin fibers in Test Example 2-1 and Test Example 2-2, each of which had different protein types.

[(4) Evaluation of Artificially Modified Fibroin Fiber (Water Stretchability)]

The lengths of the artificially modified fibroin fibers when wetted (lengths of artificially modified fibroin fibers before being wetted) in Test Example 2-1 and Test Example 2-2 obtained in (3) were measured. With 0.8 g of lead weight being attached to each of the artificially modified fibroin fiber, the raw fiber bundle was immersed in water at 40° C. for 10 minutes. Thereafter, the length of each of the artificially modified fibroin fiber (length of the artificially modified fibroin fiber when wetted) was measured in water. The length measurement of each of the artificially modified fibroin fiber was carried out in water with 0.8 g of lead weight being attached to each of the artificially modified fibroin fiber in order to eliminate curling of each of the artificially modified fibroin fiber. Next, each of the artificially modified fibroin fiber taken out of water was dried at room temperature for 2 hours with a 0.8 g lead weight being attached. After drying, the length of each of the artificially modified fibroin fiber (length of the artificially modified fibroin fiber when dried from wetted state) was measured. The restoration rate, the elongation rate, and shrinkage rate C of each of the artificially modified fibroin fiber were calculated from the obtained measured values according to Expression (1), Expression (4), and Expression (5). The results are shown in Table. 9.

restoration rate=(length of artificially modified fibroin fiber when dried from wetted state/ length of artificially modified fibroin fiber before being wetted)×100(%)　　　Expression (1):

elongation rate={(length of artificially modified
fibroin fiber when wetted/length of artificially
modified fibroin fiber before being wetted)−1}×
100(%)  Expression (4):

shrinkage rate C={1−(length of artificially modified
fibroin fiber when dried from wetted state/
length of artificially modified fibroin fiber when
wetted)}×100(%)  Expression (5):

TABLE 9

|  |  | Elongation rate (%) | Shrinkage rate C (%) | Restoration rate (%) |
|---|---|---|---|---|
| Test Example 2-1 | PRT917 | 2.3 | 4 | 98.2 |
| Test Example 2-2 | PRT1028 | 4.9 | 5.6 | 99 |

As shown in Table 9, the artificially modified fibroin fiber including the modified fibroin having a reduced glutamine residue content (Test Example 2-1 and Test Example 2-2) has the characteristic that it elongates when wetted and then restore the original length when dried (restoration rate is 98.2 to 99%). In addition, the artificially modified fibroin fiber (Test Example 2-1 and Test Example 2-2) has both a low elongation rate and a low shrinkage rate C, and a dimensional change due to contact with water (and subsequent drying) is suppressed.

[(2) Production of Raw Fiber]

Using DMSO in which lithium chloride was dissolved to be 4.0 mass % as a solvent, the lyophilized powder of modified fibroin was added to the solvent so that the concentration thereof was 18 mass % or 24 mass % (see Table 10), and dissolved for 3 hours using a shaker. Thereafter, insoluble matters and bubbles were removed to obtain a modified fibroin liquid.

Using the obtained modified fibroin liquid as a doping liquid (spinning raw liquid), the raw fiber spun and drawn were produced by dry-wet-type spinning using a spinning device corresponding to the spinning device 10 shown in FIG. 3 The spinning device used is a spinning device 10 shown in FIG. 3 further provided with a second undrawn yarn production device (second bath) between an undrawn yarn production device 2 (first bath) and an wet heat drawing device 3 (third bath). The dry-wet-type spinning conditions are as follows.

Extrusion nozzle diameter: 0.2 mm

Liquid and temperature in the first to third baths: see Table 10

Total drawing ratio: see Table 10

Drying temperature: 60° C.

TABLE 10

| | Doping liquid | | First bath | | Second bath | | Third bath | | Total drawing |
|---|---|---|---|---|---|---|---|---|---|
| | Modified fibroin | Concentration (mass %) | Liquid | Temperature (° C.) | Liquid | Temperature (° C.) | Liquid | Temperature (C.) | ratio (times) |
| Production Example 1 | PRT799 | 24 | 100% Methanol | −5 | 100% Methanol | 16 | Water | 17 | 1 |
| Production Example 2 | | | | | | | | | 2 |
| Production Example 3 | | | | | | | | | 3 |
| Production Example 4 | | | | | | | | | 4 |
| Production Example 5 | | 18 | | | | | | | 1 |
| Production Example 6 | | | | | | | | | 2 |
| Production Example 7 | | | | | | | | | 3 |
| Production Example 8 | | | | | | | | | 4 |
| Production Example 9 | PRT410 | 24 | | −11 | | 14 | | | 1 |
| Production Example 10 | | | | | | | | | 2 |
| Production Example 11 | | | | | | | | | 3 |
| Production Example 12 | | | | | | | | | 4 |
| Production Example 13 | PRT399 | | | | | | | | 1 |
| Production Example 14 | | | | | | | | | 2 |
| Production Example 15 | | | | | | | | | 3 |
| Production Example 16 | PRT380 | | | | | | | 11 | 1 |
| Production Example 17 | | | | | | | | | 2 |
| Production Example 18 | | | | | | | | | 3 |
| Production Example 19 | | | | | | | | | 4 |

Test Example 3

[(1) Production of Modified Fibroin]

The lyophilized powder of the modified fibroin was obtained in the same procedure as in Test Example 1 except that a modified fibroin having the amino acid sequence set forth in SEQ ID NO: 42 (PRT399), a modified fibroin having the amino acid sequence set forth in SEQ ID NO: 36 (PRT380), a modified fibroin having the amino acid sequence set forth in SEQ ID NO: 37 (PRT410), and a modified fibroin having the amino acid sequence set forth in SEQ ID NO: 39 (PRT799) were designed as the modified fibroin.

[(3) Production of Artificially Modified Fibroin Fiber and Evaluation of Shrinkage Rate A and Shrinkage Rate B]

The artificially modified fibroin fiber was produced by subjecting each raw fiber obtained in Production Examples 1 to 19 to the contact step of bring the raw fiber into contact with water, or the drying step of drying the raw fiber at room temperature after completion of the contact step.

<Evaluation of Shrinkage Rate A in Contact Step>

A plurality of raw fibers each having a length of 30 cm were cut from the wound raw fibers obtained in Production Examples 1 to 19. The plurality of raw fibers were bundled to form a raw fiber bundle having a fineness of 150 denier. With 0.8 g of lead weight being attached to each raw fiber bundle, each raw fiber bundle was immersed in water for 10 minutes at a temperature shown in Tables 11 to 14 (contact step). Thereafter, the length of each raw fiber bundle was measured in water. The length measurement of the raw fiber bundle in water was carried out with 0.8 g lead weight being attached to the raw fiber bundle in order to eliminate curling of the raw fiber bundle. Next, the shrinkage rate A (%) of each raw fiber was calculated according to Expression (2). In Expression (2), L0 represents the length of the fiber before contact with water and after spinning, and here L0 is 30 cm. Similarly, in Expression (2), Lw represents the length of the fiber irreversibly shrunk due to contact with water after spinning, and here L0 is the length of each raw fiber bundle measured in water.

shrinkage rate $A=\{1-(Lw/L0)\}\times100(\%)$  Expression (2):

<Evaluation of Shrinkage Rate B in Drying Step>

After completion of contact step, the raw fiber bundle was taken out of water. The raw fiber bundle taken out was dried at room temperature for 2 hours with 0.8 g lead weight being attached (drying step) to obtain the artificially modified fibroin fiber. After drying, the length of each the artificially modified fibroin fiber bundle was measured. Next, the shrinkage rate B (%) of each of the artificially modified fibroin fiber was calculated according to Expression (3). In Expression (3), L0 represents the length of the fiber before contact with water and after spinning, and here L0 is 30 cm. Similarly, in Expression (3), Lwd represents the length of the fiber irreversibly shrunk due to contact with water after spinning and then further shrunk by drying, and here L0 is the length of each of the artificially modified fibroin fiber measured after drying.

shrinkage rate $B=\{1-(Lwd/L0)\}\times100(\%)$  Expression (3):

The results are shown in Tables 11 to 14.

TABLE 11

| Raw fiber/artificially modified fibroin fiber | Water temperature (° C.) | Shrinkage rate A (%) | Shrinkage rate B (%) |
|---|---|---|---|
| Production Example 1   24 wt % PRT799 ×1 | 20 | 0.0 | 7.8 |
| Production Example 2   24 wt % PRT799 ×2 |  | −1.2 | 10.3 |
| Production Example 3   24 wt % PRT799 ×3 |  | 7.2 | 21.2 |
| Production Example 4   24 wt % PRT799 ×4 |  | 13.5 | 26.3 |
| Production Example 6   18 wt % PRT799 ×2 |  | −2.3 | 9.5 |
| Production Example 7   18 wt % PRT799 ×3 |  | 6.0 | 19.7 |
| Production Example 8   18 wt % PRT799 ×4 |  | 14.3 | 27.5 |
| Production Example 2   24 wt % PRT799 ×2 | 40 | −5.3 | 7.2 |
| Production Example 3   24 wt % PRT799 ×3 |  | 8.7 | 21.3 |
| Production Example 4   24 wt % PRT799 ×4 |  | 14.5 | 26.0 |
| Production Example 6   18 wt % PRT799 ×2 |  | −4.3 | 7.3 |
| Production Example 7   18 wt % PRT799 ×3 |  | 6.2 | 18.3 |
| Production Example 8   18 wt % PRT799 ×4 |  | 16.0 | 28.7 |
| Production Example 3   24 wt % PRT799 ×3 | 60 | 6.8 | 21.0 |
| Production Example 4   24 wt % PRT799 ×4 |  | 15.0 | 27.5 |
| Production Example 6   18 wt % PRT799 ×2 |  | −1.5 | 10.7 |
| Production Example 7   18 wt % PRT799 ×3 |  | 3.3 | 18.2 |
| Production Example 8   18 wt % PRT799 ×4 |  | 16.2 | 29.0 |

TABLE 12

| Raw fiber/artificially modified fibroin fiber | Water temperature (° C.) | Shrinkage rate A (%) | Shrinkage rate B (%) |
|---|---|---|---|
| Production Example 10   24 wt % PRT410 ×2 | 20 | −2.3 | 8.7 |
| Production Example 11   24 wt % PRT410 ×3 |  | 4.7 | 16.7 |
| Production Example 12   24 wt % PRT410 ×4 |  | 10.3 | 22.3 |
| Production Example 11   24 wt % PRT410 ×3 | 40 | 4.7 | 17.5 |
| Production Example 12   24 wt % PRT410 ×4 |  | 11.5 | 24.0 |
| Production Example 11   24 wt % PRT410 ×3 | 60 | 2.0 | 16.5 |
| Production Example 12   24 wt % PRT410 ×4 |  | 10.8 | 25.0 |

TABLE 13

| Raw fiber/artificially modified fibroin fiber | Water temperature (° C.) | Shrinkage rate A (%) | Shrinkage rate B (%) |
|---|---|---|---|
| Production Example 13   24 wt % PRT399 ×1 | 20 | −3.5 | 7.6 |
| Production Example 14   24 wt % PRT399 ×2 |  | 3.7 | 12.5 |
| Production Example 15   24 wt % PRT399 ×3 | 40 | 7.0 | 16.8 |
| Production Example 14   24 wt % PR1399 ×2 |  | 3.0 | 12.7 |
| Production Example 15   24 wt % PRT399 ×3 | 60 | 7.3 | 16.7 |
| Production Example 14   24 wt % PRT399 ×2 |  | 3.3 | 9.3 |
| Production Example 15   24 wt % PRT399 ×3 |  | 6.8 | 14.2 |

TABLE 14

| Raw fiber/artificially modified fibroin fiber | Water temperature (° C.) | Shrinkage rate A (%) | Shrinkage rate B (%) |
|---|---|---|---|
| Production Example 16 24 wt % PRT380 ×1 | 20 | −1.1 | 9.4 |
| Production Example 17 24 wt % PRT380 ×2 |  | 2.7 | 13.3 |
| Production Example 18 24 wt % PRT380 ×3 |  | 7.0 | 17.7 |
| Production Example 19 24 wt % PRT380 ×4 |  | 10.0 | 20.2 |
| Production Example 17 24 wt % PRT380 ×2 | 40 | 3.3 | 14.2 |
| Production Example 18 24 wt % PRT380 ×3 |  | 7.7 | 19.0 |
| Production Example 19 24 wt % PRT380 ×4 |  | 12.0 | 22.0 |
| Production Example 17 24 wt % PRT380 ×2 | 60 | 2.7 | 14.3 |
| Production Example 18 24 wt % PRT380 ×3 |  | 8.2 | 20.3 |
| Production Example 19 24 wt % PRT380 ×4 |  | 12.0 | 23.2 |

REFERENCE SIGNS LIST

1 . . . extrusion device, 2 . . . undrawn yarn production device, 3 . . . wet heat drawing device, 4 . . . drying device, 6 . . . doping liquid, 10 . . . spinning device, 20 . . . coagulation liquid bath, 21 . . . drawing bath, 36 . . . raw fiber.

---

The invention claimed is:

1. A modified fibroin, comprising:
a domain sequence represented by Formula 1: [(A)$_n$ motif-REP]$_m$ or Formula 2: [(A)$_n$ motif-REP]$_m$–(A)$_n$ motif, wherein the domain sequence has an amino acid sequence equivalent with a reduced content of a glutamine residue to an amino acid in which one or a plurality of glutamine residues in REP are deleted or substituted with other amino acid residues, as compared with a naturally occurring fibroin wherein in Formula 1 and Formula 2, (A)$_n$ motif represents an amino acid sequence consisting of 4 to 27 amino acid residues and the number of alanine residues with respect to the total number of amino acid residues in the (A)$_n$ motif is 80% or more,
REP represents an amino acid sequence consisting of 10 to 200 amino acid residues and contains a GPGXX (where X represents an amino acid residue other than a glycine residue) motif and has a GPGXX motif content of 10% or more, wherein an increase in the GPGXX motif content increases tensile strength and elasticity,
m represents an integer of 10 to 300,
a plurality of (A)$_n$ motifs may be the same amino acid sequence or different amino acid sequences, and
a plurality of REPs may be the same amino acid sequence or different amino acid sequences.

2. The modified fibroin according to claim 1, wherein a glutamine residue content rate is 9% or less.

3. The modified fibroin according to claim 1, wherein the other amino acid residues are amino acid residues selected from the group consisting of isoleucine (I), valine (V), leucine (L), phenylalanine (F), cysteine (C), methionine (M), alanine (A), glycine (G), threonine (T), serine (S), tryptophan (W), tyrosine (Y), proline (P) and histidine (H).

4. The modified fibroin according to claim 1, wherein a hydrophobicity of the REP is −0.8 or more.

5. The modified fibroin according to claim 1, further comprising:
an amino acid sequence equivalent to an amino acid sequence in which one or a plurality of amino acid residues are substituted, deleted, inserted and/or added, as compared with the naturally occurring fibroin.

6. The modified fibroin according to claim 5, wherein the naturally occurring fibroin is a fibroin derived from insects or spiders.

7. The modified fibroin according to claim 6, wherein the naturally occurring fibroin is a major ampullate spider protein (MaSp) or minor ampullate spider protein (MiSp) of spiders.

8. A modified fibroin according to claim 1, comprising:
an amino acid sequence set forth in SEQ ID NO: 2, SEQ ID NO: 3, SEQ ID NO: 4, SEQ ID NO: 5, SEQ ID NO: 6, SEQ ID NO: 16, or SEQ ID NO: 17; or
an amino acid sequence having 90% or more sequence identity with the amino acid sequence set forth in SEQ ID NO: 2, SEQ ID NO: 3, SEQ ID NO: 4, SEQ ID NO: 5, SEQ ID NO: 6, SEQ ID NO: 16, or SEQ ID NO: 17.

9. A modified fibroin according to claim 1, comprising:
an amino acid sequence set forth in SEQ ID NO: 9, SEQ ID NO: 10, SEQ ID NO: 11, SEQ ID NO: 12, SEQ ID NO: 13, SEQ ID NO: 19, or SEQ ID NO: 20; or
an amino acid sequence having 90% or more sequence identity with the amino acid sequence set forth in SEQ ID NO: 9, SEQ ID NO: 10, SEQ ID NO: 11, SEQ ID NO: 12, SEQ ID NO: 13, SEQ ID NO: 19, or SEQ ID NO: 20.

10. A product comprising the modified fibroin according to claim 1, the product being selected from the group consisting of a fiber, a yarn, a film, a foam, a grain, a nanofibril, a gel, and a resin.

11. An artificially modified fibroin fiber comprising the modified fibroin according to claim 1,
wherein the artificially modified fibroin fiber elongates when wetted and shrinks when dried from the wetted state.

12. The artificially modified fibroin fiber according to claim 11, wherein a restoration rate is 95% or more as defined by restoration rate=(length of artificially modified fibroin fiber when dried from wetted state/length of artificially modified fibroin fiber before being wetted)×100(%).

13. The artificially modified fibroin fiber according to claim 11, wherein the artificially modified fibroin fiber is a fiber having a shrinkage history of irreversibly being shrunk by contact with water after spinning and a shrinkage rate A of 2% or more as defined by shrinkage rate A={1−(length of fiber irreversibly shrunk by contact with water after spinning/length of fiber before contact with water and after spinning)}×100(%).

14. The artificially modified fibroin fiber according to claim 11, wherein the artificially modified fibroin fiber is a fiber having a shrinkage history of irreversibly being shrunk by contact with water after spinning and then further being shrunk by drying and a shrinkage rate B of more than 7% as defined by shrinkage rate B={1−(length of fiber irreversibly shrunk by contact with water after spinning and then further shrunk by drying/length of fiber before contact with water and after spinning)}×100(%).

15. An artificially modified fibroin fiber comprising a modified fibroin, wherein the artificially modified fibroin fiber elongates when wetted and shrinks when dried from the wetted state, and the modified fibroin is the modified fibroin according to claim 1.

16. The artificially modified fibroin fiber according to claim 11, wherein an elongation rate is 17% or less as defined by elongation rate={(length of artificially modified fibroin fiber when wetted/length of artificially modified fibroin fiber before being wetted)−1}×100(%).

17. The artificially modified fibroin fiber according to claim 11, wherein a shrinkage rate C is 17% or less as defined by shrinkage rate C={1−(length of artificially modified fibroin fiber when dried from wetted state/length of artificially modified fibroin fiber when wetted)}×100(%).

18. A method for producing an artificially modified fibroin fiber, the method comprising:
a shrinking step of bring a raw fiber before contact with water and after spinning into contact with water to cause irreversible shrinkage, and then drying the raw fiber to cause further shrinkage,
wherein the raw fiber includes the modified fibroin according to claim 1.

19. The production method according to claim 18, wherein a shrinkage rate A of the raw fiber is 2% or more as defined by shrinkage rate A={1−(length of fiber irreversibly shrunk by contact with water after spinning/length of fiber before contact with water and after spinning)}×100(%).

20. The production method according to claim 18, wherein a shrinkage rate B of the raw fiber defined by Expression (3) is more than 7% as defined by shrinkage rate B={1−(length of fiber irreversibly shrunk by contact with water after spinning and then further shrunk by drying/length of fiber before contact with water and after spinning)}×100(%).

21. A method for producing an artificially modified fibroin fiber, the method comprising:
a shrinkage step of bring a raw fiber before contact with water and after spinning into contact with water to cause irreversible shrinkage, and then drying the raw fiber to cause further shrinkage,
wherein the raw fiber includes a modified fibroin,
wherein the modified fibroin is the modified fibroin according to claim 1.

22. A modified fibroin, comprising:
a domain sequence represented by Formula 1: $[(A)_n$ motif-REP]m or Formula 2: $[(A)_n$ motif-REP]$_m$-$(A)_n$ motif,
wherein a glutamine residue content rate is 9% or less,
wherein a hydrophobicity of the REP is −0.8 or more,
wherein in Formula 1 and Formula 2, $(A)_n$ motif represents an amino acid sequence consisting of 4 to 27 amino acid residues and the number of alanine residues with respect to the total number of amino acid residues in the $(A)_n$ motif is 80% or more, REP represents an amino acid sequence consisting of 10 to 200 amino acid residues, m represents an integer of 10 to 300, a plurality of $(A)_n$ motifs may be the same amino acid sequence or different amino acid sequences, and a plurality of REPs may be the same amino acid sequence or different amino acid sequences, wherein an increase in the $(A)_n$ motif content increases tensile strength and elasticity.

23. A modified fibroin, comprising:
a domain sequence represented by Formula 1: [(A)$_n$ motif-REP]$_m$ or Formula 2: [(A)$_n$ motif-REP]$_m$–(A)$_n$ motif,
wherein a glutamine residue content rate is 9% or less,
wherein the REP contains a GPGXX (where X represents an amino acid residue other than a glycine residue) motif and has a GPGXX motif content of 10% or more, and an increase in the GPGXX motif content increases tensile strength and elasticity,
wherein in Formula 1 and Formula 2, (A)$_n$ motif represents an amino acid sequence consisting of 4 to 27 amino acid residues and the number of alanine residues with respect to the total number of amino acid residues in the (A)$_n$ motif is 80% or more, REP represents an amino acid sequence consisting of 10 to 200 amino acid residues, m represents an integer of 10 to 300, a plurality of (A)$_n$ motifs may be the same amino acid sequence or different amino acid sequences, and a plurality of REPs may be the same amino acid sequence or different amino acid sequences.

\* \* \* \* \*

SEQUENCE LISTING

<160> NUMBER OF SEQ ID NOS: 48

<210> SEQ ID NO 1
<211> LENGTH: 590
<212> TYPE: PRT
<213> ORGANISM: Artificial Sequence
<220> FEATURE:
<223> OTHER INFORMATION: M_PRT410

<400> SEQUENCE: 1

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
    195                 200                 205

Ser Gly Gln Gln Gly Pro Gly Gln Gly Pro Tyr Ala Ser Ala Ala
210                 215                 220

```
Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
        260                 265                 270

Tyr Gly Pro Gly Gln Gln Gly Pro Gln Ser Ala Ala Ala Ala
    275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Ala Gly Gln Tyr Gly Pro Gly Gln Gln Gly Pro
        340                 345                 350

Tyr Gly Pro Gly Gln Ser Ala Ala Ala Ala Gly Gln Tyr Gln Gln
    355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
    435                 440                 445

Tyr Gly Pro Gly Ala Ser Ala Ala Ala Ala Gly Gln Tyr Gly Pro
    450                 455                 460

Gly Gln Gln Gly Pro Tyr Gly Pro Gly Ser Ala Ala Ala Ala
465                 470                 475                 480

Gly Pro Gly Ser Gly Gln Tyr Gly Pro Gly Ala Ser Gly Gln Asn Gly
            485                 490                 495

Pro Gly Ser Gly Gln Tyr Gly Pro Gly Gln Gln Gly Pro Gly Gln Ser
        500                 505                 510

Ala Ala Ala Ala Gly Gln Tyr Gln Gln Gly Pro Gly Gln Gln Gly
    515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala
            565                 570                 575

Ala Ala Gly Pro Gly Ser Gly Gln Gln Gly Pro Gly Ala Ser
            580                 585                 590

<210> SEQ ID NO 2
<211> LENGTH: 590
<212> TYPE: PRT
<213> ORGANISM: Artificial Sequence
<220> FEATURE:
<223> OTHER INFORMATION: M_PRT888

<400> SEQUENCE: 2
```

```
Met Gly Pro Gly Val Leu Gly Pro Tyr Gly Pro Gly Ala Ser Ala Ala
1               5                   10                  15

Ala Ala Ala Gly Gln Asn Gly Pro Gly Ser Gly Val Leu Gly Pro Gly
            20                  25                  30

Gln Ser Gly Gln Tyr Gly Pro Gly Val Leu Gly Pro Gly Val Leu Gly
        35                  40                  45

Pro Gly Ser Ser Ala Ala Ala Ala Gly Pro Gly Gln Tyr Gly Pro
    50                  55                  60

Gly Val Leu Gly Pro Ser Ala Ser Ala Ala Ala Ala Gly Pro Gly
65                  70                  75                  80

Ser Gly Val Leu Gly Pro Gly Ala Ser Gly Gln Tyr Gly Pro Gly Val
                85                  90                  95

Leu Gly Pro Gly Val Leu Gly Pro Gly Ser Ser Ala Ala Ala Ala
                100                 105                 110

Gly Gln Tyr Gly Ser Gly Pro Gly Val Leu Gly Pro Tyr Gly Ser Ala
        115                 120                 125

Ala Ala Ala Gly Pro Gly Ser Gly Gln Tyr Gly Gln Gly Pro Tyr
130                 135                 140

Gly Pro Gly Ala Ser Gly Pro Gly Gln Tyr Gly Pro Gly Val Leu Gly
145                 150                 155                 160

Pro Ser Ala Ser Ala Ala Ala Ala Gly Ser Gly Val Leu Gly Pro
        165                 170                 175

Gly Gln Tyr Gly Pro Tyr Ala Ser Ala Ala Ala Ala Gly Gln Tyr
        180                 185                 190

Gly Ser Gly Pro Gly Val Leu Gly Pro Tyr Gly Pro Gly Gln Ser Gly
        195                 200                 205

Ser Gly Val Leu Gly Pro Gly Val Leu Gly Pro Tyr Ala Ser Ala Ala
        210                 215                 220

Ala Ala Ala Gly Pro Gly Val Leu Gly Pro Tyr Gly Pro Gly Ser Ser
225                 230                 235                 240

Ala Ala Ala Ala Ala Gly Gln Tyr Gly Tyr Gly Pro Gly Val Leu Gly
            245                 250                 255

Pro Tyr Gly Pro Gly Ala Ser Gly Gln Asn Gly Pro Gly Ser Gly Gln
        260                 265                 270

Tyr Gly Pro Gly Val Leu Gly Pro Gly Gln Ser Ala Ala Ala Ala
        275                 280                 285

Gly Pro Gly Val Leu Gly Pro Tyr Gly Pro Gly Ala Ser Ala Ala Ala
        290                 295                 300

Ala Ala Gly Gln Tyr Gly Pro Gly Val Leu Gly Pro Gly Gln Tyr Gly
305                 310                 315                 320

Pro Gly Ser Ser Gly Pro Gly Val Leu Gly Pro Tyr Gly Pro Gly Ser
            325                 330                 335

Ser Ala Ala Ala Ala Gly Gln Tyr Gly Pro Gly Val Leu Gly Pro
        340                 345                 350

Tyr Gly Pro Gly Gln Ser Ala Ala Ala Ala Gly Gln Tyr Val Leu
        355                 360                 365

Gly Pro Gly Val Leu Gly Pro Tyr Gly Pro Gly Ala Ser Gly Pro Gly
        370                 375                 380

Val Leu Gly Pro Tyr Gly Pro Gly Ala Ser Ala Ala Ala Ala Gly
385                 390                 395                 400

Pro Gly Gln Tyr Gly Pro Gly Val Leu Gly Pro Ser Ala Ser Ala Ala
        405                 410                 415

Ala Ala Ala Gly Gln Tyr Gly Ser Gly Pro Gly Gln Tyr Gly Pro Tyr
```

```
                420                 425                 430
Gly Pro Gly Gln Ser Gly Pro Gly Val Leu Gly Gln Gly Pro
            435                 440                 445

Tyr Gly Pro Gly Ala Ser Ala Ala Ala Ala Gly Gln Tyr Gly Pro
450                 455                 460

Gly Val Leu Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Val Leu Gly Pro Gly Gln Ser
                500                 505                 510

Ala Ala Ala Ala Gly Gln Tyr Val Leu Gly Pro Gly Val Leu Gly
                515                 520                 525

Pro Tyr Gly Pro Gly Ala Ser Ala Ala Ala Ala Gly Gln Tyr Gly
                530                 535                 540

Ser Gly Pro Gly Val Leu Gly Pro Tyr Gly Pro Gly Gln Ser Gly Ser
545                 550                 555                 560

Gly Val Leu Gly Pro Gly Val Leu Gly Pro Tyr Ala Ser Ala Ala Ala
                565                 570                 575

Ala Ala Gly Pro Gly Ser Gly Val Leu Gly Pro Gly Ala Ser
                580                 585                 590

<210> SEQ ID NO 3
<211> LENGTH: 590
<212> TYPE: PRT
<213> ORGANISM: Artificial Sequence
<220> FEATURE:
<223> OTHER INFORMATION: M_PRT965

<400> SEQUENCE: 3

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
                20                  25                  30

Ala Ser Gly Ala Tyr Gly Pro Gly Thr Ser Gly Pro Gly Thr Ser Gly
            35                  40                  45

Pro Gly Ser Ser Ala Ala Ala Ala Gly Pro Gly Ala Tyr Gly Pro
    50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala
                100                 105                 110

Gly Ala Tyr Gly Ser Gly Pro Gly Thr Ser Gly Pro Tyr Gly Ser Ala
            115                 120                 125

Ala Ala Ala Ala Gly Pro Gly Ser Gly Ala Tyr Gly Ala Gly Pro Tyr
            130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Gly Ser Gly Thr Ser Gly Pro
                165                 170                 175

Gly Ala Tyr Gly Pro Tyr Ala Ser Ala Ala Ala Ala Gly Ala Tyr
            180                 185                 190

Gly Ser Gly Pro Gly Thr Ser Gly Pro Tyr Gly Pro Gly Ala Ser Gly
```

```
                195                 200                 205
Ser Gly Thr Ser Gly Pro Gly Thr Ser Gly Pro Tyr Ala Ser Ala Ala
    210                 215                 220

Ala Ala Ala Gly Pro Gly Thr Ser Gly Pro Tyr Gly Pro Gly Ser Ser
225                 230                 235                 240

Ala Ala Ala Ala Gly Ala Tyr Gly Tyr Gly Pro Gly Thr Ser Gly
                245                 250                 255

Pro Tyr Gly Pro Gly Ala Ser Gly Ala Asn Gly Pro Gly Ser Gly Ala
                260                 265                 270

Tyr Gly Pro Gly Thr Ser Gly Pro Gly Ala Ser Ala Ala Ala Ala
            275                 280                 285

Gly Pro Gly Thr Ser Gly Pro Tyr Pro Gly Ala Ser Ala Ala Ala
        290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
                325                 330                 335

Ser Ala Ala Ala Ala Gly Ala Tyr Gly Pro Gly Thr Ser Gly Pro
            340                 345                 350

Tyr Gly Pro Gly Ala Ser Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380

Thr Ser Gly Pro Tyr Gly Pro Gly Ala Ser Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
        435                 440                 445

Tyr Gly Pro Gly Ala Ser Ala Ala Ala Ala Gly Ala Tyr Gly Pro
        450                 455                 460

Gly Thr Ser Gly Pro Tyr Gly Pro Gly Ala Ser Ala Ala Ala Ala
465                 470                 475                 480

Gly Pro Gly Ser Gly Ala Tyr Gly Pro Gly Ala Ser Gly Ala Asn Gly
                485                 490                 495

Pro Gly Ser Gly Ala Tyr Gly Pro Gly Thr Ser Gly Pro Gly Ala Ser
            500                 505                 510

Ala Ala Ala Ala Gly Ala Tyr Thr Ser Gly Pro Gly Thr Ser Gly
        515                 520                 525

Pro Tyr Gly Pro Gly Ala Ser Ala Ala Ala Ala Gly Ala Tyr Gly
        530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala
                565                 570                 575

Ala Ala Gly Pro Gly Ser Gly Thr Ser Gly Pro Gly Ala Ser
            580                 585                 590

<210> SEQ ID NO 4
<211> LENGTH: 590
<212> TYPE: PRT
<213> ORGANISM: Artificial Sequence
```

<220> FEATURE:
<223> OTHER INFORMATION: M_PRT889

<400> SEQUENCE: 4

```
Met Gly Pro Gly Val Leu Gly Pro Tyr Gly Pro Gly Ala Ser Ala Ala
1               5                   10                  15

Ala Ala Ala Gly Ile Asn Gly Pro Ser Gly Val Leu Gly Pro Gly
            20                  25                  30

Ile Ser Gly Ile Tyr Gly Pro Gly Val Leu Gly Pro Gly Val Leu Gly
            35                  40                  45

Pro Gly Ser Ser Ala Ala Ala Ala Gly Pro Gly Ile Tyr Gly Pro
50                  55                  60

Gly Val Leu Gly Pro Ser Ala Ser Ala Ala Ala Ala Gly Pro Gly
65                  70                  75                  80

Ser Gly Val Leu Gly Pro Gly Ala Ser Gly Ile Tyr Gly Pro Gly Val
                85                  90                  95

Leu Gly Pro Gly Val Leu Gly Pro Gly Ser Ser Ala Ala Ala Ala
            100                 105                 110

Gly Ile Tyr Gly Ser Gly Pro Gly Val Leu Gly Pro Tyr Gly Ser Ala
            115                 120                 125

Ala Ala Ala Ala Gly Pro Gly Ser Gly Ile Tyr Gly Ile Gly Pro Tyr
130                 135                 140

Gly Pro Gly Ala Ser Gly Pro Gly Ile Tyr Gly Pro Gly Val Leu Gly
145                 150                 155                 160

Pro Ser Ala Ser Ala Ala Ala Ala Gly Ser Gly Val Leu Gly Pro
            165                 170                 175

Gly Ile Tyr Gly Pro Tyr Ala Ser Ala Ala Ala Ala Gly Ile Tyr
            180                 185                 190

Gly Ser Gly Pro Gly Val Leu Gly Pro Tyr Gly Pro Gly Ile Ser Gly
            195                 200                 205

Ser Gly Val Leu Gly Pro Gly Val Leu Gly Pro Tyr Ala Ser Ala Ala
210                 215                 220

Ala Ala Ala Gly Pro Gly Val Leu Gly Pro Tyr Gly Pro Gly Ser Ser
225                 230                 235                 240

Ala Ala Ala Ala Ala Gly Ile Tyr Gly Tyr Gly Pro Gly Val Leu Gly
                245                 250                 255

Pro Tyr Gly Pro Gly Ala Ser Gly Ile Asn Gly Pro Gly Ser Gly Ile
            260                 265                 270

Tyr Gly Pro Gly Val Leu Gly Pro Gly Ile Ser Ala Ala Ala Ala
            275                 280                 285

Gly Pro Gly Val Leu Gly Pro Tyr Gly Pro Gly Ala Ser Ala Ala Ala
            290                 295                 300

Ala Ala Gly Ile Tyr Gly Pro Gly Val Leu Gly Pro Gly Ile Tyr Gly
305                 310                 315                 320

Pro Gly Ser Ser Gly Pro Gly Val Leu Gly Pro Tyr Gly Pro Gly Ser
                325                 330                 335

Ser Ala Ala Ala Ala Gly Ile Tyr Gly Pro Gly Val Leu Gly Pro
            340                 345                 350

Tyr Gly Pro Gly Ile Ser Ala Ala Ala Ala Gly Ile Tyr Val Leu
            355                 360                 365

Gly Pro Gly Val Leu Gly Pro Tyr Gly Pro Gly Ala Ser Gly Pro Gly
            370                 375                 380

Val Leu Gly Pro Tyr Gly Pro Gly Ala Ser Ala Ala Ala Ala Gly
385                 390                 395                 400
```

```
Pro Gly Ile Tyr Gly Pro Gly Val Leu Gly Pro Ser Ala Ser Ala Ala
                405                 410                 415
Ala Ala Ala Gly Ile Tyr Gly Ser Gly Pro Gly Ile Tyr Gly Pro Tyr
            420                 425                 430
Gly Pro Gly Ile Ser Gly Pro Gly Ser Gly Val Leu Gly Ile Gly Pro
            435                 440                 445
Tyr Gly Pro Gly Ala Ser Ala Ala Ala Ala Gly Ile Tyr Gly Pro
450                 455                 460
Gly Val Leu Gly Pro Tyr Gly Pro Gly Ile Ser Ala Ala Ala Ala
465                 470                 475                 480
Gly Pro Gly Ser Gly Ile Tyr Gly Pro Gly Ala Ser Gly Ile Asn Gly
            485                 490                 495
Pro Gly Ser Gly Ile Tyr Gly Pro Gly Val Leu Gly Pro Gly Ile Ser
            500                 505                 510
Ala Ala Ala Ala Gly Ile Tyr Val Leu Gly Pro Gly Val Leu Gly
            515                 520                 525
Pro Tyr Gly Pro Gly Ala Ser Ala Ala Ala Ala Gly Ile Tyr Gly
530                 535                 540
Ser Gly Pro Gly Val Leu Gly Pro Tyr Gly Pro Gly Ile Ser Gly Ser
545                 550                 555                 560
Gly Val Leu Gly Pro Gly Val Leu Gly Pro Tyr Ala Ser Ala Ala Ala
            565                 570                 575
Ala Ala Gly Pro Gly Ser Gly Val Leu Gly Pro Gly Ala Ser
            580                 585                 590

<210> SEQ ID NO 5
<211> LENGTH: 590
<212> TYPE: PRT
<213> ORGANISM: Artificial Sequence
<220> FEATURE:
<223> OTHER INFORMATION: M_PRT916

<400> SEQUENCE: 5

Met Gly Pro Gly Val Ile Gly Pro Tyr Gly Pro Gly Ala Ser Ala Ala
1               5                   10                  15
Ala Ala Ala Gly Leu Asn Gly Pro Gly Ser Gly Val Ile Gly Pro Gly
            20                  25                  30
Leu Ser Gly Leu Tyr Gly Pro Gly Val Ile Gly Pro Gly Val Ile Gly
            35                  40                  45
Pro Gly Ser Ser Ala Ala Ala Ala Gly Pro Gly Leu Tyr Gly Pro
50                  55                  60
Gly Val Ile Gly Pro Ser Ala Ser Ala Ala Ala Ala Gly Pro Gly
65                  70                  75                  80
Ser Gly Val Ile Gly Pro Gly Ala Ser Gly Leu Tyr Gly Pro Gly Val
            85                  90                  95
Ile Gly Pro Gly Val Ile Gly Pro Gly Ser Ser Ala Ala Ala Ala
            100                 105                 110
Gly Leu Tyr Gly Ser Gly Pro Gly Val Ile Gly Pro Tyr Gly Ser Ala
            115                 120                 125
Ala Ala Ala Ala Gly Pro Gly Ser Gly Leu Tyr Gly Leu Gly Pro Tyr
            130                 135                 140
Gly Pro Gly Ala Ser Gly Pro Gly Leu Tyr Gly Pro Gly Val Ile Gly
145                 150                 155                 160
Pro Ser Ala Ser Ala Ala Ala Ala Gly Ser Gly Val Ile Gly Pro
            165                 170                 175
```

```
Gly Leu Tyr Gly Pro Tyr Ala Ser Ala Ala Ala Ala Gly Leu Tyr
            180                 185                 190
Gly Ser Gly Pro Gly Val Ile Gly Pro Tyr Gly Pro Gly Leu Ser Gly
        195                 200                 205
Ser Gly Val Ile Gly Pro Gly Val Ile Gly Pro Tyr Ala Ser Ala Ala
210                 215                 220
Ala Ala Ala Gly Pro Gly Val Ile Gly Pro Tyr Gly Pro Gly Ser Ser
225                 230                 235                 240
Ala Ala Ala Ala Ala Gly Leu Tyr Tyr Gly Pro Gly Val Ile Gly
            245                 250                 255
Pro Tyr Gly Pro Gly Ala Ser Gly Leu Asn Gly Pro Gly Ser Gly Leu
        260                 265                 270
Tyr Gly Pro Gly Val Ile Gly Pro Gly Leu Ser Ala Ala Ala Ala Ala
    275                 280                 285
Gly Pro Gly Val Ile Gly Pro Tyr Gly Pro Gly Ala Ser Ala Ala Ala
        290                 295                 300
Ala Ala Gly Leu Tyr Gly Pro Gly Val Ile Gly Pro Gly Leu Tyr Gly
305                 310                 315                 320
Pro Gly Ser Ser Gly Pro Gly Val Ile Gly Pro Tyr Gly Pro Gly Ser
            325                 330                 335
Ser Ala Ala Ala Ala Gly Leu Tyr Gly Pro Gly Val Ile Gly Pro
        340                 345                 350
Tyr Gly Pro Gly Leu Ser Ala Ala Ala Ala Ala Gly Leu Tyr Val Ile
    355                 360                 365
Gly Pro Gly Val Ile Gly Pro Tyr Gly Pro Gly Ala Ser Gly Pro Gly
        370                 375                 380
Val Ile Gly Pro Tyr Gly Pro Gly Ala Ser Ala Ala Ala Ala Gly
385                 390                 395                 400
Pro Gly Leu Tyr Gly Pro Gly Val Ile Gly Pro Ser Ala Ser Ala Ala
            405                 410                 415
Ala Ala Ala Gly Leu Tyr Gly Ser Gly Pro Gly Leu Tyr Gly Pro Tyr
        420                 425                 430
Gly Pro Gly Leu Ser Gly Pro Gly Ser Gly Val Ile Gly Leu Gly Pro
    435                 440                 445
Tyr Gly Pro Gly Ala Ser Ala Ala Ala Ala Gly Leu Tyr Gly Pro
        450                 455                 460
Gly Val Ile Gly Pro Tyr Gly Pro Gly Leu Ser Ala Ala Ala Ala
465                 470                 475                 480
Gly Pro Gly Ser Gly Leu Tyr Gly Pro Gly Ala Ser Gly Leu Asn Gly
            485                 490                 495
Pro Gly Ser Gly Leu Tyr Gly Pro Gly Val Ile Gly Pro Gly Leu Ser
        500                 505                 510
Ala Ala Ala Ala Ala Gly Leu Tyr Val Ile Gly Pro Gly Val Ile Gly
    515                 520                 525
Pro Tyr Gly Pro Gly Ala Ser Ala Ala Ala Ala Gly Leu Tyr Gly
        530                 535                 540
Ser Gly Pro Gly Val Ile Gly Pro Tyr Gly Pro Gly Leu Ser Gly Ser
545                 550                 555                 560
Gly Val Ile Gly Pro Gly Val Ile Gly Pro Tyr Ala Ser Ala Ala Ala
            565                 570                 575
Ala Ala Gly Pro Gly Ser Gly Val Ile Gly Pro Gly Ala Ser
        580                 585                 590
```

<210> SEQ ID NO 6
<211> LENGTH: 590
<212> TYPE: PRT
<213> ORGANISM: Artificial Sequence
<220> FEATURE:
<223> OTHER INFORMATION: M_ PRT918

<400> SEQUENCE: 6

```
Met Gly Pro Gly Val Phe Gly Pro Tyr Gly Pro Gly Ala Ser Ala Ala
1               5                   10                  15

Ala Ala Ala Gly Ile Asn Gly Pro Ser Gly Val Phe Gly Pro Gly
            20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Gly Pro Gly Ile Tyr Gly Pro
    50                  55                  60

Gly Val Phe Gly Pro Ser Ala Ser Ala Ala Ala Ala Gly Pro Gly
65              70                  75                  80

Ser Gly Val Phe Gly Pro Gly Ala Ser Gly Ile Tyr Gly Pro Gly Val
            85                  90                  95

Phe Gly Pro Gly Val Phe Gly Pro Gly Ser Ala Ala Ala Ala
            100                 105                 110

Gly Ile Tyr Gly Ser Gly Pro Gly Val Phe Pro Tyr Gly Ser Ala
        115                 120                 125

Ala Ala Ala Gly Pro Gly Ser Gly Ile Tyr Gly Ile Pro Tyr
            130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
            165                 170                 175

Gly Ile Tyr Gly Pro Tyr Ala Ser Ala Ala Ala Ala Gly Ile Tyr
        180                 185                 190

Gly Ser Gly Pro Gly Val Phe Gly Pro Tyr Gly Pro Gly Ile Ser Gly
        195                 200                 205

Ser Gly Val Phe Gly Pro Gly Val Phe Gly Pro Tyr Ala Ser Ala Ala
            210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala
        275                 280                 285

Gly Pro Gly Val Phe Gly Pro Tyr Gly Pro Gly Ala Ser Ala Ala
290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
            325                 330                 335

Ser Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
        355                 360                 365
```

-continued

```
Gly Pro Gly Val Phe Gly Pro Tyr Gly Pro Gly Ala Ser Gly Pro Gly
        370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Ser Gly Val Phe Gly Ile Gly Pro
            435                 440                 445

Tyr Gly Pro Gly Ala Ser Ala Ala Ala Ala Gly Ile Tyr Gly Pro
    450                 455                 460

Gly Val Phe Gly Pro Tyr Gly Pro Gly Ile Ser Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590
```

<210> SEQ ID NO 7
<211> LENGTH: 12
<212> TYPE: PRT
<213> ORGANISM: Artificial Sequence
<220> FEATURE:
<223> OTHER INFORMATION: HisTag

<400> SEQUENCE: 7

```
Met His His His His His Ser Ser Gly Ser Ser
1               5                   10
```

<210> SEQ ID NO 8
<211> LENGTH: 601
<212> TYPE: PRT
<213> ORGANISM: Artificial Sequence
<220> FEATURE:
<223> OTHER INFORMATION: PRT410

<400> SEQUENCE: 8

```
Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gly Pro Gly Ser Ser Ala
    50                  55                  60

Ala Ala Ala Gly Pro Gly Gln Tyr Gly Pro Gly Gln Gln Gly Pro
65                  70                  75                  80
```

```
Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
            290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gln Gly Pro Gly Gln Gln
            370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Gly Tyr Gly Pro Gly Gln Ser
                435                 440                 445

Gly Pro Gly Ser Gly Gln Gln Gly Gln Gly Pro Tyr Gly Pro Gly Ala
            450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495
```

```
Gln Tyr Gly Pro Gly Ala Ser Gly Gln Asn Pro Gly Ser Gly Gln
            500                 505                 510

Tyr Gly Pro Gly Gln Gln Gly Pro Gly Gln Ser Ala Ala Ala Ala
        515                 520                 525

Gly Gln Tyr Gln Gln Gly Pro Gly Gln Gln Pro Tyr Gly Pro Gly
        530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gly Pro
                565                 570                 575

Gly Gln Gln Gly Pro Tyr Ala Ser Ala Ala Ala Ala Gly Pro Gly
        580                 585                 590

Ser Gly Gln Gln Gly Pro Gly Ala Ser
        595                 600
```

<210> SEQ ID NO 9
<211> LENGTH: 601
<212> TYPE: PRT
<213> ORGANISM: Artificial Sequence
<220> FEATURE:
<223> OTHER INFORMATION: PRT888

<400> SEQUENCE: 9

```
Met His His His His His Ser Ser Gly Ser Ser Gly Pro Gly Val
1               5                   10                  15

Leu Gly Pro Tyr Gly Pro Gly Ala Ser Ala Ala Ala Ala Gly Gln
            20                  25                  30

Asn Gly Pro Gly Ser Gly Val Leu Gly Pro Gly Gln Ser Gly Gln Tyr
        35                  40                  45

Gly Pro Gly Val Leu Gly Pro Gly Val Leu Gly Pro Gly Ser Ser Ala
    50                  55                  60

Ala Ala Ala Ala Gly Pro Gly Gln Tyr Gly Pro Gly Val Leu Gly Pro
65                  70                  75                  80

Ser Ala Ser Ala Ala Ala Ala Gly Pro Gly Ser Gly Val Leu Gly
            85                  90                  95

Pro Gly Ala Ser Gly Gln Tyr Gly Pro Gly Val Leu Gly Pro Gly Val
                100                 105                 110

Leu Gly Pro Gly Ser Ser Ala Ala Ala Ala Gly Gln Tyr Gly Ser
            115                 120                 125

Gly Pro Gly Val Leu Gly Pro Tyr Gly Ser Ala Ala Ala Ala Gly
                130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Gly Ser Gly Val Leu Gly Pro Gly Gln Tyr Gly Pro
            180                 185                 190

Tyr Ala Ser Ala Ala Ala Ala Gly Gln Tyr Gly Ser Gly Pro Gly
        195                 200                 205

Val Leu Gly Pro Tyr Gly Pro Gly Gln Ser Gly Ser Gly Val Leu Gly
        210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
                245                 250                 255
```

```
Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Gly Pro Gly Val Leu
    290                 295                 300

Gly Pro Tyr Gly Pro Gly Ala Ser Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala Ala
            340                 345                 350

Ala Gly Gln Tyr Gly Pro Gly Val Leu Gly Pro Tyr Gly Pro Gly Gln
        355                 360                 365

Ser Ala Ala Ala Ala Gly Gln Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
            405                 410                 415

Pro Gly Val Leu Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
450                 455                 460

Ser Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
        500                 505                 510

Tyr Gly Pro Gly Val Leu Gly Pro Gly Gln Ser Ala Ala Ala Ala
            515                 520                 525

Gly Gln Tyr Val Leu Gly Pro Gly Val Leu Gly Pro Tyr Gly Pro Gly
530                 535                 540

Ala Ser Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
            565                 570                 575

Gly Val Leu Gly Pro Tyr Ala Ser Ala Ala Ala Ala Gly Pro Gly
            580                 585                 590

Ser Gly Val Leu Gly Pro Gly Ala Ser
        595                 600

<210> SEQ ID NO 10
<211> LENGTH: 601
<212> TYPE: PRT
<213> ORGANISM: Artificial Sequence
<220> FEATURE:
<223> OTHER INFORMATION: PRT965

<400> SEQUENCE: 10

Met His His His His His Ser Ser Gly Ser Ser Gly Pro Gly Thr
1               5                   10                  15
```

Ser Gly Pro Tyr Gly Pro Gly Ala Ser Ala Ala Ala Gly Ala
            20                  25                  30

Asn Gly Pro Gly Ser Gly Thr Ser Gly Pro Gly Ala Ser Gly Ala Tyr
            35                  40                  45

Gly Pro Gly Thr Ser Gly Pro Gly Thr Ser Gly Pro Gly Ser Ser Ala
50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Gly Pro Gly Ser Gly Thr Ser Gly
                85                  90                  95

Pro Gly Ala Ser Gly Ala Tyr Gly Pro Gly Thr Ser Gly Pro Gly Thr
                100                 105                 110

Ser Gly Pro Gly Ser Ser Ala Ala Ala Ala Gly Ala Tyr Gly Ser
            115                 120                 125

Gly Pro Gly Thr Ser Gly Pro Tyr Gly Ser Ala Ala Ala Ala Gly
            130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
            165                 170                 175

Ala Ala Ala Gly Ser Gly Thr Ser Gly Pro Gly Ala Tyr Gly Pro
            180                 185                 190

Tyr Ala Ser Ala Ala Ala Ala Gly Ala Tyr Gly Ser Gly Pro Gly
            195                 200                 205

Thr Ser Gly Pro Tyr Gly Pro Gly Ala Ser Gly Ser Gly Thr Ser Gly
210                 215                 220

Pro Gly Thr Ser Gly Pro Tyr Ala Ser Ala Ala Ala Ala Gly Pro
225                 230                 235                 240

Gly Thr Ser Gly Pro Tyr Gly Pro Gly Ser Ser Ala Ala Ala Ala
            245                 250                 255

Gly Ala Tyr Gly Tyr Gly Pro Gly Thr Ser Gly Pro Tyr Gly Pro Gly
            260                 265                 270

Ala Ser Gly Ala Asn Gly Pro Gly Ser Gly Ala Tyr Gly Pro Gly Thr
            275                 280                 285

Ser Gly Pro Gly Ala Ser Ala Ala Ala Ala Gly Pro Gly Thr Ser
290                 295                 300

Gly Pro Tyr Gly Pro Gly Ala Ser Ala Ala Ala Ala Gly Ala Tyr
305                 310                 315                 320

Gly Pro Gly Thr Ser Gly Pro Gly Ala Tyr Gly Pro Gly Ser Ser Gly
            325                 330                 335

Pro Gly Thr Ser Gly Pro Tyr Gly Pro Gly Ser Ser Ala Ala Ala Ala
            340                 345                 350

Ala Gly Ala Tyr Gly Pro Gly Thr Ser Gly Pro Tyr Gly Pro Gly Ala
            355                 360                 365

Ser Ala Ala Ala Ala Ala Gly Ala Tyr Thr Ser Pro Gly Thr Ser
370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Gly Pro Gly Ala Tyr Gly
            405                 410                 415

Pro Gly Thr Ser Gly Pro Ser Ala Ser Ala Ala Ala Ala Gly Ala
            420                 425                 430

Tyr Gly Ser Gly Pro Gly Ala Tyr Gly Pro Tyr Gly Pro Gly Ala Ser

```
                    435                 440                 445
Gly Pro Gly Ser Gly Thr Ser Gly Ala Gly Pro Tyr Gly Pro Gly Ala
            450                 455                 460
Ser Ala Ala Ala Ala Gly Ala Tyr Gly Pro Gly Thr Ser Gly Pro
465                 470                 475                 480
Tyr Gly Pro Gly Ala Ser Ala Ala Ala Gly Pro Gly Ser Gly
                485                 490                 495
Ala Tyr Gly Pro Gly Ala Ser Gly Ala Asn Gly Pro Gly Ser Gly Ala
            500                 505                 510
Tyr Gly Pro Gly Thr Ser Gly Pro Gly Ala Ser Ala Ala Ala Ala
            515                 520                 525
Gly Ala Tyr Thr Ser Gly Pro Gly Thr Ser Gly Pro Tyr Gly Pro Gly
            530                 535                 540
Ala Ser Ala Ala Ala Ala Gly Ala Tyr Gly Ser Gly Pro Gly Thr
545                 550                 555                 560
Ser Gly Pro Tyr Gly Pro Gly Ala Ser Gly Ser Gly Thr Ser Gly Pro
                565                 570                 575
Gly Thr Ser Gly Pro Tyr Ala Ser Ala Ala Ala Ala Gly Pro Gly
            580                 585                 590
Ser Gly Thr Ser Gly Pro Gly Ala Ser
        595                 600

<210> SEQ ID NO 11
<211> LENGTH: 601
<212> TYPE: PRT
<213> ORGANISM: Artificial Sequence
<220> FEATURE:
<223> OTHER INFORMATION: PRT889

<400> SEQUENCE: 11

Met His His His His His Ser Ser Gly Ser Ser Gly Pro Gly Val
1               5                   10                  15
Leu Gly Pro Tyr Gly Pro Gly Ala Ser Ala Ala Ala Ala Gly Ile
                20                  25                  30
Asn Gly Pro Gly Ser Gly Val Leu Gly Pro Gly Ile Ser Gly Ile Tyr
            35                  40                  45
Gly Pro Gly Val Leu Gly Pro Gly Val Leu Gly Pro Gly Ser Ser Ala
        50                  55                  60
Ala Ala Ala Gly Pro Gly Ile Tyr Gly Pro Gly Val Leu Gly Pro
65                  70                  75                  80
Ser Ala Ser Ala Ala Ala Ala Gly Pro Gly Ser Gly Val Leu Gly
                85                  90                  95
Pro Gly Ala Ser Gly Ile Tyr Gly Pro Gly Val Leu Gly Pro Gly Val
            100                 105                 110
Leu Gly Pro Gly Ser Ser Ala Ala Ala Ala Gly Ile Tyr Gly Ser
        115                 120                 125
Gly Pro Gly Val Leu Gly Pro Tyr Gly Ser Ala Ala Ala Ala Gly
            130                 135                 140
Pro Gly Ser Gly Ile Tyr Gly Ile Gly Pro Tyr Gly Pro Gly Ala Ser
145                 150                 155                 160
Gly Pro Gly Ile Tyr Gly Pro Gly Val Leu Gly Pro Ser Ala Ser Ala
                165                 170                 175
Ala Ala Ala Gly Ser Gly Val Leu Gly Pro Gly Ile Tyr Gly Pro
            180                 185                 190
Tyr Ala Ser Ala Ala Ala Ala Gly Ile Tyr Gly Ser Gly Pro Gly
```

```
            195                 200                 205
Val Leu Gly Pro Tyr Gly Pro Gly Ile Ser Gly Ser Gly Val Leu Gly
    210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
                245                 250                 255

Gly Ile Tyr Gly Tyr Gly Pro Gly Val Leu Gly Pro Tyr Gly Pro Gly
                260                 265                 270

Ala Ser Gly Ile Asn Gly Pro Gly Ser Gly Ile Tyr Gly Pro Gly Val
                275                 280                 285

Leu Gly Pro Gly Ile Ser Ala Ala Ala Ala Gly Pro Gly Val Leu
    290                 295                 300

Gly Pro Tyr Gly Pro Gly Ala Ser Ala Ala Ala Ala Gly Ile Tyr
305                 310                 315                 320

Gly Pro Gly Val Leu Gly Pro Gly Ile Tyr Gly Pro Gly Ser Ser Gly
                325                 330                 335

Pro Gly Val Leu Gly Pro Tyr Gly Pro Gly Ser Ser Ala Ala Ala
                340                 345                 350

Ala Gly Ile Tyr Gly Pro Gly Val Leu Gly Pro Tyr Gly Pro Gly Ile
                355                 360                 365

Ser Ala Ala Ala Ala Gly Ile Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Ile Tyr Gly
                405                 410                 415

Pro Gly Val Leu Gly Pro Ser Ala Ser Ala Ala Ala Ala Gly Ile
                420                 425                 430

Tyr Gly Ser Gly Pro Gly Ile Tyr Gly Pro Tyr Gly Pro Gly Ile Ser
                435                 440                 445

Gly Pro Gly Ser Gly Val Leu Gly Ile Gly Pro Tyr Gly Pro Gly Ala
    450                 455                 460

Ser Ala Ala Ala Ala Gly Ile Tyr Gly Pro Gly Val Leu Gly Pro
465                 470                 475                 480

Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
                500                 505                 510

Tyr Gly Pro Gly Val Leu Gly Pro Gly Ile Ser Ala Ala Ala Ala
                515                 520                 525

Gly Ile Tyr Val Leu Gly Pro Gly Val Leu Gly Pro Tyr Gly Pro Gly
                530                 535                 540

Ala Ser Ala Ala Ala Ala Gly Ile Tyr Gly Ser Gly Pro Gly Val
545                 550                 555                 560

Leu Gly Pro Tyr Gly Pro Gly Ile Ser Gly Ser Gly Val Leu Gly Pro
                565                 570                 575

Gly Val Leu Gly Pro Tyr Ala Ser Ala Ala Ala Ala Gly Pro Gly
                580                 585                 590

Ser Gly Val Leu Gly Pro Gly Ala Ser
        595                 600

<210> SEQ ID NO 12
```

<211> LENGTH: 601
<212> TYPE: PRT
<213> ORGANISM: Artificial Sequence
<220> FEATURE:
<223> OTHER INFORMATION: PRT916

<400> SEQUENCE: 12

Met His His His His His Ser Ser Gly Ser Ser Gly Pro Gly Val
1               5                   10                  15

Ile Gly Pro Tyr Gly Pro Gly Ala Ser Ala Ala Ala Ala Gly Leu
            20                  25                  30

Asn Gly Pro Gly Ser Gly Val Ile Gly Pro Gly Leu Ser Gly Leu Tyr
            35                  40                  45

Gly Pro Gly Val Ile Gly Pro Gly Val Ile Gly Pro Gly Ser Ser Ala
50                  55                  60

Ala Ala Ala Ala Gly Pro Gly Leu Tyr Gly Pro Gly Val Ile Gly Pro
65                  70                  75                  80

Ser Ala Ser Ala Ala Ala Ala Gly Pro Gly Ser Gly Val Ile Gly
            85                  90                  95

Pro Gly Ala Ser Gly Leu Tyr Gly Pro Gly Val Ile Gly Pro Gly Val
            100                 105                 110

Ile Gly Pro Gly Ser Ser Ala Ala Ala Ala Gly Leu Tyr Gly Ser
            115                 120                 125

Gly Pro Gly Val Ile Gly Pro Tyr Gly Ser Ala Ala Ala Ala Gly
130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
            165                 170                 175

Ala Ala Ala Gly Ser Gly Val Ile Gly Pro Gly Leu Tyr Gly Pro
            180                 185                 190

Tyr Ala Ser Ala Ala Ala Ala Gly Leu Tyr Gly Ser Gly Pro Gly
            195                 200                 205

Val Ile Gly Pro Tyr Gly Pro Gly Leu Ser Gly Ser Gly Val Ile Gly
            210                 215                 220

Pro Gly Val Ile Gly Pro Tyr Ala Ser Ala Ala Ala Ala Gly Pro
225                 230                 235                 240

Gly Val Ile Gly Pro Tyr Gly Pro Gly Ser Ser Ala Ala Ala Ala
            245                 250                 255

Gly Leu Tyr Gly Tyr Gly Pro Gly Val Ile Gly Pro Tyr Gly Pro Gly
            260                 265                 270

Ala Ser Gly Leu Asn Gly Pro Gly Ser Gly Leu Tyr Gly Pro Gly Val
            275                 280                 285

Ile Gly Pro Gly Leu Ser Ala Ala Ala Ala Gly Pro Gly Val Ile
            290                 295                 300

Gly Pro Tyr Gly Pro Gly Ala Ser Ala Ala Ala Ala Gly Leu Tyr
305                 310                 315                 320

Gly Pro Gly Val Ile Gly Pro Gly Leu Tyr Gly Pro Gly Ser Ser Gly
            325                 330                 335

Pro Gly Val Ile Gly Pro Tyr Gly Pro Gly Ser Ser Ala Ala Ala
            340                 345                 350

Ala Gly Leu Tyr Gly Pro Gly Val Ile Gly Pro Tyr Gly Pro Gly Leu
            355                 360                 365

Ser Ala Ala Ala Ala Gly Leu Tyr Val Ile Gly Pro Gly Val Ile
            370                 375                 380

-continued

Gly Pro Tyr Gly Pro Gly Ala Ser Gly Pro Gly Val Ile Gly Pro Tyr
385                 390                 395                 400

Gly Pro Gly Ala Ser Ala Ala Ala Ala Gly Pro Gly Leu Tyr Gly
                405                 410                 415

Pro Gly Val Ile Gly Pro Ser Ala Ala Ala Ala Gly Leu
            420                 425                 430

Tyr Gly Ser Gly Pro Gly Leu Tyr Gly Pro Tyr Gly Pro Gly Leu Ser
        435                 440                 445

Gly Pro Gly Ser Gly Val Ile Gly Leu Gly Pro Tyr Gly Pro Gly Ala
        450                 455                 460

Ser Ala Ala Ala Ala Gly Leu Tyr Gly Pro Gly Val Ile Gly Pro
465                 470                 475                 480

Tyr Gly Pro Gly Leu Ser Ala Ala Ala Ala Gly Pro Gly Ser Gly
                485                 490                 495

Leu Tyr Gly Pro Gly Ala Ser Gly Leu Asn Gly Pro Gly Ser Gly Leu
            500                 505                 510

Tyr Gly Pro Gly Val Ile Gly Pro Gly Leu Ser Ala Ala Ala Ala
        515                 520                 525

Gly Leu Tyr Val Ile Gly Pro Gly Val Ile Gly Pro Tyr Gly Pro Gly
530                 535                 540

Ala Ser Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Gly Pro Gly
            580                 585                 590

Ser Gly Val Ile Gly Pro Gly Ala Ser
            595                 600

<210> SEQ ID NO 13
<211> LENGTH: 601
<212> TYPE: PRT
<213> ORGANISM: Artificial Sequence
<220> FEATURE:
<223> OTHER INFORMATION: PRT918

<400> SEQUENCE: 13

Met His His His His His Ser Ser Gly Ser Gly Pro Gly Val
1               5                   10                  15

Phe Gly Pro Tyr Gly Pro Gly Ala Ser Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
        50                  55                  60

Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Gly Ile Tyr Gly Ser
        115                 120                 125

Gly Pro Gly Val Phe Gly Pro Tyr Gly Ser Ala Ala Ala Ala Gly
        130                 135                 140

```
Pro Gly Ser Gly Ile Tyr Gly Ile Gly Pro Tyr Pro Gly Ala Ser
145                 150                 155                 160

Gly Pro Gly Ile Tyr Gly Pro Gly Val Phe Gly Pro Ser Ala Ser Ala
            165                 170                 175

Ala Ala Ala Ala Gly Ser Gly Val Phe Gly Pro Gly Ile Tyr Gly Pro
        180                 185                 190

Tyr Ala Ser Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
        210                 215                 220

Pro Gly Val Phe Gly Pro Tyr Ala Ser Ala Ala Ala Ala Gly Pro
225                 230                 235                 240

Gly Val Phe Gly Pro Tyr Gly Pro Gly Ser Ser Ala Ala Ala Ala
            245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Gly Pro Gly Val Phe
290                 295                 300

Gly Pro Tyr Gly Pro Gly Ala Ser Ala Ala Ala Ala Gly Ile Tyr
305                 310                 315                 320

Gly Pro Gly Val Phe Gly Pro Gly Ile Tyr Gly Pro Gly Ser Ser Gly
            325                 330                 335

Pro Gly Val Phe Gly Pro Tyr Gly Pro Gly Ser Ser Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Gly Pro Gly Ile Tyr Gly
            405                 410                 415

Pro Gly Val Phe Gly Pro Ser Ala Ser Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Gly Ile Tyr Gly Pro Gly Val Phe Gly Pro
465                 470                 475                 480

Tyr Gly Pro Gly Ile Ser Ala Ala Ala Ala Gly Pro Gly Ser Gly
            485                 490                 495

Ile Tyr Gly Pro Gly Ala Ser Gly Ile Asn Gly Pro Gly Ser Gly Ile
        500                 505                 510

Tyr Gly Pro Gly Val Phe Gly Pro Gly Ile Ser Ala Ala Ala Ala
        515                 520                 525

Gly Ile Tyr Val Phe Gly Pro Gly Val Phe Gly Pro Tyr Gly Pro Gly
        530                 535                 540

Ala Ser Ala Ala Ala Ala Gly Ile Tyr Gly Ser Gly Pro Gly Val
545                 550                 555                 560
```

Phe Gly Pro Tyr Gly Pro Gly Ile Ser Ser Gly Val Phe Gly Pro
                565                 570                 575

Gly Val Phe Gly Pro Tyr Ala Ser Ala Ala Ala Ala Gly Pro Gly
            580                 585                 590

Ser Gly Val Phe Gly Pro Gly Ala Ser
        595                 600

<210> SEQ ID NO 14
<211> LENGTH: 623
<212> TYPE: PRT
<213> ORGANISM: Artificial Sequence
<220> FEATURE:
<223> OTHER INFORMATION: PRT720

<400> SEQUENCE: 14

Met His His His His His Ser Ser Gly Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gln Gln Gly Pro Gly Ser Ser Ala
    50                  55                  60

Ala Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
130                 135                 140

Ile Gly Pro Tyr Gly Ser Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala
        180                 185                 190

Gly Ser Gly Gln Gln Val Leu Ile Gly Pro Gly Gln Tyr Val Leu Ile
    195                 200                 205

Gly Pro Tyr Ala Ser Ala Ala Ala Ala Gly Gln Tyr Gly Ser Gly
210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala
        245                 250                 255

Gly Pro Gly Gln Gln Val Leu Ile Gly Pro Tyr Val Leu Ile Gly Pro
    260                 265                 270

Gly Ser Ser Ala Ala Ala Ala Gly Gln Tyr Gly Tyr Gly Pro Gly
275                 280                 285

Gln Gln Gly Pro Tyr Gly Pro Gly Ala Ser Gly Gln Asn Gly Pro Gly
        290                 295                 300

Ser Gly Gln Tyr Gly Pro Gly Gln Gln Gly Pro Gly Gln Ser Ala Ala
305                 310                 315                 320

-continued

Ala Ala Ala Gly Pro Gly Gln Gln Val Leu Ile Gly Pro Tyr Val Leu
            325                 330                 335

Ile Gly Pro Gly Ala Ser Ala Ala Ala Ala Gly Gln Tyr Gly Pro
        340                 345                 350

Gly Gln Gln Gly Pro Gly Gln Tyr Gly Pro Gly Ser Ser Gly Pro Gly
        355                 360                 365

Gln Gln Gly Pro Tyr Gly Pro Gly Ser Ser Ala Ala Ala Ala Gly
        370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Gly Gln Tyr Gln Gln Gly
            405                 410                 415

Pro Gly Gln Gln Gly Pro Tyr Gly Pro Gly Ala Ser Gly Pro Gly Gln
            420                 425                 430

Gln Gly Pro Tyr Gly Pro Gly Ala Ser Ala Ala Ala Ala Gly Pro
        435                 440                 445

Gly Gln Tyr Val Leu Ile Gly Pro Gly Gln Gln Val Leu Ile Gly Pro
        450                 455                 460

Ser Ala Ser Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
            485                 490                 495

Gln Gly Gln Gly Pro Tyr Gly Pro Gly Ala Ser Ala Ala Ala Ala
            500                 505                 510

Gly Ser Tyr Gly Pro Gly Gln Gln Val Leu Ile Gly Pro Tyr Val Leu
        515                 520                 525

Ile Gly Pro Gly Pro Ser Ala Ala Ala Ala Gly Pro Gly Ser Gly
        530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala
            565                 570                 575

Gly Gln Tyr Gln Gln Val Leu Ile Gly Pro Gly Gln Gln Gly Pro Tyr
            580                 585                 590

Val Leu Ile Gly Pro Gly Ala Ser Ala Ala Ala Ala Gly Pro Gly
        595                 600                 605

Ser Gly Gln Gln Val Leu Ile Gly Pro Gly Ala Ser Val Leu Ile
        610                 615                 620

<210> SEQ ID NO 15
<211> LENGTH: 565
<212> TYPE: PRT
<213> ORGANISM: Artificial Sequence
<220> FEATURE:
<223> OTHER INFORMATION: M_PRT525

<400> SEQUENCE: 15

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
                100                 105                 110

Ser Ala Ala Ala Ala Ala Ala Gly Ser Tyr Gly Ser Gly Pro Gly
            115                 120                 125

Gln Gln Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Gly Ser Tyr Gly Ser
    195                 200                 205

Gly Pro Gly Gln Gln Gly Pro Tyr Gly Pro Gly Gln Ser Gly Ser Gly
210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
    275                 280                 285

Gly Gln Tyr Gly Pro Gly Gln Gln Gly Pro Gly Pro Ser Ala Ala Ala
        290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
            325                 330                 335

Gly Pro Gly Gln Tyr Gly Pro Gly Ser Ser Gly Pro Gly Gln Gln Gly
        340                 345                 350

Pro Tyr Gly Pro Gly Ser Ser Ala Ala Ala Ala Ala Ala Gly Ser
    355                 360                 365

Tyr Gly Pro Gly Gln Gln Gly Pro Tyr Gly Pro Gly Pro Ser Ala Ala
370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Gly Pro Gly Gln Tyr
            420                 425                 430

Gly Pro Gly Gln Gln Gly Pro Ser Ala Ser Ala Ala Ala Ala Ala
        435                 440                 445

Ala Gly Ser Tyr Gly Ser Gly Pro Gly Gln Tyr Gly Pro Tyr Gly Pro
            450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Ala Gly Ser Tyr Gly Pro

```
                    485                 490                 495
Gly Gln Gln Gly Pro Tyr Gly Pro Gly Pro Ser Ala Ala Ala Ala
                500                 505                 510
Ala Ala Gly Pro Gly Ser Gly Gln Tyr Gly Pro Gly Ala Ser Gly Gln
            515                 520                 525
Asn Gly Pro Gly Ser Gly Gln Tyr Gly Pro Gly Gln Gln Gly Pro Gly
        530                 535                 540
Pro Ser Ala Ala Ala Ala Ala Ala Gly Pro Gly Ser Gly Gln Gln
545                 550                 555                 560
Gly Pro Gly Ala Ser
                565

<210> SEQ ID NO 16
<211> LENGTH: 565
<212> TYPE: PRT
<213> ORGANISM: Artificial Sequence
<220> FEATURE:
<223> OTHER INFORMATION: M_PRT699

<400> SEQUENCE: 16

Met Gly Pro Gly Val Leu Gly Pro Tyr Gly Pro Gly Ala Ser Ala Ala
1               5                   10                  15
Ala Ala Ala Ala Gly Ser Asn Gly Pro Gly Ser Gly Val Leu Gly
            20                  25                  30
Pro Gly Gln Ser Gly Gln Tyr Gly Pro Gly Val Leu Gly Pro Gly Val
        35                  40                  45
Leu Gly Pro Gly Ser Ser Ala Ala Ala Ala Ala Gly Pro Gly
    50                  55                  60
Gln Tyr Gly Pro Gly Val Leu Gly Pro Ser Ala Ser Ala Ala Ala Ala
65                  70                  75                  80
Ala Ala Ala Gly Pro Gly Ser Gly Val Leu Gly Pro Gly Ala Ser Gly
            85                  90                  95
Gln Tyr Gly Pro Gly Val Leu Gly Pro Gly Val Leu Gly Pro Gly Ser
        100                 105                 110
Ser Ala Ala Ala Ala Ala Ala Gly Ser Tyr Gly Ser Gly Pro Gly
    115                 120                 125
Val Leu Gly Pro Tyr Gly Ser Ala Ala Ala Ala Ala Ala Gly Pro
    130                 135                 140
Gly Ser Gly Gln Tyr Gly Gln Gly Pro Tyr Gly Pro Gly Ala Ser Gly
145                 150                 155                 160
Pro Gly Gln Tyr Gly Pro Gly Val Leu Gly Pro Ser Ala Ser Ala Ala
            165                 170                 175
Ala Ala Ala Ala Gly Ser Gly Val Leu Gly Pro Gly Gln Tyr Gly
        180                 185                 190
Pro Tyr Ala Ser Ala Ala Ala Ala Ala Gly Ser Tyr Gly Ser
    195                 200                 205
Gly Pro Gly Val Leu Gly Pro Tyr Gly Pro Gly Gln Ser Gly Ser Gly
    210                 215                 220
Val Leu Gly Pro Gly Val Leu Gly Pro Tyr Ala Ser Ala Ala Ala
225                 230                 235                 240
Ala Ala Ala Gly Pro Gly Val Leu Gly Pro Tyr Gly Pro Gly Ser Ser
            245                 250                 255
Ala Ala Ala Ala Ala Ala Gly Ser Tyr Gly Tyr Gly Pro Gly Val
        260                 265                 270
Leu Gly Pro Tyr Gly Pro Gly Ala Ser Gly Gln Asn Gly Pro Gly Ser
```

```
                275                 280                 285
Gly Gln Tyr Gly Pro Gly Val Leu Gly Pro Gly Ser Ala Ala Ala
            290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Gly Ser Tyr Gly Pro Gly Val Leu
                325                 330                 335

Gly Pro Gly Gln Tyr Gly Pro Gly Ser Ser Gly Pro Val Leu Gly
            340                 345                 350

Pro Tyr Gly Pro Gly Ser Ser Ala Ala Ala Ala Ala Ala Gly Ser
            355                 360                 365

Tyr Gly Pro Gly Val Leu Gly Pro Tyr Gly Pro Gly Pro Ser Ala Ala
            370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Gly Pro Gly Gln Tyr
            420                 425                 430

Gly Pro Gly Val Leu Gly Pro Ser Ala Ser Ala Ala Ala Ala Ala
            435                 440                 445

Ala Gly Ser Tyr Gly Ser Gly Pro Gly Gln Tyr Gly Pro Tyr Gly Pro
            450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Ala Gly Ser Tyr Gly Pro
            485                 490                 495

Gly Val Leu Gly Pro Tyr Gly Pro Gly Pro Ser Ala Ala Ala Ala
            500                 505                 510

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Val Leu Gly Pro Gly
            530                 535                 540

Pro Ser Ala Ala Ala Ala Ala Ala Gly Pro Gly Ser Gly Val Leu
545                 550                 555                 560

Gly Pro Gly Ala Ser
                565

<210> SEQ ID NO 17
<211> LENGTH: 565
<212> TYPE: PRT
<213> ORGANISM: Artificial Sequence
<220> FEATURE:
<223> OTHER INFORMATION: M_PRT698

<400> SEQUENCE: 17

Met Gly Pro Gly Val Leu Gly Pro Tyr Gly Pro Gly Ala Ser Ala Ala
1               5                   10                  15

Ala Ala Ala Ala Gly Ser Asn Gly Pro Gly Ser Gly Val Leu Gly
            20                  25                  30

Pro Gly Ile Ser Gly Ile Tyr Gly Pro Gly Val Leu Pro Gly Val
            35                  40                  45

Leu Gly Pro Gly Ser Ser Ala Ala Ala Ala Ala Ala Gly Pro Gly
            50                  55                  60

Ile Tyr Gly Pro Gly Val Leu Gly Pro Ser Ala Ser Ala Ala Ala Ala
```

-continued

```
         65                  70                  75                  80
Ala Ala Ala Gly Pro Gly Ser Gly Val Leu Gly Pro Gly Ala Ser Gly
                 85                  90                  95
Ile Tyr Gly Pro Gly Val Leu Gly Pro Gly Val Leu Gly Pro Gly Ser
                100                 105                 110
Ser Ala Ala Ala Ala Ala Ala Gly Ser Tyr Gly Ser Gly Pro Gly
                115                 120                 125
Val Leu Gly Pro Tyr Gly Ser Ala Ala Ala Ala Ala Ala Gly Pro
    130                 135                 140
Gly Ser Gly Ile Tyr Gly Ile Gly Pro Tyr Gly Pro Gly Ala Ser Gly
145                 150                 155                 160
Pro Gly Ile Tyr Gly Pro Gly Val Leu Gly Pro Ser Ala Ser Ala Ala
                165                 170                 175
Ala Ala Ala Ala Ala Gly Ser Gly Val Leu Gly Pro Gly Ile Tyr Gly
                180                 185                 190
Pro Tyr Ala Ser Ala Ala Ala Ala Ala Gly Ser Tyr Gly Ser
    195                 200                 205
Gly Pro Gly Val Leu Gly Pro Tyr Gly Pro Gly Ile Ser Gly Ser Gly
    210                 215                 220
Val Leu Gly Pro Gly Val Leu Gly Pro Tyr Ala Ser Ala Ala Ala Ala
225                 230                 235                 240
Ala Ala Ala Gly Pro Gly Val Leu Gly Pro Tyr Gly Pro Gly Ser Ser
                245                 250                 255
Ala Ala Ala Ala Ala Ala Gly Ser Tyr Gly Tyr Gly Pro Gly Val
                260                 265                 270
Leu Gly Pro Tyr Gly Pro Gly Ala Ser Gly Ile Asn Gly Pro Gly Ser
    275                 280                 285
Gly Ile Tyr Gly Pro Gly Val Leu Gly Pro Gly Pro Ser Ala Ala Ala
    290                 295                 300
Ala Ala Ala Ala Gly Pro Gly Val Leu Gly Pro Tyr Gly Pro Gly Ala
305                 310                 315                 320
Ser Ala Ala Ala Ala Ala Ala Gly Ser Tyr Gly Pro Gly Val Leu
                325                 330                 335
Gly Pro Gly Ile Tyr Gly Pro Gly Ser Ser Gly Pro Gly Val Leu Gly
    340                 345                 350
Pro Tyr Gly Pro Gly Ser Ser Ala Ala Ala Ala Ala Ala Gly Ser
    355                 360                 365
Tyr Gly Pro Gly Val Leu Gly Pro Tyr Gly Pro Gly Pro Ser Ala Ala
    370                 375                 380
Ala Ala Ala Ala Ala Gly Ser Tyr Val Leu Gly Pro Gly Val Leu Gly
385                 390                 395                 400
Pro Tyr Gly Pro Gly Ala Ser Gly Pro Gly Val Leu Gly Pro Tyr Gly
                405                 410                 415
Pro Gly Ala Ser Ala Ala Ala Ala Ala Gly Pro Gly Ile Tyr
            420                 425                 430
Gly Pro Gly Val Leu Gly Pro Ser Ala Ser Ala Ala Ala Ala Ala
            435                 440                 445
Ala Gly Ser Tyr Gly Ser Gly Pro Gly Ile Tyr Gly Pro Tyr Gly Pro
    450                 455                 460
Gly Ile Ser Gly Pro Gly Ser Gly Val Leu Gly Ile Gly Pro Tyr Gly
465                 470                 475                 480
Pro Gly Ala Ser Ala Ala Ala Ala Ala Ala Gly Ser Tyr Gly Pro
            485                 490                 495
```

-continued

Gly Val Leu Gly Pro Tyr Pro Gly Pro Ser Ala Ala Ala Ala
            500                 505                 510

Ala Ala Gly Pro Gly Ser Gly Ile Tyr Gly Pro Gly Ala Ser Gly Ile
        515                 520                 525

Asn Gly Pro Gly Ser Gly Ile Tyr Gly Pro Gly Val Leu Gly Pro Gly
        530                 535                 540

Pro Ser Ala Ala Ala Ala Ala Ala Gly Pro Gly Ser Gly Val Leu
545                 550                 555                 560

Gly Pro Gly Ala Ser
            565

<210> SEQ ID NO 18
<211> LENGTH: 576
<212> TYPE: PRT
<213> ORGANISM: Artificial Sequence
<220> FEATURE:
<223> OTHER INFORMATION: PRT525

<400> SEQUENCE: 18

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Pro Gly Gln Ser Gly
            35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
            85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala
            115                 120                 125

Ala Ala Ala Gly Ser Tyr Gly Ser Gly Pro Gly Gln Gln Gly Pro Tyr
            130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
            165                 170                 175

Pro Gly Gln Gln Gly Pro Ser Ala Ser Ala Ala Ala Ala Ala Ala
            180                 185                 190

Gly Ser Gly Gln Gln Gly Pro Gly Gln Tyr Gly Pro Tyr Ala Ser Ala
            195                 200                 205

Ala Ala Ala Ala Ala Gly Ser Tyr Gly Ser Gly Pro Gly Gln Gln
            210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
            245                 250                 255

Gly Gln Gln Gly Pro Tyr Gly Pro Gly Ser Ser Ala Ala Ala Ala
            260                 265                 270

Ala Ala Gly Ser Tyr Gly Tyr Gly Pro Gly Gln Gln Gly Pro Tyr Gly
            275                 280                 285

-continued

```
Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Ala Ala Gly
305                 310                 315                 320

Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
        355                 360                 365

Ser Ser Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
                420                 425                 430

Ala Ala Ala Ala Ala Gly Pro Gly Gln Tyr Gly Pro Gly Gln Gln
    435                 440                 445

Gly Pro Ser Ala Ser Ala Ala Ala Ala Ala Gly Ser Tyr Gly
450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
                485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
                515                 520                 525

Ser Gly Gln Tyr Gly Pro Gly Ala Ser Gly Gln Asn Gly Pro Gly Ser
    530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575
```

<210> SEQ ID NO 19
<211> LENGTH: 576
<212> TYPE: PRT
<213> ORGANISM: Artificial Sequence
<220> FEATURE:
<223> OTHER INFORMATION: PRT699

<400> SEQUENCE: 19

```
Met His His His His His Ser Ser Gly Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Pro Gly Gln Ser Gly
            35                  40                  45

Gln Tyr Gly Pro Gly Val Leu Gly Pro Gly Val Leu Gly Pro Gly Ser
    50                  55                  60

Ser Ala Ala Ala Ala Ala Ala Gly Pro Gly Gln Tyr Gly Pro Gly
65                  70                  75                  80
```

```
Val Leu Gly Pro Ser Ala Ser Ala Ala Ala Ala Ala Gly Pro
                85                  90                  95

Gly Ser Gly Val Leu Gly Pro Gly Ala Ser Gly Gln Tyr Gly Pro Gly
               100                 105                 110

Val Leu Gly Pro Gly Val Leu Gly Pro Gly Ser Ser Ala Ala Ala
            115                 120                 125

Ala Ala Ala Gly Ser Tyr Gly Ser Gly Pro Gly Val Leu Gly Pro Tyr
        130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala
            180                 185                 190

Gly Ser Gly Val Leu Gly Pro Gly Gln Tyr Gly Pro Tyr Ala Ser Ala
            195                 200                 205

Ala Ala Ala Ala Ala Ala Gly Ser Tyr Gly Ser Gly Pro Gly Val Leu
        210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Gly Pro
            245                 250                 255

Gly Val Leu Gly Pro Tyr Gly Pro Gly Ser Ser Ala Ala Ala Ala Ala
            260                 265                 270

Ala Ala Gly Ser Tyr Gly Tyr Gly Pro Gly Val Leu Gly Pro Tyr Gly
        275                 280                 285

Pro Gly Ala Ser Gly Gln Asn Gly Pro Gly Ser Gly Gln Tyr Gly Pro
            290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
            325                 330                 335

Ala Ala Ala Gly Ser Tyr Gly Pro Gly Val Leu Gly Pro Gly Gln Tyr
        340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Gly Ser Tyr Gly Pro Gly Val
370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
            405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
        435                 440                 445

Gly Pro Ser Ala Ser Ala Ala Ala Ala Ala Ala Gly Ser Tyr Gly
            450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
                485                 490                 495
```

```
Ala Ala Ala Ala Ala Gly Ser Tyr Gly Pro Gly Val Leu Gly Pro
            500             505             510

Tyr Gly Pro Gly Pro Ser Ala Ala Ala Ala Ala Ala Gly Pro Gly
        515             520             525

Ser Gly Gln Tyr Gly Pro Gly Ala Ser Gly Gln Asn Gly Pro Gly Ser
    530             535             540

Gly Gln Tyr Gly Pro Gly Val Leu Gly Pro Gly Pro Ser Ala Ala Ala
545             550             555             560

Ala Ala Ala Ala Gly Pro Gly Ser Gly Val Leu Gly Pro Gly Ala Ser
            565             570             575
```

<210> SEQ ID NO 20
<211> LENGTH: 576
<212> TYPE: PRT
<213> ORGANISM: Artificial Sequence
<220> FEATURE:
<223> OTHER INFORMATION: PRT698

<400> SEQUENCE: 20

```
Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
            20                  25                  30

Gly Ser Asn Gly Pro Gly Ser Gly Val Leu Gly Pro Gly Ile Ser Gly
        35                  40                  45

Ile Tyr Gly Pro Gly Val Leu Gly Pro Gly Val Leu Gly Pro Gly Ser
    50                  55                  60

Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Ala Gly Pro
            85                  90                  95

Gly Ser Gly Val Leu Gly Pro Gly Ala Ser Gly Ile Tyr Gly Pro Gly
        100                 105                 110

Val Leu Gly Pro Gly Val Leu Gly Pro Gly Ser Ser Ala Ala Ala Ala
    115                 120                 125

Ala Ala Ala Gly Ser Tyr Gly Ser Gly Pro Gly Val Leu Gly Pro Tyr
130                 135                 140

Gly Ser Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
            165                 170                 175

Pro Gly Val Leu Gly Pro Ser Ala Ser Ala Ala Ala Ala Ala Ala
        180                 185                 190

Gly Ser Gly Val Leu Gly Pro Gly Ile Tyr Gly Pro Tyr Ala Ser Ala
    195                 200                 205

Ala Ala Ala Ala Ala Gly Ser Tyr Gly Ser Gly Pro Gly Val Leu
210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Gly Pro
            245                 250                 255

Gly Val Leu Gly Pro Tyr Gly Pro Gly Ser Ser Ala Ala Ala Ala Ala
        260                 265                 270

Ala Ala Gly Ser Tyr Gly Tyr Gly Pro Gly Val Leu Gly Pro Tyr Gly
    275                 280                 285
```

-continued

```
Pro Gly Ala Ser Gly Ile Asn Gly Pro Gly Ser Gly Ile Tyr Gly Pro
    290                 295                 300

Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Ile Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Gly Pro Gly Ile Tyr Gly Pro Gly Val Leu
    435                 440                 445

Gly Pro Ser Ala Ser Ala Ala Ala Ala Ala Gly Ser Tyr Gly
    450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
                485                 490                 495

Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Gly Pro Gly
        515                 520                 525

Ser Gly Ile Tyr Gly Pro Gly Ala Ser Gly Ile Asn Gly Pro Gly Ser
    530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575
```

<210> SEQ ID NO 21
<211> LENGTH: 590
<212> TYPE: PRT
<213> ORGANISM: Artificial Sequence
<220> FEATURE:
<223> OTHER INFORMATION: M_PRT917

<400> SEQUENCE: 21

```
Met Gly Pro Gly Leu Ile Gly Pro Tyr Gly Pro Gly Ala Ser Ala Ala
1               5                   10                  15

Ala Ala Ala Gly Val Asn Gly Pro Gly Ser Gly Leu Ile Gly Pro Gly
                20                  25                  30

Val Ser Gly Val Tyr Gly Pro Gly Leu Ile Gly Pro Gly Leu Ile Gly
            35                  40                  45

Pro Gly Ser Ser Ala Ala Ala Ala Gly Pro Gly Val Tyr Gly Pro
        50                  55                  60

Gly Leu Ile Gly Pro Ser Ala Ser Ala Ala Ala Ala Gly Pro Gly
65                  70                  75                  80
```

```
Ser Gly Leu Ile Gly Pro Gly Ala Ser Gly Val Tyr Gly Pro Gly Leu
                85                  90                  95

Ile Gly Pro Gly Leu Ile Gly Pro Gly Ser Ala Ala Ala Ala
            100                 105                 110

Gly Val Tyr Gly Ser Gly Pro Gly Leu Ile Gly Pro Tyr Gly Ser Ala
            115                 120                 125

Ala Ala Ala Ala Gly Pro Gly Ser Gly Val Tyr Gly Val Gly Pro Tyr
130                 135                 140

Gly Pro Gly Ala Ser Gly Pro Gly Val Tyr Gly Pro Gly Leu Ile Gly
145                 150                 155                 160

Pro Ser Ala Ser Ala Ala Ala Ala Gly Ser Gly Leu Ile Gly Pro
                165                 170                 175

Gly Val Tyr Gly Pro Tyr Ala Ser Ala Ala Ala Ala Gly Val Tyr
            180                 185                 190

Gly Ser Gly Pro Gly Leu Ile Gly Pro Tyr Gly Pro Gly Val Ser Gly
            195                 200                 205

Ser Gly Leu Ile Gly Pro Gly Leu Ile Gly Pro Tyr Ala Ser Ala Ala
            210                 215                 220

Ala Ala Ala Gly Pro Gly Leu Ile Gly Pro Tyr Gly Pro Gly Ser Ser
225                 230                 235                 240

Ala Ala Ala Ala Gly Val Tyr Gly Tyr Gly Pro Gly Leu Ile Gly
            245                 250                 255

Pro Tyr Gly Pro Gly Ala Ser Gly Val Asn Gly Pro Gly Ser Gly Val
            260                 265                 270

Tyr Gly Pro Gly Leu Ile Gly Pro Gly Val Ser Ala Ala Ala Ala
            275                 280                 285

Gly Pro Gly Leu Ile Gly Pro Tyr Gly Pro Gly Ala Ser Ala Ala Ala
            290                 295                 300

Ala Ala Gly Val Tyr Gly Pro Gly Leu Ile Gly Pro Gly Val Tyr Gly
305                 310                 315                 320

Pro Gly Ser Ser Gly Pro Gly Leu Ile Gly Pro Tyr Gly Pro Gly Ser
                325                 330                 335

Ser Ala Ala Ala Ala Gly Val Tyr Gly Pro Gly Leu Ile Gly Pro
            340                 345                 350

Tyr Gly Pro Gly Val Ser Ala Ala Ala Ala Gly Val Tyr Leu Ile
            355                 360                 365

Gly Pro Gly Leu Ile Gly Pro Tyr Gly Pro Gly Ala Ser Gly Pro Gly
            370                 375                 380

Leu Ile Gly Pro Tyr Gly Pro Gly Ala Ser Ala Ala Ala Ala Gly
385                 390                 395                 400

Pro Gly Val Tyr Gly Pro Gly Leu Ile Gly Pro Ser Ala Ser Ala Ala
                405                 410                 415

Ala Ala Ala Gly Val Tyr Gly Ser Gly Pro Gly Val Tyr Gly Pro Tyr
            420                 425                 430

Gly Pro Gly Val Ser Gly Pro Gly Ser Gly Leu Ile Gly Val Gly Pro
            435                 440                 445

Tyr Gly Pro Gly Ala Ser Ala Ala Ala Ala Gly Val Tyr Gly Pro
            450                 455                 460

Gly Leu Ile Gly Pro Tyr Gly Pro Gly Val Ser Ala Ala Ala Ala
465                 470                 475                 480

Gly Pro Gly Ser Gly Val Tyr Gly Pro Gly Ala Ser Gly Val Asn Gly
                485                 490                 495

Pro Gly Ser Gly Val Tyr Gly Pro Gly Leu Ile Gly Pro Gly Val Ser
```

```
                500              505              510
Ala Ala Ala Ala Gly Val Tyr Leu Ile Gly Pro Gly Leu Ile Gly
            515              520              525

Pro Tyr Gly Pro Gly Ala Ser Ala Ala Ala Ala Gly Val Tyr Gly
        530              535              540

Ser Gly Pro Gly Leu Ile Gly Pro Tyr Gly Pro Val Ser Gly Ser
545              550              555              560

Gly Leu Ile Gly Pro Gly Leu Ile Gly Pro Tyr Ala Ser Ala Ala
                565              570              575

Ala Ala Gly Pro Gly Ser Gly Leu Ile Gly Pro Gly Ala Ser
            580              585              590

<210> SEQ ID NO 22
<211> LENGTH: 587
<212> TYPE: PRT
<213> ORGANISM: Artificial Sequence
<220> FEATURE:
<223> OTHER INFORMATION: M_PRT1028

<400> SEQUENCE: 22

Met Gly Pro Gly Ile Phe Gly Pro Tyr Gly Pro Gly Ala Ser Ala Ala
1               5                   10                  15

Ala Ala Ala Gly Thr Gly Pro Gly Ser Gly Ile Phe Gly Pro Gly Thr
            20                  25                  30

Ser Gly Thr Tyr Gly Pro Gly Ile Phe Gly Pro Gly Ile Phe Gly Pro
        35                  40                  45

Gly Ser Ser Ala Ala Ala Ala Gly Pro Gly Thr Tyr Gly Pro Gly
50                  55                  60

Ile Phe Gly Pro Ser Ala Ser Ala Ala Ala Ala Gly Pro Gly Ser
65                  70                  75                  80

Gly Ile Phe Gly Pro Gly Ala Ser Gly Thr Tyr Gly Pro Gly Ile Phe
                85                  90                  95

Gly Pro Gly Ile Phe Gly Pro Gly Ser Ser Ala Ala Ala Ala Gly
            100                 105                 110

Thr Tyr Gly Ser Gly Pro Gly Ile Phe Gly Pro Tyr Gly Ser Ala Ala
            115                 120                 125

Ala Ala Ala Gly Pro Gly Ser Gly Thr Tyr Gly Thr Gly Pro Tyr Gly
        130                 135                 140

Pro Gly Ala Ser Gly Pro Gly Thr Tyr Gly Pro Gly Ile Phe Gly Pro
145                 150                 155                 160

Ser Ala Ser Ala Ala Ala Ala Gly Ser Gly Ile Phe Gly Pro Gly
                165                 170                 175

Thr Tyr Gly Pro Tyr Ala Ser Ala Ala Ala Ala Gly Thr Tyr Gly
            180                 185                 190

Ser Gly Pro Gly Ile Phe Gly Pro Tyr Gly Pro Gly Thr Ser Gly Ser
        195                 200                 205

Gly Ile Phe Gly Pro Gly Ile Phe Gly Pro Tyr Ala Ser Ala Ala Ala
    210                 215                 220

Ala Ala Gly Pro Gly Ile Phe Gly Pro Tyr Gly Pro Gly Ser Ser Ala
225                 230                 235                 240

Ala Ala Ala Gly Thr Tyr Gly Tyr Gly Pro Gly Ile Phe Gly Pro
                245                 250                 255

Tyr Gly Pro Gly Ala Ser Gly Thr Gly Pro Gly Ser Gly Thr Tyr Gly
            260                 265                 270

Pro Gly Ile Phe Gly Pro Gly Thr Ser Ala Ala Ala Ala Gly Pro
```

```
                275                 280                 285
Gly Ile Phe Gly Pro Tyr Gly Pro Gly Ala Ser Ala Ala Ala Ala
            290                 295                 300
Gly Thr Tyr Gly Pro Gly Ile Phe Pro Gly Thr Tyr Gly Pro Gly
305                 310                 315                 320
Ser Ser Gly Pro Gly Ile Phe Gly Pro Tyr Gly Pro Gly Ser Ala
                325                 330                 335
Ala Ala Ala Gly Thr Tyr Gly Pro Gly Ile Phe Gly Pro Tyr Gly
            340                 345                 350
Pro Gly Thr Ser Ala Ala Ala Ala Gly Thr Tyr Ile Phe Gly Pro
            355                 360                 365
Gly Ile Phe Gly Pro Tyr Gly Pro Gly Ala Ser Gly Pro Gly Ile Phe
            370                 375                 380
Gly Pro Tyr Gly Pro Gly Ala Ser Ala Ala Ala Ala Gly Pro Gly
385                 390                 395                 400
Thr Tyr Gly Pro Gly Ile Phe Gly Pro Ser Ala Ser Ala Ala Ala
                405                 410                 415
Ala Gly Thr Tyr Gly Ser Gly Pro Gly Thr Tyr Gly Pro Tyr Gly Pro
            420                 425                 430
Gly Thr Ser Gly Pro Gly Ser Gly Ile Phe Gly Thr Gly Pro Tyr Gly
            435                 440                 445
Pro Gly Ala Ser Ala Ala Ala Ala Gly Thr Tyr Gly Pro Gly Ile
            450                 455                 460
Phe Gly Pro Tyr Gly Pro Gly Thr Ser Ala Ala Ala Ala Gly Pro
465                 470                 475                 480
Gly Ser Gly Thr Tyr Gly Pro Gly Ala Ser Gly Thr Gly Pro Gly Ser
                485                 490                 495
Gly Thr Tyr Gly Pro Gly Ile Phe Gly Pro Gly Thr Ser Ala Ala Ala
            500                 505                 510
Ala Ala Gly Thr Tyr Ile Phe Gly Pro Gly Ile Phe Gly Pro Tyr Gly
            515                 520                 525
Pro Gly Ala Ser Ala Ala Ala Ala Gly Thr Tyr Gly Ser Gly Pro
530                 535                 540
Gly Ile Phe Gly Pro Tyr Gly Pro Gly Thr Ser Gly Ser Gly Ile Phe
545                 550                 555                 560
Gly Pro Gly Ile Phe Gly Pro Tyr Ala Ser Ala Ala Ala Ala Gly
                565                 570                 575
Pro Gly Ser Gly Ile Phe Gly Pro Gly Ala Ser
            580                 585

<210> SEQ ID NO 23
<211> LENGTH: 601
<212> TYPE: PRT
<213> ORGANISM: Artificial Sequence
<220> FEATURE:
<223> OTHER INFORMATION: PRT917

<400> SEQUENCE: 23

Met His His His His His Ser Ser Gly Ser Gly Pro Gly Leu
1               5                   10                  15

Ile Gly Pro Tyr Gly Pro Gly Ala Ser Ala Ala Ala Ala Gly Val
                20                  25                  30

Asn Gly Pro Gly Ser Gly Leu Ile Gly Pro Gly Val Ser Gly Val Tyr
            35                  40                  45

Gly Pro Gly Leu Ile Gly Pro Gly Leu Ile Gly Pro Gly Ser Ser Ala
```

```
                50                  55                  60
Ala Ala Ala Ala Gly Pro Gly Val Tyr Gly Pro Gly Leu Ile Gly Pro
 65                  70                  75                  80

Ser Ala Ser Ala Ala Ala Ala Gly Pro Gly Ser Gly Leu Ile Gly
                 85                  90                  95

Pro Gly Ala Ser Gly Val Tyr Gly Pro Gly Leu Ile Gly Pro Gly Leu
                100                 105                 110

Ile Gly Pro Gly Ser Ser Ala Ala Ala Ala Gly Val Tyr Gly Ser
                115                 120                 125

Gly Pro Gly Leu Ile Gly Pro Tyr Gly Ser Ala Ala Ala Ala Gly
                130                 135                 140

Pro Gly Ser Gly Val Tyr Gly Val Gly Pro Tyr Gly Pro Gly Ala Ser
145                 150                 155                 160

Gly Pro Gly Val Tyr Gly Pro Gly Leu Ile Gly Pro Ser Ala Ser Ala
                165                 170                 175

Ala Ala Ala Ala Gly Ser Gly Leu Ile Gly Pro Gly Val Tyr Gly Pro
                180                 185                 190

Tyr Ala Ser Ala Ala Ala Ala Gly Val Tyr Gly Ser Gly Pro Gly
                195                 200                 205

Leu Ile Gly Pro Tyr Gly Pro Gly Val Ser Gly Ser Gly Leu Ile Gly
                210                 215                 220

Pro Gly Leu Ile Gly Pro Tyr Ala Ser Ala Ala Ala Ala Gly Pro
225                 230                 235                 240

Gly Leu Ile Gly Pro Tyr Gly Pro Gly Ser Ser Ala Ala Ala Ala
                245                 250                 255

Gly Val Tyr Gly Tyr Gly Pro Gly Leu Ile Gly Pro Tyr Gly Pro Gly
                260                 265                 270

Ala Ser Gly Val Asn Gly Pro Gly Ser Gly Val Tyr Gly Pro Gly Leu
                275                 280                 285

Ile Gly Pro Gly Val Ser Ala Ala Ala Ala Gly Pro Gly Leu Ile
                290                 295                 300

Gly Pro Tyr Gly Pro Gly Ala Ser Ala Ala Ala Ala Gly Val Tyr
305                 310                 315                 320

Gly Pro Gly Leu Ile Gly Pro Gly Val Tyr Gly Pro Gly Ser Ser Gly
                325                 330                 335

Pro Gly Leu Ile Gly Pro Tyr Gly Pro Gly Ser Ser Ala Ala Ala
                340                 345                 350

Ala Gly Val Tyr Gly Pro Gly Leu Ile Gly Pro Tyr Gly Pro Gly Val
                355                 360                 365

Ser Ala Ala Ala Ala Gly Val Tyr Leu Ile Gly Pro Gly Leu Ile
370                 375                 380

Gly Pro Tyr Gly Pro Gly Ala Ser Gly Pro Gly Leu Ile Gly Pro Tyr
385                 390                 395                 400

Gly Pro Gly Ala Ser Ala Ala Ala Ala Gly Pro Gly Val Tyr Gly
                405                 410                 415

Pro Gly Leu Ile Gly Pro Ser Ala Ser Ala Ala Ala Ala Gly Val
                420                 425                 430

Tyr Gly Ser Gly Pro Gly Val Tyr Gly Pro Gly Pro Gly Val Ser
                435                 440                 445

Gly Pro Gly Ser Gly Leu Ile Gly Val Gly Pro Tyr Gly Pro Gly Ala
                450                 455                 460

Ser Ala Ala Ala Ala Ala Gly Val Tyr Gly Pro Gly Leu Ile Gly Pro
465                 470                 475                 480
```

```
Tyr Gly Pro Gly Val Ser Ala Ala Ala Ala Gly Pro Gly Ser Gly
                485                 490                 495

Val Tyr Gly Pro Gly Ala Ser Gly Val Asn Gly Pro Gly Ser Gly Val
            500                 505                 510

Tyr Gly Pro Gly Leu Ile Gly Pro Gly Val Ser Ala Ala Ala Ala
            515                 520                 525

Gly Val Tyr Leu Ile Gly Pro Gly Leu Ile Gly Pro Tyr Gly Pro Gly
        530                 535                 540

Ala Ser Ala Ala Ala Ala Gly Val Tyr Gly Ser Gly Pro Gly Leu
545                 550                 555                 560

Ile Gly Pro Tyr Gly Pro Gly Val Ser Gly Ser Gly Leu Ile Gly Pro
            565                 570                 575

Gly Leu Ile Gly Pro Tyr Ala Ser Ala Ala Ala Ala Gly Pro Gly
            580                 585                 590

Ser Gly Leu Ile Gly Pro Gly Ala Ser
            595                 600

<210> SEQ ID NO 24
<211> LENGTH: 598
<212> TYPE: PRT
<213> ORGANISM: Artificial Sequence
<220> FEATURE:
<223> OTHER INFORMATION: PRT1028

<400> SEQUENCE: 24

Met His His His His His Ser Ser Gly Ser Ser Gly Pro Gly Ile
1               5                   10                  15

Phe Gly Pro Tyr Gly Pro Gly Ala Ser Ala Ala Ala Ala Gly Thr
                20                  25                  30

Gly Pro Gly Ser Gly Ile Phe Gly Pro Gly Thr Ser Gly Thr Tyr Gly
            35                  40                  45

Pro Gly Ile Phe Gly Pro Gly Ile Phe Gly Pro Gly Ser Ser Ala Ala
        50                  55                  60

Ala Ala Ala Gly Pro Gly Thr Tyr Gly Pro Gly Ile Phe Gly Pro Ser
65                  70                  75                  80

Ala Ser Ala Ala Ala Ala Gly Pro Gly Ser Gly Ile Phe Gly Pro
                85                  90                  95

Gly Ala Ser Gly Thr Tyr Gly Pro Gly Ile Phe Gly Pro Gly Ile Phe
            100                 105                 110

Gly Pro Gly Ser Ser Ala Ala Ala Ala Gly Thr Tyr Gly Ser Gly
            115                 120                 125

Pro Gly Ile Phe Gly Pro Tyr Gly Ser Ala Ala Ala Ala Gly Pro
        130                 135                 140

Gly Ser Gly Thr Tyr Gly Thr Gly Pro Tyr Pro Gly Ala Ser Gly
145                 150                 155                 160

Pro Gly Thr Tyr Gly Pro Gly Ile Phe Gly Pro Ser Ala Ser Ala Ala
                165                 170                 175

Ala Ala Ala Gly Ser Gly Ile Phe Gly Pro Gly Thr Tyr Gly Pro Tyr
            180                 185                 190

Ala Ser Ala Ala Ala Ala Gly Thr Tyr Gly Ser Gly Pro Gly Ile
            195                 200                 205

Phe Gly Pro Tyr Gly Pro Gly Thr Ser Gly Ser Gly Ile Phe Gly Pro
        210                 215                 220

Gly Ile Phe Gly Pro Tyr Ala Ser Ala Ala Ala Ala Gly Pro Gly
225                 230                 235                 240
```

-continued

```
Ile Phe Gly Pro Tyr Gly Pro Gly Ser Ser Ala Ala Ala Ala Gly
                245                 250                 255

Thr Tyr Gly Tyr Gly Pro Gly Ile Phe Gly Pro Tyr Gly Pro Gly Ala
            260                 265                 270

Ser Gly Thr Gly Pro Gly Ser Gly Thr Tyr Gly Pro Gly Ile Phe Gly
            275                 280                 285

Pro Gly Thr Ser Ala Ala Ala Ala Gly Pro Gly Ile Phe Gly Pro
        290                 295                 300

Tyr Gly Pro Gly Ala Ser Ala Ala Ala Ala Gly Thr Tyr Gly Pro
305                 310                 315                 320

Gly Ile Phe Gly Pro Gly Thr Tyr Gly Pro Gly Ser Ser Gly Pro Gly
                325                 330                 335

Ile Phe Gly Pro Tyr Gly Pro Gly Ser Ser Ala Ala Ala Ala Gly
            340                 345                 350

Thr Tyr Gly Pro Gly Ile Phe Gly Pro Tyr Gly Pro Gly Thr Ser Ala
            355                 360                 365

Ala Ala Ala Ala Gly Thr Tyr Ile Phe Gly Pro Gly Ile Phe Gly Pro
        370                 375                 380

Tyr Gly Pro Gly Ala Ser Gly Pro Gly Ile Phe Gly Pro Tyr Gly Pro
385                 390                 395                 400

Gly Ala Ser Ala Ala Ala Ala Gly Pro Gly Thr Tyr Gly Pro Gly
            405                 410                 415

Ile Phe Gly Pro Ser Ala Ser Ala Ala Ala Ala Gly Thr Tyr Gly
            420                 425                 430

Ser Gly Pro Gly Thr Tyr Gly Pro Tyr Gly Pro Gly Thr Ser Gly Pro
        435                 440                 445

Gly Ser Gly Ile Phe Gly Thr Gly Pro Tyr Gly Pro Gly Ala Ser Ala
    450                 455                 460

Ala Ala Ala Gly Thr Tyr Gly Pro Gly Ile Phe Gly Pro Tyr Gly
465                 470                 475                 480

Pro Gly Thr Ser Ala Ala Ala Ala Gly Pro Gly Ser Gly Thr Tyr
            485                 490                 495

Gly Pro Gly Ala Ser Gly Thr Gly Pro Gly Ser Gly Tyr Gly Pro
            500                 505                 510

Gly Ile Phe Gly Pro Gly Thr Ser Ala Ala Ala Ala Gly Thr Tyr
    515                 520                 525

Ile Phe Gly Pro Gly Ile Phe Gly Pro Tyr Gly Pro Gly Ala Ser
    530                 535                 540

Ala Ala Ala Ala Gly Thr Tyr Gly Ser Gly Pro Gly Ile Phe Gly Pro
545                 550                 555                 560

Tyr Gly Pro Gly Thr Ser Gly Ser Gly Ile Phe Gly Pro Gly Ile Phe
            565                 570                 575

Gly Pro Tyr Ala Ser Ala Ala Ala Ala Gly Pro Gly Ser Gly Ile
        580                 585                 590

Phe Gly Pro Gly Ala Ser
        595
```

<210> SEQ ID NO 25
<211> LENGTH: 50
<212> TYPE: PRT
<213> ORGANISM: Araneus diadematus

<400> SEQUENCE: 25

Ser Gly Cys Asp Val Leu Val Gln Ala Leu Leu Glu Val Val Ser Ala

```
                1               5                   10                  15
Leu Val Ser Ile Leu Gly Ser Ser Ser Ile Gly Gln Ile Asn Tyr Gly
                20                  25                  30

Ala Ser Ala Gln Tyr Thr Gln Met Val Gly Gln Ser Val Ala Gln Ala
        35                  40                  45

Leu Ala
    50

<210> SEQ ID NO 26
<211> LENGTH: 30
<212> TYPE: PRT
<213> ORGANISM: Araneus diadematus

<400> SEQUENCE: 26

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 27
<211> LENGTH: 21
<212> TYPE: PRT
<213> ORGANISM: Araneus diadematus

<400> SEQUENCE: 27

Ser Gly Cys Asp Val Leu Val Gln Ala Leu Leu Glu Val Val Ser Ala
1               5                   10                  15

Leu Val Ser Ile Leu
            20

<210> SEQ ID NO 28
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 28

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160
```

```
Gly Gly Tyr Gly Pro Gly Ser Gly Gln Gln Gly Pro Gly Gln Gln Gly
            165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gly Pro Gly Gln Gln
            195                 200                 205
Gly Pro Gly Gly Gln Pro Tyr Gly Pro Gly Ala Ser Ala Ala Ala
210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gln Gly Pro Tyr Gly
            245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gly Pro
            275                 280                 285
Tyr Gly Pro Gly Ala Ser Ala Ala Ser Ala Ala Ser Gly Gly Tyr Gly
            290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
            325                 330                 335
Tyr Gly Pro Gly Ser Gly Gln Gln Gly Pro Gly Gln Gln Gly Pro Gly
            340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
            435                 440                 445
Gly Tyr Gly Pro Gly Ser Gly Gln Gln Gly Pro Gly Gln Gln Gly Pro
            450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
            485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
            515                 520                 525
Gly Gly Gln Gly Pro Tyr Gly Pro Gly Ala Ala Ser Ala Ala Val Ser
            530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
            565                 570                 575
```

```
Ala Ser Ala Ala Ala Ala Ala Gly Gly Tyr Gly Pro Gly Ser Gly
            580                 585                 590
Gln Gln Gly Pro Ser Gln Gly Pro Gly Gln Gln Gly Pro Gly Gly
            595                 600                 605
Gln Gly Pro Tyr Gly Pro Gly Ala Ser Ala Ala Ala Ala Ala Gly
            610                 615                 620
Gly Tyr Gly Pro Gly Ser Gly Gln Gln Gly Pro Gly Gln Gly Pro
625                 630                 635                 640
Tyr Gly Pro Gly Ser Ser Ala Ala Ala Ala Ala Gly Gly Asn Gly
                645                 650                 655
Pro Gly Ser Gly Gln Gln Gly Ala Gly Gln Gln Gly Pro Gly Gln
            660                 665                 670
Gly Pro Gly Ala Ser Ala Ala Ala Ala Ala Gly Gly Tyr Gly Pro
            675                 680                 685
Gly Ser Gly Gln Gln Gly Pro Gly Gln Gln Gly Pro Gly Gln Gly
            690                 695                 700
Pro Tyr Gly Pro Gly Ala Ser Ala Ala Ala Ala Ala Gly Gly Tyr
705                 710                 715                 720
Gly Pro Gly Ser Gly Gln Gly Pro Gly Gln Gln Gly Pro Gly Gln
                725                 730                 735
Gly Pro Tyr Gly Pro Gly Ala Ser Ala Ala Ala Ala Ala Gly Gly
            740                 745                 750
Tyr Gly Pro Gly Ser Gly Gln Gln Gly Pro Gly Gln Gln Gly Pro
            755                 760                 765
Gly Gln Gly Pro Gly Gly Gln Gly Pro Tyr Gly Pro Gly Ala Ser Ala
            770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gln Gly Pro Tyr Gly Pro Gly Ala
            805                 810                 815
Ser Ala Ala Ser Ala Ala Ser Gly Gly Tyr Gly Pro Gly Ser Gly Gln
            820                 825                 830
Gln Gly Pro Gly Gln Gln Gly Pro Gly Gly Gln Gly Pro Tyr Gly Pro
            835                 840                 845
Gly Ala Ser Ala Ala Ala Ala Ala Gly Gly Tyr Gly Pro Gly Ser
850                 855                 860
Gly Gln Gln Gly Pro Gly Gln Gln Gly Pro Gly Gln Gln Gly Pro Gly
865                 870                 875                 880
Gln Gln Gly Pro Gly Gln Gly Pro Tyr Gly Pro Gly Ala Ser Ala
            885                 890                 895
Ala Ala Ala Ala Gly Gly Tyr Gly Pro Gly Ser Gly Gln Gln Gly
            900                 905                 910
Pro Gly Gln Gln Gly Pro Gly Gln Gln Gly Pro Gly Gln Gln Gly Pro
            915                 920                 925
Gly Gln Gln Gly Pro Gly Gln Gln Gly Pro Gly Gln Gln Gly Pro Gly
            930                 935                 940
Gln Gln Gly Pro Gly Gln Gln Gly Pro Gly Gly Gln Gly Ala Tyr Gly
945                 950                 955                 960
Pro Gly Ala Ser Ala Ala Ala Gly Ala Ala Gly Gly Tyr Gly Pro Gly
                965                 970                 975
Ser Gly Gln Gln Gly Pro Gly Gln Gln Gly Pro Gly Gln Gln Gly Pro
            980                 985                 990
Gly Gln Gln Gly Pro Gly Gln Gln  Gly Pro Gly Gln Gln  Gly Pro Gly
```

```
                     995                1000               1005
Gln Gln  Gly Pro Gly Gln Gln  Gly Pro Tyr Gly Pro  Gly Ala Ser
        1010                1015                1020

Ala Ala  Ala Ala Ala Ala Gly  Gly Tyr Gly Pro Gly  Ser Gly Gln
        1025                1030                1035

Gln Gly  Pro Gly Gln Gln Gly  Pro Gly Gln Gln Gly  Pro Gly Gly
        1040                1045                1050

Gln Gly  Pro Tyr Gly Pro Gly  Ala Ala Ser Ala Ala  Val Ser Val
        1055                1060                1065

Gly Gly  Tyr Gly Pro Gln Ser  Ser Ser Val Pro Val  Ala Ser Ala
        1070                1075                1080

Val Ala  Ser Arg Leu Ser Ser  Pro Ala Ala Ser Ser  Arg Val Ser
        1085                1090                1095

Ser Ala  Val Ser Ser Leu Val  Ser Ser Gly Pro Thr  Lys His Ala
        1100                1105                1110

Ala Leu  Ser Asn Thr Ile Ser  Ser Val Val Ser Gln  Val Ser Ala
        1115                1120                1125

Ser Asn  Pro Gly Leu Ser Gly  Cys Asp Val Leu Val  Gln Ala Leu
        1130                1135                1140

Leu Glu  Val Val Ser Ala Leu  Val Ser Ile Leu
        1145                1150

<210> SEQ ID NO 29
<211> LENGTH: 24
<212> TYPE: PRT
<213> ORGANISM: Artificial Sequence
<220> FEATURE:
<223> OTHER INFORMATION: His tag and start codon

<400> SEQUENCE: 29

Met His His His His His His His His Ser Ser Gly Ser Ser
1               5                   10                  15

Leu Glu Val Leu Phe Gln Gly Pro
                20

<210> SEQ ID NO 30
<211> LENGTH: 597
<212> TYPE: PRT
<213> ORGANISM: Artificial Sequence
<220> FEATURE:
<223> OTHER INFORMATION: Met-PRT380

<400> SEQUENCE: 30

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Ala Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Ala Gly Pro
    50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
                100                 105                 110
```

-continued

```
Gly Pro Gly Ser Ser Ala Ala Ala Ala Gln Gly Tyr Ser Gly
            115                 120                 125

Pro Gly Gln Gln Gly Pro Tyr Gly Ser Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Ser Gly Gln Gln Gly Pro Gly
            180                 185                 190

Gln Tyr Gly Pro Tyr Ala Ser Ala Ala Ala Ala Gly Gln Tyr Gly
    195                 200                 205

Ser Gly Pro Gly Gln Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gln Gln Gly Pro Tyr Gly
            245                 250                 255

Pro Gly Ser Ser Ala Ala Ala Ala Gly Gln Tyr Gly Tyr Gly Pro
            260                 265                 270

Gly Gln Gln Gly Pro Tyr Gly Pro Gly Ala Ser Ala Ala Ala Ala
    275                 280                 285

Gly Gln Asn Gly Pro Gly Ser Gly Gln Tyr Gly Pro Gly Gln Gln Gly
    290                 295                 300

Pro Gly Gln Ser Ala Ala Ala Ala Gly Pro Gly Gln Gln Gly Pro
305                 310                 315                 320

Tyr Gly Pro Gly Ala Ser Ala Ala Ala Gly Gln Tyr Gly Pro
                325                 330                 335

Gly Gln Gln Gly Pro Gly Gln Tyr Gly Pro Gly Ser Ser Ala Ala Ala
            340                 345                 350

Ala Ala Gly Pro Gly Gln Gln Gly Pro Tyr Gly Pro Gly Ser Ser Ala
        355                 360                 365

Ala Ala Ala Gly Gln Tyr Gly Pro Gly Gln Gln Gly Pro Tyr Gly
370                 375                 380

Pro Gly Gln Ser Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala
            405                 410                 415

Gly Pro Gly Gln Gln Gly Pro Tyr Gly Pro Gly Ala Ser Ala Ala Ala
        420                 425                 430

Ala Ala Gly Pro Gly Gln Tyr Gly Pro Gly Gln Gln Gly Pro Ser Ala
            435                 440                 445

Ser Ala Ala Ala Ala Gly Gln Tyr Gly Ser Gly Pro Gly Gln Tyr
450                 455                 460

Gly Pro Tyr Gly Pro Gly Gln Ser Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gln Tyr Gly Pro Gly Gln Gln Gly Pro Tyr Gly Pro
            500                 505                 510

Gly Gln Ser Ala Ala Ala Ala Gly Pro Gly Ser Gly Gln Tyr Gly
    515                 520                 525

Pro Gly Ala Ser Ala Ala Ala Ala Gly Gln Asn Gly Pro Gly Ser
```

```
                530              535              540
Gly Gln Tyr Gly Pro Gly Gln Gly Pro Gln Ser Ala Ala Ala
545                  550              555              560

Ala Ala Gly Gln Tyr Gln Gly Pro Gly Gln Gly Pro Tyr Gly
                565              570              575

Pro Gly Ala Ser Ala Ala Ala Ala Gly Pro Gly Ser Gly Gln Gln
                580              585              590

Gly Pro Gly Ala Ser
        595

<210> SEQ ID NO 31
<211> LENGTH: 590
<212> TYPE: PRT
<213> ORGANISM: Artificial Sequence
<220> FEATURE:
<223> OTHER INFORMATION: Met-PRT410

<400> SEQUENCE: 31

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Gly Gln Tyr Gly Pro Gly Gln Gln Gly Pro Gly Gln Gln Gly
            35                  40                  45

Pro Gly Ser Ser Ala Ala Ala Ala Ala Gly Pro Gly Gln Tyr Gly Pro
        50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Pro Gly Ser Ser Ala Ala Ala Ala Ala
                100                 105                 110

Gly Gln Tyr Gly Ser Gly Pro Gly Gln Gln Gly Pro Tyr Gly Ser Ala
            115                 120                 125

Ala Ala Ala Ala Gly Pro Gly Ser Gly Gln Tyr Gly Gln Gly Pro Tyr
        130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
        260                 265                 270

Tyr Gly Pro Gly Gln Gln Gly Pro Gly Gln Ser Ala Ala Ala Ala
            275                 280                 285

Gly Pro Gly Gln Gln Gly Pro Tyr Gly Pro Gly Ala Ser Ala Ala Ala
```

```
               290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Gly Gln Tyr Gly Pro Gly Gln Gln Gly Pro
            340                 345                 350

Tyr Gly Pro Gly Gln Ser Ala Ala Ala Ala Gly Gln Tyr Gln Gln
        355                 360                 365

Gly Pro Gly Gln Gln Gly Pro Tyr Gly Pro Gly Ala Ser Gly Pro Gly
370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
                405                 410                 415

Ala Ala Ala Gly Gln Tyr Gly Ser Gly Pro Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
    450                 455                 460

Gly Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gly Pro Gly Gln Ser
            500                 505                 510

Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
            580                 585                 590

<210> SEQ ID NO 32
<211> LENGTH: 565
<212> TYPE: PRT
<213> ORGANISM: Artificial Sequence
<220> FEATURE:
<223> OTHER INFORMATION: Met-PRT525

<400> SEQUENCE: 32

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Pro Gly Gln
        35                  40                  45

Gln Gly Pro Gly Ser Ser Ala Ala Ala Ala Ala Gly Pro Gly
    50                  55                  60

Gln Tyr Gly Pro Gly Gln Gln Gly Pro Ser Ala Ser Ala Ala Ala Ala
```

```
            65                  70                  75                  80
Ala Ala Ala Gly Pro Gly Ser Gly Gln Gln Gly Pro Gly Ala Ser Gly
                85                  90                  95
Gln Tyr Gly Pro Gly Gln Gln Gly Pro Gly Gln Gln Gly Pro Gly Ser
                100                 105                 110
Ser Ala Ala Ala Ala Ala Ala Gly Ser Tyr Gly Ser Gly Pro Gly
                115                 120                 125
Gln Gln Gly Pro Tyr Gly Ser Ala Ala Ala Ala Ala Gly Pro
                130                 135                 140
Gly Ser Gly Gln Tyr Gly Gln Gly Pro Tyr Gly Pro Gly Ala Ser Gly
145                 150                 155                 160
Pro Gly Gln Tyr Gly Pro Gly Gln Gly Pro Ser Ala Ser Ala Ala
                165                 170                 175
Ala Ala Ala Ala Ala Gly Ser Gly Gln Gln Gly Pro Gly Gln Tyr Gly
                180                 185                 190
Pro Tyr Ala Ser Ala Ala Ala Ala Ala Gly Ser Tyr Gly Ser
                195                 200                 205
Gly Pro Gly Gln Gln Gly Pro Tyr Gly Pro Gly Gln Ser Gly Ser Gly
                210                 215                 220
Gln Gln Gly Pro Gly Gln Gln Gly Pro Tyr Ala Ser Ala Ala Ala Ala
225                 230                 235                 240
Ala Ala Ala Gly Pro Gly Gln Gln Gly Pro Tyr Gly Pro Gly Ser Ser
                245                 250                 255
Ala Ala Ala Ala Ala Ala Gly Ser Tyr Gly Tyr Gly Pro Gly Gln
                260                 265                 270
Gln Gly Pro Tyr Gly Pro Gly Ala Ser Gly Gln Asn Gly Pro Gly Ser
                275                 280                 285
Gly Gln Tyr Gly Pro Gly Gln Gln Gly Pro Gly Pro Ser Ala Ala Ala
                290                 295                 300
Ala Ala Ala Gly Pro Gly Gln Gln Gly Pro Tyr Gly Pro Gly Ala
305                 310                 315                 320
Ser Ala Ala Ala Ala Ala Ala Gly Ser Tyr Gly Pro Gly Gln Gln
                325                 330                 335
Gly Pro Gly Gln Tyr Gly Pro Gly Ser Ser Gly Pro Gly Gln Gln Gly
                340                 345                 350
Pro Tyr Gly Pro Gly Ser Ser Ala Ala Ala Ala Ala Ala Gly Ser
                355                 360                 365
Tyr Gly Pro Gly Gln Gln Gly Pro Tyr Gly Pro Gly Pro Ser Ala Ala
                370                 375                 380
Ala Ala Ala Ala Ala Gly Ser Tyr Gln Gln Gly Pro Gly Gln Gln Gly
385                 390                 395                 400
Pro Tyr Gly Pro Gly Ala Ser Gly Pro Gly Gln Gln Gly Pro Tyr Gly
                405                 410                 415
Pro Gly Ala Ser Ala Ala Ala Ala Ala Ala Gly Pro Gly Gln Tyr
                420                 425                 430
Gly Pro Gly Gln Gln Gly Pro Ser Ala Ser Ala Ala Ala Ala Ala
                435                 440                 445
Ala Gly Ser Tyr Gly Ser Gly Pro Gly Gln Tyr Gly Pro Tyr Gly Pro
                450                 455                 460
Gly Gln Ser Gly Pro Gly Ser Gly Gln Gly Gln Gly Pro Tyr Gly
465                 470                 475                 480
Pro Gly Ala Ser Ala Ala Ala Ala Ala Ala Gly Ser Tyr Gly Pro
                485                 490                 495
```

-continued

Gly Gln Gln Gly Pro Tyr Gly Pro Gly Ser Ala Ala Ala Ala
            500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
        530                 535                 540

Pro Ser Ala Ala Ala Ala Ala Ala Gly Pro Gly Ser Gly Gln Gln
545                 550                 555                 560

Gly Pro Gly Ala Ser
            565

<210> SEQ ID NO 33
<211> LENGTH: 2364
<212> TYPE: PRT
<213> ORGANISM: Artificial Sequence
<220> FEATURE:
<223> OTHER INFORMATION: Met-PRT799

<400> SEQUENCE: 33

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
            165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Gly Gln Tyr Gly Pro Gly Gln Gln Gly Pro
            340                 345                 350

Tyr Gly Pro Gly Gln Ser Ala Ala Ala Gly Gln Tyr Gln Gln
            355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
    435                 440                 445

Tyr Gly Pro Gly Ala Ser Ala Ala Ala Ala Gly Gln Tyr Gly Pro
    450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
            485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
            565                 570                 575

Ala Ala Gly Pro Gly Ser Gly Gln Gln Gly Pro Gly Ala Ser Gly Gln
            580                 585                 590

Gln Gly Pro Tyr Gly Pro Ala Ser Ala Ala Ala Ala Gly Gln
            595                 600                 605

Asn Gly Pro Gly Ser Gly Gln Gln Gly Pro Gly Gln Ser Gly Gln Tyr
610                 615                 620

Gly Pro Gly Gln Gln Gly Pro Gly Gln Gln Gly Pro Gly Ser Ser Ala
625                 630                 635                 640

Ala Ala Ala Gly Pro Gly Gln Tyr Gly Pro Gly Gln Gln Gly Pro
            645                 650                 655

Ser Ala Ser Ala Ala Ala Ala Gly Pro Gly Ser Gly Gln Gln Gly
            660                 665                 670

Pro Gly Ala Ser Gly Gln Tyr Gly Pro Gly Gln Gln Gly Pro Gly Gln
            675                 680                 685

Gln Gly Pro Gly Ser Ser Ala Ala Ala Ala Gly Gln Tyr Gly Ser
    690                 695                 700

```
Gly Pro Gly Gln Gln Gly Pro Tyr Gly Ser Ala Ala Ala Ala Gly
705                 710                 715                 720

Pro Gly Ser Gly Gln Tyr Gly Gln Gly Pro Tyr Gly Pro Gly Ala Ser
                725                 730                 735

Gly Pro Gly Gln Tyr Gly Pro Gly Gln Gln Gly Pro Ser Ala Ser Ala
            740                 745                 750

Ala Ala Ala Ala Gly Ser Gly Gln Gln Gly Pro Gly Gln Tyr Gly Pro
        755                 760                 765

Tyr Ala Ser Ala Ala Ala Ala Gly Gln Tyr Gly Ser Gly Pro Gly
    770                 775                 780

Gln Gln Gly Pro Tyr Gly Pro Gly Gln Ser Gly Ser Gly Gln Gln Gly
785                 790                 795                 800

Pro Gly Gln Gln Gly Pro Tyr Ala Ser Ala Ala Ala Ala Gly Pro
                805                 810                 815

Gly Gln Gln Gly Pro Tyr Gly Pro Gly Ser Ser Ala Ala Ala Ala
            820                 825                 830

Gly Gln Tyr Gly Tyr Gly Pro Gly Gln Gln Gly Pro Tyr Gly Pro Gly
        835                 840                 845

Ala Ser Gly Gln Asn Gly Pro Gly Ser Gly Gln Tyr Gly Pro Gly Gln
    850                 855                 860

Gln Gly Pro Gly Gln Ser Ala Ala Ala Ala Gly Pro Gly Gln Gln
865                 870                 875                 880

Gly Pro Tyr Gly Pro Gly Ala Ser Ala Ala Ala Ala Gly Gln Tyr
            885                 890                 895

Gly Pro Gly Gln Gln Gly Pro Gly Gln Tyr Gly Pro Gly Ser Ser Gly
        900                 905                 910

Pro Gly Gln Gln Gly Pro Tyr Gly Pro Gly Ser Ser Ala Ala Ala Ala
            915                 920                 925

Ala Gly Gln Tyr Gly Pro Gly Gln Gln Gly Pro Tyr Gly Pro Gly Gln
    930                 935                 940

Ser Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Gly Pro Tyr
            965                 970                 975

Gly Pro Gly Ala Ser Ala Ala Ala Ala Gly Pro Gly Gln Tyr Gly
        980                 985                 990

Pro Gly Gln Gln Gly Pro Ser Ala Ser Ala Ala Ala Ala Gly Gln
                995                 1000                1005

Tyr Gly Ser Gly Pro Gly Gln Tyr Gly Pro Tyr Gly Pro Gly Gln
    1010                1015                1020

Ser Gly Pro Gly Ser Gly Gln Gly Gln Gly Pro Tyr Gly Pro
    1025                1030                1035

Gly Ala Ser Ala Ala Ala Ala Gly Gln Tyr Gly Pro Gly Gln
    1040                1045                1050

Gln Gly Pro Tyr Gly Pro Gly Gln Ser Ala Ala Ala Ala Gly
    1055                1060                1065

Pro Gly Ser Gly Gln Tyr Gly Pro Gly Ala Ser Gly Gln Asn Gly
    1070                1075                1080

Pro Gly Ser Gly Gln Tyr Gly Pro Gly Gln Gly Pro Gly Gln
    1085                1090                1095

Ser Ala Ala Ala Ala Ala Gly Gln Tyr Gln Gln Gly Pro Gly Gln
    1100                1105                1110

Gln Gly Pro Tyr Gly Pro Gly Ala Ser Ala Ala Ala Ala Ala Gly
```

```
            1115                1120                1125

Gln Tyr Gly Ser Gly Pro Gly Gln Gln Gly Pro Tyr Gly Pro Gly
            1130                1135                1140

Gln Ser Gly Ser Gly Gln Gln Gly Pro Gly Gln Gln Gly Pro Tyr
            1145                1150                1155

Ala Ser Ala Ala Ala Ala Ala Gly Pro Gly Ser Gly Gln Gln Gly
            1160                1165                1170

Pro Gly Ala Ser Gly Gln Gln Gly Pro Tyr Gly Pro Gly Ala Ser
            1175                1180                1185

Ala Ala Ala Ala Ala Gly Gln Asn Gly Pro Gly Ser Gly Gln Gln
            1190                1195                1200

Gly Pro Gly Gln Ser Gly Gln Tyr Gly Pro Gly Gln Gln Gly Pro
            1205                1210                1215

Gly Gln Gln Gly Pro Gly Ser Ser Ala Ala Ala Ala Gly Pro
            1220                1225                1230

Gly Gln Tyr Gly Pro Gly Gln Gln Gly Pro Ser Ala Ser Ala Ala
            1235                1240                1245

Ala Ala Ala Gly Pro Gly Ser Gly Gln Gln Gly Pro Gly Ala Ser
            1250                1255                1260

Gly Gln Tyr Gly Pro Gly Gln Gln Gly Pro Gly Gln Gln Gly Pro
            1265                1270                1275

Gly Ser Ser Ala Ala Ala Ala Gly Gln Tyr Gly Ser Gly Pro
            1280                1285                1290

Gly Gln Gln Gly Pro Tyr Gly Ser Ala Ala Ala Ala Ala Gly Pro
            1295                1300                1305

Gly Ser Gly Gln Tyr Gly Gln Gly Pro Tyr Gly Pro Gly Ala Ser
            1310                1315                1320

Gly Pro Gly Gln Tyr Gly Pro Gly Gln Gln Gly Pro Ser Ala Ser
            1325                1330                1335

Ala Ala Ala Ala Ala Gly Ser Gly Gln Gln Gly Pro Gly Gln Tyr
            1340                1345                1350

Gly Pro Tyr Ala Ser Ala Ala Ala Ala Ala Gly Gln Tyr Gly Ser
            1355                1360                1365

Gly Pro Gly Gln Gln Gly Pro Tyr Gly Pro Gly Gln Ser Gly Ser
            1370                1375                1380

Gly Gln Gln Gly Pro Gly Gln Gln Gly Pro Tyr Ala Ser Ala Ala
            1385                1390                1395

Ala Ala Ala Gly Pro Gly Gln Gln Gly Pro Tyr Gly Pro Gly Ser
            1400                1405                1410

Ser Ala Ala Ala Ala Ala Gly Gln Tyr Gly Tyr Gly Pro Gly Gln
            1415                1420                1425

Gln Gly Pro Tyr Gly Pro Gly Ala Ser Gly Gln Asn Gly Pro Gly
            1430                1435                1440

Ser Gly Gln Tyr Gly Pro Gly Gln Gln Gly Pro Gly Gln Ser Ala
            1445                1450                1455

Ala Ala Ala Ala Gly Pro Gly Gln Gln Gly Pro Tyr Gly Pro Gly
            1460                1465                1470

Ala Ser Ala Ala Ala Ala Ala Gly Gln Tyr Gly Pro Gly Gln Gln
            1475                1480                1485

Gly Pro Gly Gln Tyr Gly Pro Gly Ser Ser Gly Pro Gly Gln Gln
            1490                1495                1500

Gly Pro Tyr Gly Pro Gly Ser Ser Ala Ala Ala Ala Ala Gly Gln
            1505                1510                1515
```

```
Tyr Gly Pro Gly Gln Gln Gly Pro Tyr Gly Pro Gly Gln Ser Ala
    1520                1525                1530

Ala Ala Ala Ala Gly Gln Tyr Gln Gln Gly Pro Gly Gln Gln Gly
    1535                1540                1545

Pro Tyr Gly Pro Gly Ala Ser Gly Pro Gly Gln Gln Gly Pro Tyr
    1550                1555                1560

Gly Pro Gly Ala Ser Ala Ala Ala Ala Ala Gly Pro Gly Gln Tyr
    1565                1570                1575

Gly Pro Gly Gln Gln Gly Pro Ser Ala Ser Ala Ala Ala Ala Ala
    1580                1585                1590

Gly Gln Tyr Gly Ser Gly Pro Gly Gln Tyr Gly Pro Tyr Gly Pro
    1595                1600                1605

Gly Gln Ser Gly Pro Gly Ser Gly Gln Gln Gly Gln Gly Pro Tyr
    1610                1615                1620

Gly Pro Gly Ala Ser Ala Ala Ala Ala Ala Gly Gln Tyr Gly Pro
    1625                1630                1635

Gly Gln Gln Gly Pro Tyr Gly Pro Gly Gln Ser Ala Ala Ala Ala
    1640                1645                1650

Ala Gly Pro Gly Ser Gly Gln Tyr Gly Pro Gly Ala Ser Gly Gln
    1655                1660                1665

Asn Gly Pro Gly Ser Gly Gln Tyr Gly Pro Gly Gln Gln Gly Pro
    1670                1675                1680

Gly Gln Ser Ala Ala Ala Ala Ala Gly Gln Tyr Gln Gln Gly Pro
    1685                1690                1695

Gly Gln Gln Gly Pro Tyr Gly Pro Gly Ala Ser Ala Ala Ala Ala
    1700                1705                1710

Ala Gly Gln Tyr Gly Ser Gly Pro Gly Gln Gln Gly Pro Tyr Gly
    1715                1720                1725

Pro Gly Gln Ser Gly Ser Gly Gln Gln Gly Pro Gly Gln Gln Gly
    1730                1735                1740

Pro Tyr Ala Ser Ala Ala Ala Ala Ala Gly Pro Gly Ser Gly Gln
    1745                1750                1755

Gln Gly Pro Gly Ala Ser Gly Gln Gln Gly Pro Tyr Gly Pro Gly
    1760                1765                1770

Ala Ser Ala Ala Ala Ala Ala Gly Gln Asn Gly Pro Gly Ser Gly
    1775                1780                1785

Gln Gln Gly Pro Gly Gln Ser Gly Gln Tyr Gly Pro Gly Gln Gln
    1790                1795                1800

Gly Pro Gly Gln Gln Gly Pro Gly Ser Ser Ala Ala Ala Ala Ala
    1805                1810                1815

Gly Pro Gly Gln Tyr Gly Pro Gly Gln Gln Gly Pro Ser Ala Ser
    1820                1825                1830

Ala Ala Ala Ala Ala Gly Pro Gly Ser Gly Gln Gln Gly Pro Gly
    1835                1840                1845

Ala Ser Gly Gln Tyr Gly Pro Gly Gln Gln Gly Pro Gly Gln Gln
    1850                1855                1860

Gly Pro Gly Ser Ser Ala Ala Ala Ala Ala Gly Gln Tyr Gly Ser
    1865                1870                1875

Gly Pro Gly Gln Gln Gly Pro Tyr Gly Ser Ala Ala Ala Ala Ala
    1880                1885                1890

Gly Pro Gly Ser Gly Gln Tyr Gly Gln Gly Pro Tyr Gly Pro Gly
    1895                1900                1905
```

| | | | | | | | | | | | |
|---|---|---|---|---|---|---|---|---|---|---|---|
| Ala | Ser | Gly | Pro | Gly | Gln | Tyr | Gly | Pro | Gly | Gln | Gln | Gly | Pro | Ser |
| 1910 | | | | | 1915 | | | | | 1920 | |

Ala Ser Gly Pro Gly Gln Tyr Gly Pro Gly Gln Gln Gly Pro Ser
  1910                1915               1920

Ala Ser Ala Ala Ala Ala Ala Gly Ser Gly Gln Gln Gly Pro Gly
  1925                1930               1935

Gln Tyr Gly Pro Tyr Ala Ser Ala Ala Ala Ala Gly Gln Tyr
  1940                1945               1950

Gly Ser Gly Pro Gly Gln Gln Gly Pro Tyr Gly Pro Gly Gln Ser
  1955                1960               1965

Gly Ser Gly Gln Gln Gly Pro Gly Gln Gln Gly Pro Tyr Ala Ser
  1970                1975               1980

Ala Ala Ala Ala Ala Gly Pro Gly Gln Gln Gly Pro Tyr Gly Pro
  1985                1990               1995

Gly Ser Ser Ala Ala Ala Ala Gly Gln Tyr Gly Tyr Gly Pro
  2000                2005               2010

Gly Gln Gln Gly Pro Tyr Gly Pro Gly Ala Ser Gly Gln Asn Gly
  2015                2020               2025

Pro Gly Ser Gly Gln Tyr Gly Pro Gly Gln Gly Pro Gly Gln
  2030                2035               2040

Ser Ala Ala Ala Ala Gly Pro Gly Gln Gln Gly Pro Tyr Gly
  2045                2050               2055

Pro Gly Ala Ser Ala Ala Ala Ala Gly Gln Tyr Gly Pro Gly
  2060                2065               2070

Gln Gln Gly Pro Gly Gln Tyr Gly Pro Gly Ser Ser Gly Pro Gly
  2075                2080               2085

Gln Gln Gly Pro Tyr Gly Pro Gly Ser Ser Ala Ala Ala Ala Ala
  2090                2095               2100

Gly Gln Tyr Gly Pro Gly Gln Gln Gly Pro Tyr Gly Pro Gly Gln
  2105                2110               2115

Ser Ala Ala Ala Ala Gly Gln Tyr Gln Gly Pro Gly Gln
  2120                2125               2130

Gln Gly Pro Tyr Gly Pro Gly Ala Ser Gly Pro Gly Gln Gln Gly
  2135                2140               2145

Pro Tyr Gly Pro Gly Ala Ser Ala Ala Ala Ala Gly Pro Gly
  2150                2155               2160

Gln Tyr Gly Pro Gly Gln Gln Gly Pro Ser Ala Ser Ala Ala Ala
  2165                2170               2175

Ala Ala Gly Gln Tyr Gly Ser Gly Pro Gly Gln Tyr Gly Pro Tyr
  2180                2185               2190

Gly Pro Gly Gln Ser Gly Pro Gly Ser Gly Gln Gln Gly Gln Gly
  2195                2200               2205

Pro Tyr Gly Pro Gly Ala Ser Ala Ala Ala Ala Gly Gln Tyr
  2210                2215               2220

Gly Pro Gly Gln Gln Gly Pro Tyr Gly Pro Gly Gln Ser Ala Ala
  2225                2230               2235

Ala Ala Ala Gly Pro Gly Ser Gly Gln Tyr Gly Pro Gly Ala Ser
  2240                2245               2250

Gly Gln Asn Gly Pro Gly Ser Gly Gln Tyr Gly Pro Gly Gln Gln
  2255                2260               2265

Gly Pro Gly Gln Ser Ala Ala Ala Ala Ala Gly Gln Tyr Gln Gln
  2270                2275               2280

Gly Pro Gly Gln Gln Gly Pro Tyr Gly Pro Gly Ala Ser Ala Ala
  2285                2290               2295

Ala Ala Ala Gly Gln Tyr Gly Ser Gly Pro Gly Gln Gln Gly Pro

```
            2300                2305                2310

Tyr Gly Pro Gly Gln Ser Gly Ser Gly Gln Gln Gly Pro Gly Gln
        2315                2320                2325

Gln Gly Pro Tyr Ala Ser Ala Ala Ala Ala Ala Gly Pro Gly Ser
        2330                2335                2340

Gly Gln Gln Gly Ser Ser Val Asp Lys Leu Ala Ala Ala Leu Glu
        2345                2350                2355

His His His His His His
        2360

<210> SEQ ID NO 34
<211> LENGTH: 597
<212> TYPE: PRT
<213> ORGANISM: Artificial Sequence
<220> FEATURE:
<223> OTHER INFORMATION: Met-PRT313

<400> SEQUENCE: 34

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Ala Gly Gly Tyr Gly Pro Gly Gln Gly
        35                  40                  45

Pro Gly Gln Gln Gly Pro Gly Ser Ser Ala Ala Ala Ala Ala Gly Pro
    50                  55                  60

Gly Gly Tyr Gly Pro Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Ala Gly Gly Tyr Gly Ser Gly
        115                 120                 125

Pro Gly Gln Gln Gly Pro Tyr Gly Ser Ala Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Ala Gly Pro Gly Gly Tyr Gly Pro Gly Gln Gln Gly Pro
                165                 170                 175

Ser Ala Ser Ala Ala Ala Ala Gly Ser Gly Gln Gln Gly Pro Gly
            180                 185                 190

Gly Tyr Gly Pro Tyr Ala Ser Ala Ala Ala Ala Gly Gly Tyr Gly
        195                 200                 205

Ser Gly Pro Gly Gln Gln Gly Pro Tyr Gly Pro Gly Gly Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gly Gln Gly Pro Tyr Gly
                245                 250                 255

Pro Gly Ser Ser Ala Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala Ala
        275                 280                 285

Gly Gly Asn Gly Pro Gly Ser Gly Gly Tyr Gly Pro Gly Gln Gln Gly
```

```
            290                 295                 300

Pro Gly Gly Ser Ala Ala Ala Ala Gly Pro Gly Gln Gly Pro
305                 310                 315                 320

Tyr Gly Pro Gly Ala Ser Ala Ala Ala Ala Gly Gly Tyr Gly Pro
                325                 330                 335

Gly Gly Gln Gly Pro Gly Gly Tyr Gly Pro Gly Ser Ser Ala Ala
                340                 345                 350

Ala Ala Gly Pro Gly Gly Gln Gly Pro Tyr Gly Pro Gly Ser Ser Ala
            355                 360                 365

Ala Ala Ala Gly Gly Tyr Gly Pro Gly Gln Gln Gly Pro Tyr Gly
            370                 375                 380

Pro Gly Gly Ser Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala
                405                 410                 415

Gly Pro Gly Gly Gln Gly Pro Tyr Gly Pro Gly Ala Ser Ala Ala
                420                 425                 430

Ala Ala Gly Pro Gly Gly Tyr Gly Pro Gly Gly Gln Gly Pro Ser Ala
            435                 440                 445

Ser Ala Ala Ala Ala Gly Gly Tyr Gly Ser Gly Pro Gly Gly Tyr
    450                 455                 460

Gly Pro Tyr Gly Pro Gly Gly Ser Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gly Tyr Gly Pro Gly Gln Gln Gly Pro Tyr Gly Pro
                500                 505                 510

Gly Gly Ser Ala Ala Ala Ala Gly Pro Gly Ser Gly Gly Tyr Gly
            515                 520                 525

Pro Gly Ala Ser Ala Ala Ala Ala Gly Gly Asn Gly Pro Gly Ser
530                 535                 540

Gly Gly Tyr Gly Pro Gly Gln Gln Gly Pro Gly Gly Ser Ala Ala Ala
545                 550                 555                 560

Ala Ala Gly Gly Tyr Gln Gln Gly Pro Gly Gln Gly Pro Tyr Gly
                565                 570                 575

Pro Gly Ala Ser Ala Ala Ala Ala Gly Pro Gly Ser Gly Gln Gln
                580                 585                 590

Gly Pro Gly Ala Ser
            595

<210> SEQ ID NO 35
<211> LENGTH: 12
<212> TYPE: PRT
<213> ORGANISM: Artificial Sequence
<220> FEATURE:
<223> OTHER INFORMATION: HisTag

<400> SEQUENCE: 35

Met His His His His His His Ser Ser Gly Ser Ser
1               5                   10

<210> SEQ ID NO 36
<211> LENGTH: 608
<212> TYPE: PRT
<213> ORGANISM: Artificial Sequence
<220> FEATURE:
<223> OTHER INFORMATION: PRT380
```

<400> SEQUENCE: 36

Met His His His His His Ser Ser Gly Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Ala Ala
        35                  40                  45

Ala Ala Gly Gln Tyr Gly Pro Gly Gln Gln Gly Pro Gly Gln Gln Gly
    50                  55                  60

Pro Gly Ser Ser Ala Ala Ala Ala Gly Pro Gly Gln Tyr Gly Pro
65              70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gln
                100                 105                 110

Tyr Gly Pro Gly Gln Gln Gly Pro Gln Gln Gly Pro Gly Ser Ser
            115                 120                 125

Ala Ala Ala Ala Ala Gly Gln Tyr Gly Ser Gly Pro Gly Gln Gln Gly
    130                 135                 140

Pro Tyr Gly Ser Ala Ala Ala Ala Gly Pro Gly Ser Gly Gln Tyr
145                 150                 155                 160

Gly Gln Gly Pro Tyr Gly Pro Gly Ala Ser Ala Ala Ala Ala Gly
            165                 170                 175

Pro Gly Gln Tyr Gly Pro Gly Gln Gln Gly Pro Ser Ala Ser Ala Ala
            180                 185                 190

Ala Ala Ala Gly Ser Gly Gln Gln Gly Pro Gly Gln Tyr Gly Pro Tyr
    195                 200                 205

Ala Ser Ala Ala Ala Ala Gly Gln Tyr Gly Ser Gly Pro Gly Gln
210                 215                 220

Gln Gly Pro Tyr Gly Pro Gly Gln Ser Ala Ala Ala Ala Gly Ser
225                 230                 235                 240

Gly Gln Gln Gly Pro Gly Gln Gln Gly Pro Tyr Ala Ser Ala Ala Ala
            245                 250                 255

Ala Ala Gly Pro Gly Gln Gln Gly Pro Tyr Gly Pro Gly Ser Ser Ala
            260                 265                 270

Ala Ala Ala Gly Gln Tyr Gly Tyr Gly Pro Gly Gln Gln Gly Pro
    275                 280                 285

Tyr Gly Pro Gly Ala Ser Ala Ala Ala Ala Gly Gln Asn Gly Pro
290                 295                 300

Gly Ser Gly Gln Tyr Gly Pro Gly Gln Gln Gly Pro Gly Gln Ser Ala
305                 310                 315                 320

Ala Ala Ala Gly Pro Gly Gln Gln Gly Pro Tyr Gly Pro Gly Ala
            325                 330                 335

Ser Ala Ala Ala Ala Gly Gln Tyr Gly Pro Gly Gln Gln Gly Pro
            340                 345                 350

Gly Gln Tyr Gly Pro Gly Ser Ser Ala Ala Ala Ala Gly Pro Gly
            355                 360                 365

Gln Gln Gly Pro Tyr Gly Pro Gly Ser Ser Ala Ala Ala Ala Gly
            370                 375                 380

Gln Tyr Gly Pro Gly Gln Gln Gly Pro Tyr Gly Pro Gly Gln Ser Ala
385                 390                 395                 400

Ala Ala Ala Gly Gln Tyr Gln Gln Gly Pro Gly Gln Gln Gly Pro

```
                405                 410                 415
Tyr Gly Pro Gly Ala Ser Ala Ala Ala Ala Gly Pro Gly Gln Gln
            420                 425                 430

Gly Pro Tyr Gly Pro Gly Ala Ser Ala Ala Ala Ala Gly Pro Gly
        435                 440                 445

Gln Tyr Gly Pro Gly Gln Gln Gly Pro Ser Ala Ser Ala Ala Ala
    450                 455                 460

Ala Gly Gln Tyr Gly Ser Gly Pro Gly Gln Tyr Gly Tyr Gly Pro
465                 470                 475                 480

Gly Gln Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gln
        500                 505                 510

Tyr Gly Pro Gly Gln Gln Gly Pro Tyr Gly Pro Gly Gln Ser Ala Ala
    515                 520                 525

Ala Ala Ala Gly Pro Gly Ser Gly Gln Tyr Gly Pro Gly Ala Ser Ala
530                 535                 540

Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Gly Gln Tyr
            565                 570                 575

Gln Gln Gly Pro Gly Gln Gly Pro Tyr Gly Pro Gly Ala Ser Ala
        580                 585                 590

Ala Ala Ala Gly Pro Gly Ser Gly Gln Gln Gly Pro Gly Ala Ser
        595                 600                 605
```

<210> SEQ ID NO 37
<211> LENGTH: 601
<212> TYPE: PRT
<213> ORGANISM: Artificial Sequence
<220> FEATURE:
<223> OTHER INFORMATION: PRT410

<400> SEQUENCE: 37

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gln Tyr Gly Pro Gly Gln Gln Gly Pro Gly Gln
        100                 105                 110

Gln Gly Pro Gly Ser Ser Ala Ala Ala Ala Gly Gln Tyr Gly Ser
    115                 120                 125

Gly Pro Gly Gln Gln Gly Pro Tyr Gly Ser Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
```

```
                165                 170                 175
Ala Ala Ala Ala Gly Ser Gly Gln Gln Gly Pro Gly Gln Tyr Gly Pro
                180                 185                 190

Tyr Ala Ser Ala Ala Ala Ala Ala Gly Gln Tyr Gly Ser Gly Pro Gly
                195                 200                 205

Gln Gln Gly Pro Tyr Gly Pro Gly Gln Ser Gly Ser Gly Gln Gln Gly
                210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
                260                 265                 270

Ala Ser Gly Gln Asn Gly Pro Gly Ser Gly Gln Tyr Gly Pro Gly Gln
                275                 280                 285

Gln Gly Pro Gly Gln Ser Ala Ala Ala Ala Gly Pro Gly Gln Gln
                290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala
                340                 345                 350

Ala Gly Gln Tyr Gly Pro Gly Gln Gln Gly Pro Tyr Gly Pro Gly Gln
                355                 360                 365

Ser Ala Ala Ala Ala Gly Gln Tyr Gln Gln Gly Pro Gly Gln Gln
                370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
                435                 440                 445

Gly Pro Gly Ser Gly Gln Gln Gly Gln Gly Pro Tyr Gly Pro Gly Ala
                450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
                500                 505                 510

Tyr Gly Pro Gly Gln Gln Gly Pro Gly Gln Ser Ala Ala Ala Ala
                515                 520                 525

Gly Gln Tyr Gln Gln Gly Pro Gly Gln Gln Gly Pro Tyr Gly Pro Gly
                530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590
```

-continued

Ser Gly Gln Gln Gly Pro Gly Ala Ser
        595                 600

<210> SEQ ID NO 38
<211> LENGTH: 576
<212> TYPE: PRT
<213> ORGANISM: Artificial Sequence
<220> FEATURE:
<223> OTHER INFORMATION: PRT525

<400> SEQUENCE: 38

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gln Ser Gly
            35                  40                  45

Gln Tyr Gly Pro Gly Gln Gln Gly Pro Gly Gln Gln Gly Pro Gly Ser
50                      55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
                85                  90                  95

Gly Ser Gly Gln Gln Gly Pro Ala Ser Gly Gln Tyr Gly Pro Gly
                100                 105                 110

Gln Gln Gly Pro Gly Gln Gln Gly Pro Gly Ser Ser Ala Ala Ala
                115                 120                 125

Ala Ala Ala Gly Ser Tyr Gly Ser Gly Pro Gly Gln Gln Gly Pro Tyr
            130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala
                180                 185                 190

Gly Ser Gly Gln Gln Gly Pro Gly Gln Tyr Gly Pro Tyr Ala Ser Ala
            195                 200                 205

Ala Ala Ala Ala Ala Gly Ser Tyr Gly Ser Gly Pro Gly Gln Gln
            210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
                245                 250                 255

Gly Gln Gln Gly Pro Tyr Gly Pro Gly Ser Ser Ala Ala Ala Ala
                260                 265                 270

Ala Ala Gly Ser Tyr Gly Tyr Gly Pro Gly Gln Gln Gly Pro Tyr Gly
            275                 280                 285

Pro Gly Ala Ser Gly Gln Asn Gly Pro Gly Ser Gly Gln Tyr Gly Pro
290                 295                 300

Gly Gln Gln Gly Pro Gly Pro Ser Ala Ala Ala Ala Ala Ala Gly
305                 310                 315                 320

Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
            355                 360                 365

Ser Ser Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gln Gln Gly Pro Tyr Gly Pro Gly
                405                 410                 415

Ala Ser Gly Pro Gly Gln Gln Gly Pro Tyr Gly Pro Gly Ala Ser Ala
                420                 425                 430

Ala Ala Ala Ala Ala Gly Pro Gly Gln Tyr Gly Pro Gly Gln Gln
            435                 440                 445

Gly Pro Ser Ala Ser Ala Ala Ala Ala Ala Gly Ser Tyr Gly
            450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
                485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
            530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575

<210> SEQ ID NO 39
<211> LENGTH: 2375
<212> TYPE: PRT
<213> ORGANISM: Artificial Sequence
<220> FEATURE:
<223> OTHER INFORMATION: PRT799

<400> SEQUENCE: 39

Met His His His His His His Ser Ser Gly Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gln Gln Gly Pro Gly Ser Ser Ala
    50                  55                  60

Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Ala Gly
            130                 135                 140

```
Pro Gly Ser Gly Gln Tyr Gln Gly Pro Tyr Pro Gly Ala Ser
145                 150                 155                 160

Gly Pro Gly Gln Tyr Gly Pro Gly Gln Gly Pro Ser Ala Ser Ala
            165                 170                 175

Ala Ala Ala Ala Gly Ser Gly Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Ser Gly Ser Gly Gln Gln Gly
        210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gln Gly Pro Tyr Gly Pro Gly
        260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
        290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Gly Gln Tyr Gln Gly Pro Gly Gln Gln
370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
            450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
            515                 520                 525

Gly Gln Tyr Gln Gln Gly Pro Gly Gln Gln Gly Pro Tyr Gly Pro Gly
        530                 535                 540

Ala Ser Ala Ala Ala Ala Ala Gly Gln Tyr Gly Ser Gly Pro Gly Gln
545                 550                 555                 560
```

Gln Gly Pro Tyr Gly Pro Gly Gln Ser Gly Gln Gln Gly Pro
              565                 570                 575

Gly Gln Gln Gly Pro Tyr Ala Ser Ala Ala Ala Ala Gly Pro Gly
          580                 585                 590

Ser Gly Gln Gln Gly Pro Gly Ala Ser Gly Gln Gln Gly Pro Tyr Gly
          595                 600                 605

Pro Gly Ala Ser Ala Ala Ala Ala Gly Gln Asn Gly Pro Gly Ser
          610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ala Ala Ala Ala Gly
              645                 650                 655

Pro Gly Gln Tyr Gly Pro Gly Gln Gln Gly Pro Ser Ala Ser Ala Ala
              660                 665                 670

Ala Ala Ala Gly Pro Gly Ser Gly Gln Gln Gly Pro Gly Ala Ser Gly
          675                 680                 685

Gln Tyr Gly Pro Gly Gln Gln Gly Pro Gly Gln Gln Gly Pro Gly Ser
690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
              725                 730                 735

Tyr Gly Gln Gly Pro Tyr Gly Pro Gly Ala Ser Gly Pro Gly Gln Tyr
              740                 745                 750

Gly Pro Gly Gln Gln Gly Pro Ser Ala Ser Ala Ala Ala Ala Gly
              755                 760                 765

Ser Gly Gln Gln Gly Pro Gly Gln Tyr Gly Pro Tyr Ala Ser Ala Ala
          770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
              805                 810                 815

Pro Tyr Ala Ser Ala Ala Ala Ala Gly Pro Gly Gln Gln Gly Pro
          820                 825                 830

Tyr Gly Pro Gly Ser Ser Ala Ala Ala Ala Gly Gln Tyr Gly Tyr
          835                 840                 845

Gly Pro Gly Gln Gln Gly Pro Tyr Gly Pro Gly Ala Ser Gly Gln Asn
              850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gly Gln Gln Gly Pro Tyr Gly Pro
              885                 890                 895

Gly Ala Ser Ala Ala Ala Ala Gly Gln Tyr Gly Pro Gly Gln Gln
          900                 905                 910

Gly Pro Gly Gln Tyr Gly Pro Gly Ser Ser Gly Pro Gly Gln Gln Gly
              915                 920                 925

Pro Tyr Gly Pro Gly Ser Ser Ala Ala Ala Ala Gly Gln Tyr Gly
          930                 935                 940

Pro Gly Gln Gln Gly Pro Tyr Gly Pro Gly Ser Ala Ala Ala Ala
945                 950                 955                 960

Ala Gly Gln Tyr Gln Gln Gly Pro Gly Gln Gln Gly Pro Tyr Gly Pro
              965                 970                 975

Gly Ala Ser Gly Pro Gly Gln Gln Gly Pro Tyr Gly Pro Gly Ala Ser 980             985             990
Ala Ala Ala Ala Ala Gly Pro Gly  Gln Tyr Gly Pro Gly  Gln Gln Gly
                995             1000            1005

Pro Ser  Ala Ser Ala Ala  Ala Ala Gly Gln Tyr  Gly Ser Gly
    1010         1015             1020

Pro Gly  Gln Tyr Gly Pro Tyr  Gly Pro Gly Gln Ser  Gly Pro Gly
    1025             1030             1035

Ser Gly  Gln Gln Gly Gln Gly  Pro Tyr Gly Pro Gly  Ala Ser Ala
    1040             1045             1050

Ala Ala  Ala Ala Gly Gln Tyr  Gly Pro Gly Gln Gln  Gly Pro Tyr
    1055             1060             1065

Gly Pro  Gly Gln Ser Ala Ala  Ala Ala Gly Pro  Gly Ser Gly
    1070             1075             1080

Gln Tyr  Gly Pro Gly Ala Ser  Gly Gln Asn Gly Pro  Gly Ser Gly
    1085             1090             1095

Gln Tyr  Gly Pro Gly Gln Gln  Gly Pro Gly Gln Ser  Ala Ala Ala
    1100             1105             1110

Ala Ala  Gly Gln Tyr Gln Gln  Gly Pro Gly Gln Gln  Gly Pro Tyr
    1115             1120             1125

Gly Pro  Gly Ala Ser Ala Ala  Ala Ala Gly Gln  Tyr Gly Ser
    1130             1135             1140

Gly Pro  Gly Gln Gln Gly Pro  Tyr Gly Pro Gly Gln  Ser Gly Ser
    1145             1150             1155

Gly Gln  Gln Gly Pro Gly Gln  Gln Gly Pro Tyr Ala  Ser Ala Ala
    1160             1165             1170

Ala Ala  Ala Gly Pro Gly Ser  Gly Gln Gln Gly Pro  Gly Ala Ser
    1175             1180             1185

Gly Gln  Gln Gly Pro Tyr Gly  Pro Gly Ala Ser Ala  Ala Ala Ala
    1190             1195             1200

Ala Gly  Gln Asn Gly Pro Gly  Ser Gly Gln Gln Gly  Pro Gly Gln
    1205             1210             1215

Ser Gly  Gln Tyr Gly Pro Gly  Gln Gln Gly Pro Gly  Gln Gln Gly
    1220             1225             1230

Pro Gly  Ser Ser Ala Ala Ala  Ala Ala Gly Pro Gly  Gln Tyr Gly
    1235             1240             1245

Pro Gly  Gln Gln Gly Pro Ser  Ala Ser Ala Ala  Ala Ala Gly
    1250             1255             1260

Pro Gly  Ser Gly Gln Gln Gly  Pro Gly Ala Ser Gly  Gln Tyr Gly
    1265             1270             1275

Pro Gly  Gln Gln Gly Pro Gly  Gln Gln Gly Pro Gly  Ser Ser Ala
    1280             1285             1290

Ala Ala  Ala Ala Gly Gln Tyr  Gly Ser Gly Pro Gly  Gln Gln Gly
    1295             1300             1305

Pro Tyr  Gly Ser Ala Ala Ala  Ala Ala Gly Pro Gly  Ser Gly Gln
    1310             1315             1320

Tyr Gly  Gln Gly Pro Tyr Gly  Pro Gly Ala Ser Gly  Pro Gly Gln
    1325             1330             1335

Tyr Gly  Pro Gly Gln Gln Gly  Pro Ser Ala Ser Ala  Ala Ala Ala
    1340             1345             1350

Ala Gly  Ser Gly Gln Gln Gly  Pro Gly Gln Tyr Gly  Pro Tyr Ala
    1355             1360             1365

Ser Ala  Ala Ala Ala Ala Gly  Gln Tyr Gly Ser Gly  Pro Gly Gln
    1370             1375             1380

```
Gln Gly Pro Tyr Gly Pro Gly Gln Ser Gly Ser Gly Gln Gln Gly
    1385                1390                1395

Pro Gly Gln Gln Gly Pro Tyr Ala Ser Ala Ala Ala Ala Ala Gly
    1400                1405                1410

Pro Gly Gln Gln Gly Pro Tyr Gly Pro Gly Ser Ser Ala Ala Ala
    1415                1420                1425

Ala Ala Gly Gln Tyr Gly Tyr Gly Pro Gly Gln Gln Gly Pro Tyr
    1430                1435                1440

Gly Pro Gly Ala Ser Gly Gln Asn Gly Pro Gly Ser Gly Gln Tyr
    1445                1450                1455

Gly Pro Gly Gln Gln Gly Pro Gly Gln Ser Ala Ala Ala Ala Ala
    1460                1465                1470

Gly Pro Gly Gln Gln Gly Pro Tyr Gly Pro Gly Ala Ser Ala Ala
    1475                1480                1485

Ala Ala Ala Gly Gln Tyr Gly Pro Gly Gln Gln Gly Pro Gly Gln
    1490                1495                1500

Tyr Gly Pro Gly Ser Ser Gly Pro Gly Gln Gln Gly Pro Tyr Gly
    1505                1510                1515

Pro Gly Ser Ser Ala Ala Ala Ala Ala Gly Gln Tyr Gly Pro Gly
    1520                1525                1530

Gln Gln Gly Pro Tyr Gly Pro Gly Gln Ser Ala Ala Ala Ala Ala
    1535                1540                1545

Gly Gln Tyr Gln Gln Gly Pro Gly Gln Gln Gly Pro Tyr Gly Pro
    1550                1555                1560

Gly Ala Ser Gly Pro Gly Gln Gln Gly Pro Tyr Gly Pro Gly Ala
    1565                1570                1575

Ser Ala Ala Ala Ala Ala Gly Pro Gly Tyr Gly Pro Gly Gln
    1580                1585                1590

Gln Gly Pro Ser Ala Ser Ala Ala Ala Ala Gly Gln Tyr Gly
    1595                1600                1605

Ser Gly Pro Gly Gln Tyr Gly Pro Tyr Gly Pro Gly Gln Ser Gly
    1610                1615                1620

Pro Gly Ser Gly Gln Gln Gly Gln Gly Pro Tyr Gly Pro Gly Ala
    1625                1630                1635

Ser Ala Ala Ala Ala Gly Gln Tyr Gly Pro Gly Gln Gln Gly
    1640                1645                1650

Pro Tyr Gly Pro Gly Gln Ser Ala Ala Ala Ala Gly Pro Gly
    1655                1660                1665

Ser Gly Gln Tyr Gly Pro Gly Ala Ser Gly Gln Asn Gly Pro Gly
    1670                1675                1680

Ser Gly Gln Tyr Gly Pro Gly Gln Gln Gly Pro Gly Gln Ser Ala
    1685                1690                1695

Ala Ala Ala Gly Gln Tyr Gln Gln Gly Pro Gly Gln Gln Gly
    1700                1705                1710

Pro Tyr Gly Pro Gly Ala Ser Ala Ala Ala Ala Gly Gln Tyr
    1715                1720                1725

Gly Ser Gly Pro Gly Gln Gln Gly Pro Tyr Gly Pro Gly Gln Ser
    1730                1735                1740

Gly Ser Gly Gln Gln Gly Pro Gly Gln Gly Pro Tyr Ala Ser
    1745                1750                1755

Ala Ala Ala Ala Gly Pro Gly Ser Gly Gln Gln Gly Pro Gly
    1760                1765                1770
```

```
Ala Ser Gly Gln Gln Gly Pro Tyr Gly Pro Gly Ala Ser Ala Ala
    1775                1780                1785
Ala Ala Ala Gly Gln Asn Gly Pro Gly Ser Gly Gln Gln Gly Pro
    1790                1795                1800
Gly Gln Ser Gly Gln Tyr Gly Pro Gly Gln Gln Gly Pro Gly Gln
    1805                1810                1815
Gln Gly Pro Gly Ser Ser Ala Ala Ala Ala Gly Pro Gly Gln
    1820                1825                1830
Tyr Gly Pro Gly Gln Gln Gly Pro Ser Ala Ser Ala Ala Ala Ala
    1835                1840                1845
Ala Gly Pro Gly Ser Gly Gln Gln Gly Pro Gly Ala Ser Gly Gln
    1850                1855                1860
Tyr Gly Pro Gly Gln Gln Gly Pro Gly Gln Gln Gly Pro Gly Ser
    1865                1870                1875
Ser Ala Ala Ala Ala Gly Gln Tyr Gly Ser Gly Pro Gly Gln
    1880                1885                1890
Gln Gly Pro Tyr Gly Ser Ala Ala Ala Ala Gly Pro Gly Ser
    1895                1900                1905
Gly Gln Tyr Gly Gln Gly Pro Tyr Gly Pro Gly Ala Ser Gly Pro
    1910                1915                1920
Gly Gln Tyr Gly Pro Gly Gln Gln Gly Pro Ser Ala Ser Ala Ala
    1925                1930                1935
Ala Ala Ala Gly Ser Gly Gln Gln Gly Pro Gly Gln Tyr Gly Pro
    1940                1945                1950
Tyr Ala Ser Ala Ala Ala Ala Gly Gln Tyr Gly Ser Gly Pro
    1955                1960                1965
Gly Gln Gln Gly Pro Tyr Gly Pro Gly Gln Ser Gly Ser Gly Gln
    1970                1975                1980
Gln Gly Pro Gly Gln Gln Gly Pro Tyr Ala Ser Ala Ala Ala Ala
    1985                1990                1995
Ala Gly Pro Gly Gln Gln Gly Pro Tyr Gly Pro Gly Ser Ser Ala
    2000                2005                2010
Ala Ala Ala Ala Gly Gln Tyr Gly Tyr Gly Pro Gly Gln Gln Gly
    2015                2020                2025
Pro Tyr Gly Pro Gly Ala Ser Gly Gln Asn Gly Pro Gly Ser Gly
    2030                2035                2040
Gln Tyr Gly Pro Gly Gln Gln Gly Pro Gly Gln Ser Ala Ala Ala
    2045                2050                2055
Ala Ala Gly Pro Gly Gln Gln Gly Pro Tyr Gly Pro Gly Ala Ser
    2060                2065                2070
Ala Ala Ala Ala Gly Gln Tyr Gly Pro Gly Gln Gln Gly Pro
    2075                2080                2085
Gly Gln Tyr Gly Pro Gly Ser Ser Gly Pro Gly Gln Gln Gly Pro
    2090                2095                2100
Tyr Gly Pro Gly Ser Ser Ala Ala Ala Ala Gly Gln Tyr Gly
    2105                2110                2115
Pro Gly Gln Gln Gly Pro Tyr Gly Pro Gly Gln Ser Ala Ala Ala
    2120                2125                2130
Ala Ala Gly Gln Tyr Gln Gln Gly Pro Gly Gln Gln Gly Pro Tyr
    2135                2140                2145
Gly Pro Gly Ala Ser Gly Pro Gly Gln Gln Gly Pro Tyr Gly Pro
    2150                2155                2160
Gly Ala Ser Ala Ala Ala Ala Ala Gly Pro Gly Gln Tyr Gly Pro
```

```
                    2165                2170                2175

Gly Gln Gln Gly Pro Ser Ala Ser Ala Ala Ala Ala Gly Gln
                2180                2185                2190

Tyr Gly Ser Gly Pro Gly Gln Tyr Gly Pro Tyr Gly Pro Gly Gln
            2195                2200                2205

Ser Gly Pro Gly Ser Gly Gln Gln Gly Gln Gly Pro Tyr Gly Pro
        2210                2215                2220

Gly Ala Ser Ala Ala Ala Ala Gly Gln Tyr Gly Pro Gly Gln
    2225                2230                2235

Gln Gly Pro Tyr Gly Pro Gly Gln Ser Ala Ala Ala Ala Ala Gly
    2240                2245                2250

Pro Gly Ser Gly Gln Tyr Gly Pro Gly Ala Ser Gly Gln Asn Gly
    2255                2260                2265

Pro Gly Ser Gly Gln Tyr Gly Pro Gly Gln Gly Pro Gly Gln
    2270                2275                2280

Ser Ala Ala Ala Ala Gly Gln Tyr Gln Gln Gly Pro Gly Gln
    2285                2290                2295

Gln Gly Pro Tyr Gly Pro Gly Ala Ser Ala Ala Ala Ala Gly
    2300                2305                2310

Gln Tyr Gly Ser Gly Pro Gly Gln Gln Gly Pro Tyr Gly Pro Gly
    2315                2320                2325

Gln Ser Gly Ser Gly Gln Gln Gly Pro Gly Gln Gln Gly Pro Tyr
    2330                2335                2340

Ala Ser Ala Ala Ala Ala Gly Pro Gly Ser Gly Gln Gln Gly
    2345                2350                2355

Ser Ser Val Asp Lys Leu Ala Ala Ala Leu Glu His His His His
    2360                2365                2370

His His
    2375

<210> SEQ ID NO 40
<211> LENGTH: 608
<212> TYPE: PRT
<213> ORGANISM: Artificial Sequence
<220> FEATURE:
<223> OTHER INFORMATION: PRT313

<400> SEQUENCE: 40

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Ala Ala
            35                  40                  45

Ala Ala Gly Gly Tyr Gly Pro Gly Gln Gly Pro Gly Gln Gln Gly
        50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
                100                 105                 110

Tyr Gly Pro Gly Gly Gln Gly Pro Gly Gln Gln Gly Pro Gly Ser Ser
            115                 120                 125

Ala Ala Ala Ala Ala Gly Gly Tyr Gly Ser Gly Pro Gly Gln Gln Gly
```

-continued

```
            130                 135                 140
Pro Tyr Gly Ser Ala Ala Ala Gly Pro Gly Ser Gly Tyr
145                 150                 155                 160

Gly Gln Gly Pro Tyr Gly Pro Gly Ala Ser Ala Ala Ala Ala Gly
                165                 170                 175

Pro Gly Gly Tyr Gly Pro Gly Gly Gln Gly Pro Ser Ala Ser Ala Ala
                180                 185                 190

Ala Ala Ala Gly Ser Gln Gln Gly Pro Gly Gly Tyr Gly Pro Tyr
                195                 200                 205

Ala Ser Ala Ala Ala Ala Gly Gly Tyr Gly Ser Gly Pro Gly Gln
210                 215                 220

Gln Gly Pro Tyr Gly Pro Gly Ser Ala Ala Ala Ala Gly Ser
225                 230                 235                 240

Gly Gln Gln Gly Pro Gly Gln Gln Gly Pro Tyr Ala Ser Ala Ala Ala
                245                 250                 255

Ala Ala Gly Pro Gly Gly Gln Gly Pro Tyr Gly Pro Gly Ser Ser Ala
                260                 265                 270

Ala Ala Ala Gly Gly Tyr Gly Tyr Gly Pro Gly Gly Gln Gly Pro
                275                 280                 285

Tyr Gly Pro Gly Ala Ser Ala Ala Ala Ala Gly Gly Asn Gly Pro
290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
                325                 330                 335

Ser Ala Ala Ala Ala Gly Gly Tyr Gly Pro Gly Gly Gln Gly Pro
                340                 345                 350

Gly Gly Tyr Gly Pro Gly Ser Ser Ala Ala Ala Ala Gly Pro Gly
                355                 360                 365

Gly Gln Gly Pro Tyr Gly Pro Gly Ser Ser Ala Ala Ala Ala Gly
                370                 375                 380

Gly Tyr Gly Pro Gly Gln Gln Gly Pro Tyr Gly Pro Gly Gly Ser Ala
385                 390                 395                 400

Ala Ala Ala Gly Gly Tyr Gln Gln Gly Pro Gly Gln Gly Pro
                405                 410                 415

Tyr Gly Pro Gly Ala Ser Ala Ala Ala Ala Gly Pro Gly Gly Gln
                420                 425                 430

Gly Pro Tyr Gly Pro Gly Ala Ser Ala Ala Ala Ala Gly Pro Gly
                435                 440                 445

Gly Tyr Gly Pro Gly Gly Gln Gly Pro Ser Ala Ser Ala Ala Ala
                450                 455                 460

Ala Gly Gly Tyr Gly Ser Gly Pro Gly Gly Tyr Gly Tyr Gly Pro
465                 470                 475                 480

Gly Gly Ser Ala Ala Ala Ala Gly Pro Gly Ser Gly Gln Gln Gly
                485                 490                 495

Gln Gly Pro Tyr Gly Pro Gly Ala Ser Ala Ala Ala Ala Gly Gly
                500                 505                 510

Tyr Gly Pro Gly Gln Gln Gly Pro Tyr Gly Pro Gly Gly Ser Ala Ala
                515                 520                 525

Ala Ala Ala Gly Pro Gly Ser Gly Gly Tyr Gly Pro Gly Ala Ser Ala
                530                 535                 540

Ala Ala Ala Gly Gly Asn Gly Pro Gly Ser Gly Gly Tyr Gly Pro
545                 550                 555                 560
```

Gly Gln Gln Gly Pro Gly Ser Ala Ala Ala Ala Gly Tyr
              565                 570                 575

Gln Gln Gly Pro Gly Gly Gln Gly Pro Tyr Gly Pro Gly Ala Ser Ala
         580                 585                 590

Ala Ala Ala Ala Gly Pro Gly Ser Gly Gln Gln Gly Pro Gly Ala Ser
         595                 600                 605

<210> SEQ ID NO 41
<211> LENGTH: 590
<212> TYPE: PRT
<213> ORGANISM: Artificial Sequence
<220> FEATURE:
<223> OTHER INFORMATION: Met-PRT399

<400> SEQUENCE: 41

Met Gly Pro Gly Gly Gln Gly Pro Tyr Gly Pro Gly Ala Ser Ala Ala
1               5                  10                  15

Ala Ala Ala Gly Gly Asn Gly Pro Gly Ser Gly Gln Gln Gly Pro Gly
             20                  25                  30

Gly Ser Gly Gly Tyr Gly Pro Gly Gln Gly Pro Gly Gln Gln Gly
         35                  40                  45

Pro Gly Ser Ser Ala Ala Ala Ala Gly Pro Gly Gly Tyr Gly Pro
    50                  55                  60

Gly Gly Gln Gly Pro Ser Ala Ser Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala
             100                 105                 110

Gly Gly Tyr Gly Ser Gly Pro Gly Gln Gln Gly Pro Tyr Gly Ser Ala
             115                 120                 125

Ala Ala Ala Ala Gly Pro Gly Ser Gly Gly Tyr Gly Gln Gly Pro Tyr
         130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Gly Ser Gly Gln Gln Gly Pro
             165                 170                 175

Gly Gly Tyr Gly Pro Tyr Ala Ser Ala Ala Ala Ala Gly Gly Tyr
             180                 185                 190

Gly Ser Gly Pro Gly Gln Gln Gly Pro Tyr Gly Pro Gly Gly Ser Gly
             195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gly Pro Tyr Gly Pro Gly Ser Ser
225                 230                 235                 240

Ala Ala Ala Ala Ala Gly Gly Tyr Gly Tyr Gly Pro Gly Gly Gln Gly
             245                 250                 255

Pro Tyr Gly Pro Gly Ala Ser Gly Gly Asn Gly Pro Gly Ser Gly Gly
             260                 265                 270

Tyr Gly Pro Gly Gln Gln Gly Pro Gly Ser Ala Ala Ala Ala
             275                 280                 285

Gly Pro Gly Gly Gln Gly Pro Tyr Gly Pro Gly Ala Ser Ala Ala Ala
             290                 295                 300

Ala Ala Gly Gly Tyr Gly Pro Gly Gly Gln Gly Pro Gly Gly Tyr Gly
305                 310                 315                 320

```
Pro Gly Ser Ser Gly Pro Gly Gln Gly Pro Tyr Gly Pro Gly Ser
            325                 330                 335

Ser Ala Ala Ala Ala Gly Gly Tyr Gly Pro Gly Gln Gln Gly Pro
            340                 345                 350

Tyr Gly Pro Gly Gly Ser Ala Ala Ala Gly Gly Tyr Gln Gln
            355                 360                 365

Gly Pro Gly Gly Gln Gly Pro Tyr Gly Pro Gly Ala Ser Gly Pro Gly
        370                 375                 380

Gly Gln Gly Pro Tyr Gly Pro Gly Ala Ser Ala Ala Ala Ala Gly
385                 390                 395                 400

Pro Gly Gly Tyr Gly Pro Gly Gln Gly Pro Ser Ala Ser Ala Ala
            405                 410                 415

Ala Ala Ala Gly Gly Tyr Gly Ser Gly Pro Gly Gly Tyr Gly Pro Tyr
            420                 425                 430

Gly Pro Gly Gly Ser Gly Pro Gly Ser Gly Gln Gln Gly Gln Gly Pro
            435                 440                 445

Tyr Gly Pro Gly Ala Ser Ala Ala Ala Ala Gly Gly Tyr Gly Pro
        450                 455                 460

Gly Gln Gln Gly Pro Tyr Gly Pro Gly Ser Ala Ala Ala Ala
465                 470                 475                 480

Gly Pro Gly Ser Gly Gly Tyr Gly Pro Gly Ala Ser Gly Gly Asn Gly
            485                 490                 495

Pro Gly Ser Gly Gly Tyr Gly Pro Gln Gln Gly Pro Gly Gly Ser
            500                 505                 510

Ala Ala Ala Ala Gly Gly Tyr Gln Gln Gly Pro Gly Gly Gln Gly
            515                 520                 525

Pro Tyr Gly Pro Gly Ala Ser Ala Ala Ala Ala Gly Gly Tyr Gly
            530                 535                 540

Ser Gly Pro Gly Gln Gln Gly Pro Tyr Gly Pro Gly Gly Ser Gly Ser
545                 550                 555                 560

Gly Gln Gln Gly Pro Gly Gln Gly Pro Tyr Ala Ser Ala Ala Ala
            565                 570                 575

Ala Ala Gly Pro Gly Ser Gly Gln Gln Gly Pro Gly Ala Ser
            580                 585                 590

<210> SEQ ID NO 42
<211> LENGTH: 601
<212> TYPE: PRT
<213> ORGANISM: Artificial Sequence
<220> FEATURE:
<223> OTHER INFORMATION: PRT399

<400> SEQUENCE: 42

Met His His His His His Ser Ser Gly Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Gly Gly Tyr
            35                  40                  45

Gly Pro Gly Gly Gln Gly Pro Gln Gln Gly Pro Gly Ser Ser Ala
        50                  55                  60

Ala Ala Ala Gly Pro Gly Gly Tyr Gly Pro Gly Gln Gly Pro
65                  70                  75                  80

Ser Ala Ser Ala Ala Ala Ala Gly Pro Gly Ser Gly Gln Gln Gly
            85                  90                  95
```

```
Pro Gly Ala Ser Gly Gly Tyr Gly Pro Gly Gln Gly Pro Gly Gln
            100                 105                 110

Gln Gly Pro Gly Ser Ser Ala Ala Ala Ala Gly Gly Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser
                    165                 170                 175

Ala Ala Ala Ala Gly Ser Gly Gln Gln Gly Pro Gly Tyr Gly Pro
                180                 185                 190

Tyr Ala Ser Ala Ala Ala Ala Gly Gly Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala
                245                 250                 255

Gly Gly Tyr Gly Tyr Gly Pro Gly Gln Gly Pro Tyr Gly Pro Gly
            260                 265                 270

Ala Ser Gly Gly Asn Gly Pro Gly Ser Gly Tyr Gly Pro Gly Gln
            275                 280                 285

Gln Gly Pro Gly Gly Ser Ala Ala Ala Ala Gly Pro Gly Gly Gln
            290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
                    325                 330                 335

Pro Gly Gly Gln Gly Pro Tyr Gly Pro Gly Ser Ser Ala Ala Ala Ala
                340                 345                 350

Ala Gly Gly Tyr Gly Pro Gly Gln Gln Gly Pro Tyr Gly Pro Gly Gly
            355                 360                 365

Ser Ala Ala Ala Ala Gly Gly Tyr Gln Gln Gly Pro Gly Gly Gln
            370                 375                 380

Gly Pro Tyr Gly Pro Gly Ala Ser Gly Pro Gly Gly Gln Gly Pro Tyr
385                 390                 395                 400

Gly Pro Gly Ala Ser Ala Ala Ala Ala Gly Pro Gly Gly Tyr Gly
                    405                 410                 415

Pro Gly Gly Gln Gly Pro Ser Ala Ser Ala Ala Ala Ala Gly Gly
            420                 425                 430

Tyr Gly Ser Gly Pro Gly Gly Tyr Gly Pro Tyr Gly Pro Gly Gly Ser
            435                 440                 445

Gly Pro Gly Ser Gly Gln Gln Gly Gln Gly Pro Tyr Gly Pro Gly Ala
            450                 455                 460

Ser Ala Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
                    485                 490                 495

Gly Tyr Gly Pro Gly Ala Ser Gly Gly Asn Gly Pro Gly Ser Gly Gly
            500                 505                 510
```

```
Tyr Gly Pro Gly Gln Gln Gly Pro Gly Ser Ala Ala Ala Ala
            515                 520                 525

Gly Gly Tyr Gln Gln Gly Pro Gly Gln Gly Pro Tyr Gly Pro Gly
        530                 535                 540

Ala Ser Ala Ala Ala Ala Gly Gly Tyr Gly Ser Gly Pro Gly Gln
545                 550                 555                 560

Gln Gly Pro Tyr Gly Pro Gly Ser Gly Ser Gly Gln Gln Gly Pro
                565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600
```

<210> SEQ ID NO 43
<211> LENGTH: 612
<212> TYPE: PRT
<213> ORGANISM: Artificial Sequence
<220> FEATURE:
<223> OTHER INFORMATION: Met-PRT720

<400> SEQUENCE: 43

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Gly Gln Tyr Gly Pro Gly Gln Gln Gly Pro Gly Gln Gln Gly
            35                  40                  45

Pro Gly Ser Ser Ala Ala Ala Ala Ala Gly Pro Gly Gln Tyr Val Leu
        50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Gly Ser Tyr Gly Ser Val Leu Ile Gly Pro
        115                 120                 125

Gly Gln Gln Val Leu Ile Gly Pro Tyr Gly Ser Ala Ala Ala Ala Ala
130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
                165                 170                 175

Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Gly
        195                 200                 205

Gln Tyr Gly Ser Gly Pro Gly Gln Gln Gly Pro Gly Pro Gly Gln
    210                 215                 220

Ser Gly Ser Gly Gln Gln Gly Pro Gly Gln Gln Gly Pro Tyr Ala Ser
225                 230                 235                 240

Ala Ala Ala Ala Ala Gly Pro Gly Gln Gln Val Leu Ile Gly Pro Tyr
                245                 250                 255

Val Leu Ile Gly Pro Gly Ser Ser Ala Ala Ala Ala Gly Gln Tyr
            260                 265                 270
```

```
Gly Tyr Gly Pro Gly Gln Gln Gly Pro Tyr Gly Pro Gly Ala Ser Gly
            275                 280                 285

Gln Asn Gly Pro Gly Ser Gly Gln Tyr Gly Pro Gly Gln Gln Gly Pro
        290                 295                 300

Gly Gln Ser Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala
                325                 330                 335

Gly Gln Tyr Gly Pro Gly Gln Gln Pro Gly Gln Tyr Gly Pro Gly
            340                 345                 350

Ser Ser Gly Pro Gly Gln Gln Gly Pro Tyr Gly Pro Gly Ser Ser Ala
        355                 360                 365

Ala Ala Ala Ala Gly Ser Tyr Gly Pro Gly Gln Gln Val Leu Ile Gly
370                 375                 380

Pro Tyr Val Leu Ile Gly Pro Gly Pro Ser Ala Ala Ala Ala Gly
385                 390                 395                 400

Gln Tyr Gln Gln Gly Pro Gly Gln Gln Gly Pro Tyr Gly Pro Gly Ala
            405                 410                 415

Ser Gly Pro Gly Gln Gln Gly Pro Tyr Gly Pro Gly Ala Ser Ala Ala
        420                 425                 430

Ala Ala Ala Gly Pro Gly Gln Tyr Val Leu Ile Gly Pro Gly Gln Gln
    435                 440                 445

Val Leu Ile Gly Pro Ser Ala Ser Ala Ala Ala Ala Gly Gln Tyr
    450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
            485                 490                 495

Ala Ala Ala Ala Ala Gly Ser Tyr Gly Pro Gly Gln Gln Val Leu Ile
                500                 505                 510

Gly Pro Tyr Val Leu Ile Gly Pro Gly Ser Ala Ala Ala Ala
    515                 520                 525

Gly Pro Gly Ser Gly Gln Tyr Gly Pro Gly Ala Ser Gly Gln Asn Gly
    530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
                565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
        595                 600                 605

Ser Val Leu Ile
    610

<210> SEQ ID NO 44
<211> LENGTH: 592
<212> TYPE: PRT
<213> ORGANISM: Artificial Sequence
<220> FEATURE:
<223> OTHER INFORMATION: Met-PRT665

<400> SEQUENCE: 44

Met Gly Pro Gly Gln Gln Gly Pro Tyr Gly Pro Gly Ala Ser Ala Ala
1               5                   10                  15
```

```
Ala Ala Ala Ala Ala Gly Ser Asn Gly Pro Gly Ser Gly Gln Gly
                 20                  25                  30
Pro Gly Gln Ser Gly Gln Tyr Gly Pro Gly Gln Gln Gly Pro Gly Gln
             35                  40                  45
Gln Gly Pro Gly Ser Ser Ala Ala Ala Ala Ala Ala Gly Pro Gly
         50                  55                  60
Gln Tyr Val Leu Ile Gly Pro Gly Gln Gln Gly Pro Ser Ala Ser Ala
 65              70                  75                  80
Ala Ala Ala Ala Ala Gly Pro Gly Ser Gly Gln Gln Gly Pro Gly
                 85                  90                  95
Ala Ser Gly Gln Tyr Gly Pro Gly Gln Gln Gly Pro Gly Gln Gln Gly
             100                 105                 110
Pro Gly Ser Ser Ala Ala Ala Ala Ala Ala Gly Ser Tyr Gly Ser
             115                 120                 125
Val Leu Ile Gly Pro Gly Gln Gln Gly Pro Tyr Gly Ser Ala Ala Ala
         130                 135                 140
Ala Ala Ala Ala Gly Pro Gly Ser Gly Gln Tyr Gly Gln Gly Pro Tyr
145                 150                 155                 160
Gly Pro Gly Ala Ser Gly Pro Gly Gln Tyr Gly Pro Gly Gln Gln Gly
             165                 170                 175
Pro Ser Ala Ser Ala Ala Ala Ala Ala Ala Gly Ser Gly Gln Gln
             180                 185                 190
Val Leu Ile Gly Pro Gly Gln Tyr Gly Pro Tyr Ala Ser Ala Ala Ala
         195                 200                 205
Ala Ala Ala Ala Gly Ser Tyr Gly Ser Gly Pro Gly Gln Gln Gly Pro
210                 215                 220
Tyr Gly Pro Gly Gln Ser Gly Ser Gly Gln Gln Gly Pro Gly Gln Gln
225                 230                 235                 240
Gly Pro Tyr Ala Ser Ala Ala Ala Ala Ala Ala Gly Pro Gly Gln
             245                 250                 255
Gln Val Leu Ile Gly Pro Tyr Gly Pro Gly Ser Ser Ala Ala Ala Ala
         260                 265                 270
Ala Ala Ala Gly Ser Tyr Gly Tyr Gly Pro Gly Gln Gln Gly Pro Tyr
275                 280                 285
Gly Pro Gly Ala Ser Gly Gln Asn Gly Pro Gly Ser Gly Gln Tyr Gly
             290                 295                 300
Pro Gly Gln Gln Gly Pro Gly Pro Ser Ala Ala Ala Ala Ala Ala
305                 310                 315                 320
Gly Pro Gly Gln Gln Val Leu Ile Gly Pro Tyr Gly Pro Gly Ala Ser
             325                 330                 335
Ala Ala Ala Ala Ala Ala Gly Ser Tyr Gly Pro Gly Gln Gln Gly
             340                 345                 350
Pro Gly Gln Tyr Gly Pro Gly Ser Ser Gly Pro Gly Gln Gln Gly Pro
         355                 360                 365
Tyr Gly Pro Gly Ser Ser Ala Ala Ala Ala Ala Gly Ser Tyr
             370                 375                 380
Gly Pro Gly Gln Gln Val Leu Ile Gly Pro Tyr Gly Pro Gly Pro Ser
385                 390                 395                 400
Ala Ala Ala Ala Ala Ala Gly Ser Tyr Gln Gln Gly Pro Gly Gln
             405                 410                 415
Gln Gly Pro Tyr Gly Pro Gly Ala Ser Gly Pro Gly Gln Gln Gly Pro
         420                 425                 430
Tyr Gly Pro Gly Ala Ser Ala Ala Ala Ala Ala Ala Gly Pro Gly
```

```
                435                 440                 445
Gln Tyr Val Leu Ile Gly Pro Gly Gln Gln Gly Pro Ser Ala Ser Ala
450                 455                 460

Ala Ala Ala Ala Ala Gly Ser Tyr Gly Ser Gly Pro Gly Gln Tyr
465                 470                 475                 480

Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala
                500                 505                 510

Gly Ser Tyr Gly Pro Gly Gln Gln Val Leu Ile Gly Pro Tyr Gly Pro
            515                 520                 525

Gly Pro Ser Ala Ala Ala Ala Ala Ala Gly Pro Gly Ser Gly Gln
            530                 535                 540

Tyr Gly Pro Gly Ala Ser Gly Gln Asn Gly Pro Gly Ser Gly Gln Tyr
545                 550                 555                 560

Gly Pro Gly Gln Gln Gly Pro Gly Pro Ser Ala Ala Ala Ala Ala
                565                 570                 575

Ala Gly Pro Gly Ser Gly Gln Gln Gly Pro Gly Ala Ser Val Leu Ile
            580                 585                 590

<210> SEQ ID NO 45
<211> LENGTH: 619
<212> TYPE: PRT
<213> ORGANISM: Artificial Sequence
<220> FEATURE:
<223> OTHER INFORMATION: Met-PRT666

<400> SEQUENCE: 45

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
        50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
            100                 105                 110

Gln Gln Gly Pro Gly Ser Ser Ala Ala Ala Ala Ala Ala Gly Ser
        115                 120                 125

Tyr Gly Ser Val Leu Ile Gly Pro Gly Gln Gln Val Leu Ile Gly Pro
130                 135                 140

Tyr Gly Ser Ala Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
                165                 170                 175

Gly Pro Gly Gln Gln Gly Pro Ser Ser Ala Ala Ala Ala Ala
            180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Ala Gly Ser Tyr
```

```
            210                 215                 220
Gly Ser Gly Pro Gly Gln Gly Pro Tyr Gly Pro Gly Gln Ser Gly
225                 230                 235                 240

Ser Gly Gln Gln Gly Pro Gly Gln Gly Pro Tyr Ala Ser Ala Ala
            245                 250                 255

Ala Ala Ala Ala Ala Gly Pro Gly Gln Gln Val Leu Ile Gly Pro Tyr
                260                 265                 270

Val Leu Ile Gly Pro Ser Ala Ala Ala Ala Ala Ala Gly
            275                 280                 285

Ser Tyr Gly Tyr Gly Pro Gly Gln Gln Gly Pro Tyr Gly Pro Gly Ala
            290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Gly Pro Gly Gln
                325                 330                 335

Gln Val Leu Ile Gly Pro Tyr Val Leu Ile Gly Pro Gly Ala Ser Ala
                340                 345                 350

Ala Ala Ala Ala Ala Gly Ser Tyr Gly Pro Gly Gln Gln Gly Pro
            355                 360                 365

Gly Gln Tyr Gly Pro Gly Ser Ser Gly Pro Gly Gln Gln Gly Pro Tyr
370                 375                 380

Gly Pro Gly Ser Ser Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
                405                 410                 415

Pro Ser Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
            435                 440                 445

Gly Pro Tyr Gly Pro Gly Ala Ser Ala Ala Ala Ala Ala Ala Gly
            450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Gly Ser Tyr Gly Ser
            485                 490                 495

Gly Pro Gly Gln Tyr Gly Pro Tyr Gly Pro Gly Gln Ser Gly Pro Gly
            500                 505                 510

Ser Gly Gln Gln Gly Gln Gly Pro Tyr Gly Pro Gly Ala Ser Ala Ala
            515                 520                 525

Ala Ala Ala Ala Gly Ser Tyr Gly Pro Gly Gln Gln Val Leu Ile
            530                 535                 540

Gly Pro Tyr Val Leu Ile Gly Pro Gly Pro Ser Ala Ala Ala Ala
545                 550                 555                 560

Ala Ala Gly Pro Gly Ser Gly Gln Tyr Gly Pro Gly Ala Ser Gly Gln
            565                 570                 575

Asn Gly Pro Gly Ser Gly Gln Tyr Gly Pro Gly Gln Gln Gly Pro Gly
            580                 585                 590

Pro Ser Ala Ala Ala Ala Ala Ala Gly Pro Gly Ser Gly Gln Gln
            595                 600                 605

Val Leu Ile Gly Pro Gly Ala Ser Val Leu Ile
610                 615

<210> SEQ ID NO 46
```

<211> LENGTH: 623
<212> TYPE: PRT
<213> ORGANISM: Artificial Sequence
<220> FEATURE:
<223> OTHER INFORMATION: PRT720

<400> SEQUENCE: 46

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
        50                  55                  60

Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
            85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala
        115                 120                 125

Ala Gly Ser Tyr Gly Ser Val Leu Ile Gly Pro Gly Gln Gln Val Leu
        130                 135                 140

Ile Gly Pro Tyr Gly Ser Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala
        180                 185                 190

Gly Ser Gly Gln Gln Val Leu Ile Gly Pro Gly Gln Tyr Val Leu Ile
        195                 200                 205

Gly Pro Tyr Ala Ser Ala Ala Ala Ala Gly Gln Tyr Gly Ser Gly
        210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala
            245                 250                 255

Gly Pro Gly Gln Gln Val Leu Ile Gly Pro Tyr Val Leu Ile Gly Pro
        260                 265                 270

Gly Ser Ser Ala Ala Ala Ala Gly Gln Tyr Gly Tyr Gly Pro Gly
        275                 280                 285

Gln Gln Gly Pro Tyr Gly Pro Gly Ala Ser Gly Gln Asn Gly Pro Gly
        290                 295                 300

Ser Gly Gln Tyr Gly Pro Gly Gln Gln Gly Pro Gly Gln Ser Ala Ala
305                 310                 315                 320

Ala Ala Ala Gly Pro Gly Gln Gln Val Leu Ile Gly Pro Tyr Val Leu
            325                 330                 335

Ile Gly Pro Gly Ala Ser Ala Ala Ala Ala Gly Gln Tyr Gly Pro
        340                 345                 350

Gly Gln Gln Gly Pro Gly Gln Tyr Gly Pro Gly Ser Ser Gly Pro Gly
        355                 360                 365

Gln Gln Gly Pro Tyr Gly Pro Gly Ser Ser Ala Ala Ala Ala Gly
        370                 375                 380
```

```
Ser Tyr Gly Pro Gly Gln Gln Val Leu Ile Gly Pro Tyr Val Leu Ile
385                 390                 395                 400

Gly Pro Gly Pro Ser Ala Ala Ala Ala Gly Gln Tyr Gln Gln Gly
                405                 410                 415

Pro Gly Gln Gln Gly Pro Tyr Gly Pro Gly Ala Ser Gly Pro Gly Gln
                420                 425                 430

Gln Gly Pro Tyr Gly Pro Gly Ala Ser Ala Ala Ala Ala Gly Pro
            435                 440                 445

Gly Gln Tyr Val Leu Ile Gly Pro Gln Gln Val Leu Ile Gly Pro
        450                 455                 460

Ser Ala Ser Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
                485                 490                 495

Gln Gly Gln Gly Pro Tyr Gly Pro Gly Ala Ser Ala Ala Ala Ala
                500                 505                 510

Gly Ser Tyr Gly Pro Gly Gln Gln Val Leu Ile Gly Pro Tyr Val Leu
            515                 520                 525

Ile Gly Pro Gly Pro Ser Ala Ala Ala Ala Gly Pro Gly Ser Gly
        530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala
                565                 570                 575

Gly Gln Tyr Gln Gln Val Leu Ile Gly Pro Gly Gln Gly Pro Tyr
                580                 585                 590

Val Leu Ile Gly Pro Gly Ala Ser Ala Ala Ala Ala Gly Pro Gly
            595                 600                 605

Ser Gly Gln Gln Val Leu Ile Gly Pro Gly Ala Ser Val Leu Ile
    610                 615                 620

<210> SEQ ID NO 47
<211> LENGTH: 603
<212> TYPE: PRT
<213> ORGANISM: Artificial Sequence
<220> FEATURE:
<223> OTHER INFORMATION: PRT665

<400> SEQUENCE: 47

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
        50                  55                  60

Ser Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala
                85                  90                  95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
        115                 120                 125
```

```
Ala Ala Ala Ala Ala Ala Gly Ser Tyr Gly Ser Val Leu Ile Gly Pro
        130                 135                 140
Gly Gln Gln Gly Pro Tyr Gly Ser Ala Ala Ala Ala Ala Ala Ala Gly
145                 150                 155                 160
Pro Gly Ser Gly Gln Tyr Gly Gln Gly Pro Tyr Gly Pro Gly Ala Ser
                165                 170                 175
Gly Pro Gly Gln Tyr Gly Pro Gly Gln Gln Gly Pro Ser Ala Ser Ala
                180                 185                 190
Ala Ala Ala Ala Ala Ala Gly Ser Gly Gln Gln Val Leu Ile Gly Pro
                195                 200                 205
Gly Gln Tyr Gly Pro Tyr Ala Ser Ala Ala Ala Ala Ala Ala Ala Gly
210                 215                 220
Ser Tyr Gly Ser Gly Pro Gly Gln Gln Gly Pro Tyr Gly Pro Gly Gln
225                 230                 235                 240
Ser Gly Ser Gly Gln Gln Gly Pro Gly Gln Gln Gly Pro Tyr Ala Ser
                245                 250                 255
Ala Ala Ala Ala Ala Ala Ala Gly Pro Gly Gln Gln Val Leu Ile Gly
                260                 265                 270
Pro Tyr Gly Pro Gly Ser Ser Ala Ala Ala Ala Ala Ala Ala Gly Ser
                275                 280                 285
Tyr Gly Tyr Gly Pro Gly Gln Gln Gly Pro Tyr Gly Pro Gly Ala Ser
                290                 295                 300
Gly Gln Asn Gly Pro Gly Ser Gly Gln Tyr Gly Pro Gly Gln Gln Gly
305                 310                 315                 320
Pro Gly Pro Ser Ala Ala Ala Ala Ala Ala Gly Pro Gly Gln Gln
                325                 330                 335
Val Leu Ile Gly Pro Tyr Gly Pro Gly Ala Ser Ala Ala Ala Ala Ala
                340                 345                 350
Ala Ala Gly Ser Tyr Gly Pro Gly Gln Gln Gly Pro Gly Gln Tyr Gly
                355                 360                 365
Pro Gly Ser Ser Gly Pro Gly Gln Gln Gly Pro Tyr Gly Pro Gly Ser
                370                 375                 380
Ser Ala Ala Ala Ala Ala Ala Ala Gly Ser Tyr Gly Pro Gly Gln Gln
385                 390                 395                 400
Val Leu Ile Gly Pro Tyr Gly Pro Gly Pro Ser Ala Ala Ala Ala Ala
                405                 410                 415
Ala Ala Gly Ser Tyr Gln Gln Gly Pro Gly Gln Gln Gly Pro Tyr Gly
                420                 425                 430
Pro Gly Ala Ser Gly Pro Gly Gln Gln Gly Pro Tyr Gly Pro Gly Ala
                435                 440                 445
Ser Ala Ala Ala Ala Ala Ala Ala Gly Pro Gly Gln Tyr Val Leu Ile
                450                 455                 460
Gly Pro Gly Gln Gln Gly Pro Ser Ala Ser Ala Ala Ala Ala Ala Ala
465                 470                 475                 480
Ala Gly Ser Tyr Gly Ser Gly Pro Gly Gln Tyr Gly Pro Tyr Gly Pro
                485                 490                 495
Gly Gln Ser Gly Pro Gly Ser Gly Gln Gln Gly Gln Gly Pro Tyr Gly
                500                 505                 510
Pro Gly Ala Ser Ala Ala Ala Ala Ala Ala Ala Gly Ser Tyr Gly Pro
                515                 520                 525
Gly Gln Gln Val Leu Ile Gly Pro Tyr Gly Pro Gly Pro Ser Ala Ala
                530                 535                 540
```

Ala Ala Ala Ala Gly Pro Gly Ser Gly Gln Tyr Gly Pro Gly Ala
545                 550                 555                 560

Ser Gly Gln Asn Gly Pro Gly Ser Gly Gln Tyr Gly Pro Gly Gln
                565                 570                 575

Gly Pro Gly Pro Ser Ala Ala Ala Ala Ala Ala Gly Pro Gly Ser
            580                 585                 590

Gly Gln Gln Gly Pro Gly Ala Ser Val Leu Ile
        595                 600

<210> SEQ ID NO 48
<211> LENGTH: 630
<212> TYPE: PRT
<213> ORGANISM: Artificial Sequence
<220> FEATURE:
<223> OTHER INFORMATION: PRT666

<400> SEQUENCE: 48

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala Ala
                85                  90                  95

Ala Ala Ala Ala Gly Pro Gly Ser Gly Gln Gln Gly Pro Gly Ala Ser
                100                 105                 110

Gly Gln Tyr Gly Pro Gly Gln Gln Gly Pro Gly Gln Gln Gly Pro Gly
            115                 120                 125

Ser Ser Ala Ala Ala Ala Ala Ala Gly Ser Tyr Gly Ser Val Leu
130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gly Gln Gly Pro
                165                 170                 175

Tyr Gly Pro Gly Ala Ser Gly Pro Gly Gln Tyr Gly Pro Gly Gln Gln
            180                 185                 190

Gly Pro Ser Ala Ser Ala Ala Ala Ala Ala Gly Ser Gly Gln
        195                 200                 205

Gln Val Leu Ile Gly Pro Gly Gln Tyr Val Leu Ile Gly Pro Tyr Ala
    210                 215                 220

Ser Ala Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
                245                 250                 255

Pro Gly Gln Gln Gly Pro Tyr Ala Ser Ala Ala Ala Ala Ala Ala
            260                 265                 270

Gly Pro Gly Gln Gln Val Leu Ile Gly Pro Tyr Val Leu Ile Gly Pro
        275                 280                 285

Gly Ser Ser Ala Ala Ala Ala Ala Ala Gly Ser Tyr Gly Tyr Gly
    290                 295                 300

```
Pro Gly Gln Gln Gly Pro Tyr Gly Pro Gly Ala Ser Gly Gln Asn Gly
305             310             315             320

Pro Gly Ser Gly Gln Tyr Gly Pro Gly Gln Gln Gly Pro Gly Pro Ser
            325             330             335

Ala Ala Ala Ala Ala Ala Ala Gly Pro Gly Gln Gln Val Leu Ile Gly
            340             345             350

Pro Tyr Val Leu Ile Gly Pro Gly Ala Ser Ala Ala Ala Ala Ala Ala
        355             360             365

Ala Gly Ser Tyr Gly Pro Gly Gln Gln Gly Pro Gly Gln Tyr Gly Pro
        370             375             380

Gly Ser Ser Gly Pro Gly Gln Gln Gly Pro Tyr Gly Pro Gly Ser Ser
385             390             395             400

Ala Ala Ala Ala Ala Ala Ala Gly Ser Tyr Gly Pro Gly Gln Gln Val
            405             410             415

Leu Ile Gly Pro Tyr Val Leu Ile Gly Pro Gly Pro Ser Ala Ala Ala
            420             425             430

Ala Ala Ala Ala Gly Ser Tyr Gln Gln Gly Pro Gly Gln Gln Gly Pro
            435             440             445

Tyr Gly Pro Gly Ala Ser Gly Pro Gly Gln Gln Gly Pro Tyr Gly Pro
    450             455             460

Gly Ala Ser Ala Ala Ala Ala Ala Ala Gly Pro Gly Gln Tyr Gly Val
465             470             475             480

Leu Ile Gly Pro Gly Gln Gln Val Leu Ile Gly Pro Ser Ala Ser Ala
            485             490             495

Ala Ala Ala Ala Ala Gly Ser Tyr Gly Ser Gly Pro Gly Gln Tyr
            500             505             510

Gly Pro Tyr Gly Pro Gly Gln Ser Gly Pro Gly Ser Gly Gln Gln Gly
        515             520             525

Gln Gly Pro Tyr Gly Pro Gly Ala Ser Ala Ala Ala Ala Ala Ala
        530             535             540

Gly Ser Tyr Gly Pro Gly Gln Val Leu Ile Gly Pro Tyr Val Leu
545             550             555             560

Ile Gly Pro Gly Pro Ser Ala Ala Ala Ala Ala Ala Gly Pro Gly
            565             570             575

Ser Gly Gln Tyr Gly Pro Gly Ala Ser Gly Gln Asn Gly Pro Gly Ser
            580             585             590

Gly Gln Tyr Gly Pro Gly Gln Gln Gly Pro Gly Pro Ser Ala Ala Ala
        595             600             605

Ala Ala Ala Ala Gly Pro Gly Ser Gly Gln Gln Val Leu Ile Gly Pro
610             615             620

Gly Ala Ser Val Leu Ile
625             630
```